United States Patent
Feyen et al.

(10) Patent No.: US 10,913,660 B2
(45) Date of Patent: Feb. 9, 2021

(54) CHA TYPE ZEOLITIC MATERIALS AND METHODS FOR THEIR PREPARATION USING COMBINATIONS OF CYCLOALKYL AND ETHYLTRIMETHYLAMMONIUM COMPOUNDS

(71) Applicant: BASF Corporation, Florham Park, NJ (US)

(72) Inventors: Mathias Feyen, Laudenbach (DE); Roger Ruetz, Ludwigshafen (DE); Ulrich Mueller, Neustadt (DE); Manzoor Sultan, Princeton Junction, NJ (US)

(73) Assignee: BASF Corporation, Florham Park, NJ (US)

( * ) Notice: Subject to any disclaimer, the term of this patent is extended or adjusted under 35 U.S.C. 154(b) by 211 days.

(21) Appl. No.: 16/060,739

(22) PCT Filed: Dec. 8, 2016

(86) PCT No.: PCT/US2016/065488
§ 371 (c)(1),
(2) Date: Jun. 8, 2018

(87) PCT Pub. No.: WO2017/100384
PCT Pub. Date: Jun. 15, 2017

(65) Prior Publication Data
US 2018/0362357 A1    Dec. 20, 2018

Related U.S. Application Data

(60) Provisional application No. 62/264,889, filed on Dec. 9, 2015.

(51) Int. Cl.
*C01B 39/48* (2006.01)
*B01J 29/70* (2006.01)
(Continued)

(52) U.S. Cl.
CPC ............... *C01B 39/48* (2013.01); *B01J 20/18* (2013.01); *B01J 29/7015* (2013.01);
(Continued)

(58) Field of Classification Search
CPC .. C01B 39/48; B01J 29/70; B01J 20/18; B01J 29/7015; B01J 29/763; B01J 35/1042;
(Continued)

(56) References Cited

U.S. PATENT DOCUMENTS 4,544,538 A   10/1985  Zones
4,610,854 A    9/1986  Zones
(Continued)

FOREIGN PATENT DOCUMENTS

EP      2 325 143 A2   5/2011
WO   WO 2008/033229 A2   3/2008
(Continued)

OTHER PUBLICATIONS

International Preliminary Report on Patentability and Written Opinion dated Jun. 12, 2018 in PCT/US2016/065488 (English Translation only), 7 pages.
(Continued)

*Primary Examiner* — David M Brunsman
(74) *Attorney, Agent, or Firm* — Oblon, McClelland, Maier & Neustadt, L.L.P.

(57) ABSTRACT

The present invention relates to a process for the preparation of a zeolitic material having a CHA-type framework structure comprising $YO_2$ and $X_2O_3$, wherein said process comprises the steps of: (1) providing a mixture comprising one or more sources for $YO_2$, one or more sources for $X_2O_3$, one or more optionally substituted ethyltrimethylammonium cation-containing compounds, and one or more tetraalkylammonium cation $R^1R^2R^3R^4N^+$-containing compounds as structure directing agent; (2) crystallizing the mixture
(Continued)

obtained in step (1) for obtaining a zeolitic material having a CHA-type framework structure; wherein Y is a tetravalent element and X is a trivalent element, wherein $R^1$, $R^2$, and $R^3$ independently from one another stand for alkyl, wherein $R^4$ stands for cycloalkyl, and wherein the $YO_2:X_2O_3$ molar ratio of the mixture in (1) ranges from 2 to 1,000, as well as to zeolitic materials which may be obtained according to the inventive process and to their use.

20 Claims, 19 Drawing Sheets

(51) Int. Cl.

| | | |
|---|---|---|
| *B01J 29/76* | (2006.01) | |
| *B01J 20/18* | (2006.01) | |
| *B01J 37/00* | (2006.01) | |
| *B01J 37/06* | (2006.01) | |
| *B01J 37/08* | (2006.01) | |
| *B01J 35/10* | (2006.01) | |
| *B01J 37/02* | (2006.01) | |
| *B01D 53/94* | (2006.01) | |
| *B01D 53/02* | (2006.01) | |

(52) U.S. Cl.
CPC ......... *B01J 29/7065* (2013.01); *B01J 29/763* (2013.01); *B01J 37/0045* (2013.01); *B01J 37/06* (2013.01); *B01J 37/08* (2013.01); *B01D 53/02* (2013.01); *B01D 53/9418* (2013.01); *B01D 2257/504* (2013.01); *B01J 35/1057* (2013.01); *B01J 35/1061* (2013.01); *B01J 37/0246* (2013.01); *B01J 2229/186* (2013.01); *C01P 2002/72* (2013.01); *C01P 2002/82* (2013.01); *C01P 2004/51* (2013.01); *C01P 2004/62* (2013.01); *C01P 2006/14* (2013.01); *C01P 2006/16* (2013.01); *C07C 2529/70* (2013.01); *C07C 2529/76* (2013.01)

(58) Field of Classification Search
CPC ............. B01D 53/9418; C01P 2002/82; C01P 2004/62; C01P 2006/08; C01P 2006/14; C01P 2004/51; C07C 2529/70; C07C 2529/76

See application file for complete search history.

(56) References Cited

U.S. PATENT DOCUMENTS

| | | |
|---|---|---|
| 2004/0253163 A1 | 12/2004 | Cao et al. |
| 2005/0065016 A1 | 3/2005 | Lewis et al. |
| 2005/0197520 A1 | 9/2005 | Mertens et al. |
| 2007/0043249 A1 | 2/2007 | Cao et al. |
| 2011/0142755 A1 | 6/2011 | Bull et al. |
| 2013/0323164 A1 | 12/2013 | Feyen et al. |
| 2015/0284255 A1* | 10/2015 | Maurer ................ B01J 29/7038 423/714 |
| 2018/0186648 A1* | 7/2018 | Feyen ..................... C01B 39/48 |
| 2018/0362357 A1* | 12/2018 | Feyen ..................... C01B 39/48 |
| 2019/0105639 A1* | 4/2019 | Maehama ................ B01J 23/72 |

FOREIGN PATENT DOCUMENTS

| | | |
|---|---|---|
| WO | WO 2008/039742 A1 | 4/2008 |
| WO | WO 2008/083048 A1 | 7/2008 |
| WO | WO 2009/141324 A1 | 11/2009 |
| WO | WO 2011/064186 A1 | 6/2011 |
| WO | WO 2013/182974 A1 | 12/2013 |
| WO | WO 2015/185625 A2 | 12/2015 |

OTHER PUBLICATIONS

L. M. Knight et al. "A Novel Screening Approach Utilizing Combinatorial Methods in the Ethyltrimethylammonium Template System", Studies in Surface Science and Catalysis; 2004, vol. 154, p. 171-179.
U.S. Appl. No. 15/779,314, filed May 25, 2018, Julia Burckhart.
U.S. Appl. No. 16/060,260, filed Jun. 7, 2018, Nicolas Vautravers.
U.S. Appl. No. 16/060,229, filed Jun. 7, 2018, Andrei-Nicolae.
U.S. Appl. No. 16/060,739, filed Jun. 8, 2018, Mathias Feyen, et al.
International Search Report and Written Opinion dated Feb. 8, 2017, in PCT/US2016/065488, filed Dec. 8, 2016.
Harris, T.V. et al., "A Study of Guest/Host Energetics for the Synthesis of Cage Structures NON and CHA", Studies in Surface Science and Catalysis, vol. 84, 1994, pp. 29-36.

* cited by examiner

CHA TYPE ZEOLITIC MATERIALS AND METHODS FOR THEIR PREPARATION USING COMBINATIONS OF CYCLOALKYL AND ETHYLTRIMETHYLAMMONIUM COMPOUNDS

This application is a 371 filing of PCT/US2016/65488, filed Dec. 8, 2016.

TECHNICAL FIELD

The present invention relates to a process for the preparation of a zeolitic material as well as to a zeolitic material having the CHA-type framework structure as such and as obtainable from the inventive process. Furthermore, the present invention relates to the use of the inventive zeolitic materials in specific applications.

INTRODUCTION

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the Atlas of Zeolite Framework Types, 5th edition, Elsevier, London, England (2001).

Among said zeolitic materials, Chabazite is a well studied example, wherein it is the classical representative of the class of zeolitic materials having a CHA framework structure. Besides aluminosilicates such as Chabazite, the class of zeolitic materials having a CHA framework structure comprises a large number of compounds further comprising phosphorous in the framework structure are known which are accordingly referred to as silicoaluminophosphates (SAPO). In addition to said compounds, further molecular sieves of the CHA structure type are known which contain aluminum and phosphorous in their framework, yet contain little or no silica, and are accordingly referred to as aluminophosphates (APO). Zeolitic materials belonging to the class of molecular sieves having the CHA-type framework structure are employed in a variety of applications, and in particular serve as heterogeneous catalysts in a wide range of reactions such as in methanol to olefin catalysis and selective catalytic reduction of nitrogen oxides $NO_x$ to name some two of the most important applications. Zeolitic materials of the CHA framework type are characterized by three-dimensional 8-membered-ring (8MR) pore/channel systems containing double-six-rings (D6R) and cages.

Zeolitic materials having a CHA-type framework structure and in particular Chabazite with incorporated copper ions (Cu-CHA) are widely used as heterogeneous catalyst for the selective catalytic reduction (SCR) of $NO_x$ fractions in automotive emissions. Based on the small pore openings and the alignment of the copper ions in the CHA cages, these catalyst systems have a unique thermal stability, which tolerates temperatures higher than 700° C. in presence of $H_2O$.

For the industrial production of CHA, cost intensive 1-adamantyltriemethylammoniumhydroxid among other expensive organotemplates are typically employed as structure directing agent in the synthetic procedures for their preparation. U.S. Pat. No. 4,544,538 for example relates to the production of SSZ-13 using 1N-alkyl-3-quinuclidinol, N,N,N-tetraalkyl-1-adamantammonium, or N,N,N-trialkyl-exoaminonorbornane as the structure directing agent, the SSZ-13 zeolitic material having a CHA-type framework structure.

WO-A-2008/083048, on the other hand, concerns a method for the production of SSZ-13 using a specific N,N,N-trimethyl benzyl quaternary ammonium cation in the presence of seed crystals. Similarly, WO-A-2008/039742 relates to a method for the production of SSZ-13 wherein a mixture of N,N,N-trialkyl benzyl quaternary ammonium cations and N,N,N-tetramethyl-1-adamantammonium are employed as the organotemplate in an effort for increasing cost effectiveness by attempting to reduce the amount of the cost-intensive N,N,N-tetramethyl-1-adamantammonium usually employed in the synthesis of SSZ-13.

WO-A-2008/033229, concerns a method for the production of microporous materials using dicycloalkylammonium compounds as organic templating agents.

WO 2009/141324 A1 relates to a method for the direct synthesis of Cu containing Zeolites having the CHA framework structure, wherein said document mentions N,N,N-trimethylcyclohexylammonium compounds among several compounds as possible structure directing agents for obtaining a zeolitic material having the CHA framework structure. Furthermore, said document teaches the use of a 1-adamantyltrimethylammonium compound in combination with a further ammonium compound which may be a tetramethylammonium compound.

WO 2011/064186 A1 and EP 2 325 143 A2, on the other hand, respectively relate to a process for the preparation of zeolites having the CHA framework structure which employ tetramethylammonium hydroxide in addition to at least one organic structure directing agent. Among the structure directing agents which may be used to this effect, said documents mention N,N,N-trimethylcyclohexylammonium compounds among several compounds as possible structure directing agents for obtaining a zeolitic material having the CHA framework structure, wherein however N,N,N-trimethyl-1-adamantyltrimethylammonium compounds are preferably and effectively taught in said documents for obtaining the aforementioned material.

U.S. Pat. No. 4,610,854 discloses the use of trimethylcyclohexylammonium for the production of SSZ-15, which is a zeolitic material displaying a framework structure other than the CHA-type. US-A-2007/0043249, on the other hand, relates to the use of a group of tetraalkylammonium compounds including trimethylcyclohexylammonium as organotemplates for the production of zeolitic materials having the CHA framework structure, wherein said materials are however restricted to alumino- or silicoaluminophosphates necessarily containing $P_2O_5$ in their respective frameworks.

Zones et al. "A Study of Guest/Host Energetics for the Synthesis of Cage Structures NON and CHA" in Studies in Surface Science and Catalysis, Vol. 84, pp. 29-36, Elsevier Science B.V. (1994) describes the synthesis of SSZ-13 using a variety of organotemplates including the trimethylcyclohexylammonium cation, wherein the latter would display very low rates of crystallization in particular when compared to the use of the adamantyltrimethylammonium cation. WO 2013/182974 A relates to the use of trimethylcyclohexylammoniumhydroxide as organotemplate for the synthesis of CHA-type zeolitic materials involving crystallization times of 48 hours or more.

Finally, US 2004/253163 A1 discloses a process for preparing a crystalline molecular sieve having the CHA type framework structure using an organic template, wherein preferably N,N-dimethyl-cyclohexylamine is employed as the organotemplate.

Consequently, there remains a need for a cost-effective process for the production of zeolitic materials having the CHA-type framework structure. Furthermore, there is an ongoing need for improved zeolitic materials having the CHA-type framework structure, in particular with respect to the catalytic properties for use in a variety of application and in particular for use in the treatment of $NO_x$ in automotive exhaust gas a catalyst and/or catalyst support. This applies in particular in view of national legislation and environmental policy which require increasing effectiveness of environmental catalysts such as Cu-Chabazite and related zeolitic materials.

DETAILED DESCRIPTION

It was therefore the object of the present invention to provide an improved CHA-type zeolitic material, as well as to provide an improved method for the production of such a catalyst, in particular in view of cost-effectiveness. Thus it has surprisingly been found that an improved CHA-type zeolite may be obtained by using a combination of one or more cycloalkylammonium compounds as organotemplates in the self-organizing synthetic procedures typical of zeolite chemistry together with one or more optionally substituted ethyltrimethylammonium cation-containing compounds. Thus, it has quite unexpectedly been found that besides providing an improved process for the production of said zeolitic materials, in particular with respect to the considerable increase in cost-effectiveness which may be achieved in view of the reduced reaction times necessary according to the inventive process, the resulting zeolitic materials per se display highly unexpected properties compared to the products of syntheses only employing a cycloalkylammonium or other organic structure directing agent by itself. This applies not only with respect to the unique physical and chemical properties of the materials obtained according to the inventive process but in particular with respect to their highly unexpected catalytic properties, and more specifically in view of their activity in SCR catalytic applications.

Therefore, the present invention relates to a process for the preparation of a zeolitic material having a CHA-type framework structure comprising $YO_2$ and $X_2O_3$, wherein said process comprises the steps of:
(1) providing a mixture comprising one or more sources for $YO_2$, one or more sources for $X_2O_3$, one or more optionally substituted ethyltrimethylammonium cation-containing compounds, and one or more tetraalkylammonium cation $R^1R^2R^3R^4N^+$-containing compounds as structure directing agent;
(2) crystallizing the mixture obtained in step (1) for obtaining a zeolitic material having a CHA-type framework structure;
wherein Y is a tetravalent element and X is a trivalent element,
wherein $R^1$, $R^2$, and $R^3$ independently from one another stand for alkyl,
wherein $R^4$ stands for cycloalkyl, and
wherein the $YO_2:X_2O_3$ molar ratio of the mixture in (1) ranges from 2 to 1,000, preferably from 3 to 500, more preferably from 5 to 300, more preferably from 10 to 100, more preferably from 15 to 50, more preferably from 20 to 40, more preferably from 23 to 35, more preferably from 25 to 30, and more preferably from 27 to 29.

Thus, it has surprisingly been found that by using a specific combination of a cycloalkylammonium cation as structure directing agent and one or more optionally substituted ethyltrimethylammonium cation-containing compounds according to the inventive process, a highly cost-effective process is provided, wherein even more unexpectedly, said improved process actually leads to an improved zeolitic material having the CHA-type framework structure compared to materials obtained by using the cycloalkylammonium cation by itself or in combination with a tetraalkylammonium cation other than the optionally substituted ethyltrimethylammonium cation in their respective synthetic procedures. This is particularly apparent from the different physical and chemical properties obtained for the resulting materials which clearly distinguish them from those known from the prior art, in particular in view of the surprisingly improved performance of the inventive catalysts compared to latter materials when used in SCR applications, which constitutes a highly important technical field in which CHA-type zeolitic materials are employed.

According to the present invention, it is preferred that in the inventive process, the mixture provided in step (1) does not contain any substantial amount of a source of $Z_2O_5$, wherein Z is P. Within the meaning of the present invention, the term "substantial" with respect to the amount of a source for $Z_2O_5$ being contained in the mixture provided in step (1) and crystallized in step (2) according to particular and preferred embodiments of the inventive process, this preferably indicates an amount of 5 wt.-% or less of $Z_2O_5$ contained in a source for $Z_2O_5$ and based on 100 wt-% of $YO_2$ contained in the one or more sources for $YO_2$, and more preferably indicates an amount of 1 wt.-% or less, more preferably of 0.5 wt.-% or less, more preferably of 0.1 wt.-% or less, more preferably of 0.05 wt.-% or less, more preferably of 0.01 wt.-% or less, more preferably of 0.005 wt.-% or less, more preferably of 0.001 wt.-% or less, more preferably of 0.0005 wt.-% or less, and even more preferably of 0.0001 wt.-% or less of $Z_2O_5$ contained in a source for $Z_2O_5$ based on 100 wt-% of $YO_2$ contained in the one or more sources for $YO_2$.

According to the present invention it is further preferred that Z stands for P and As, wherein more preferably Z is any pentavalent element which is a source for $Z_2O_5$ in the CHA-framework structure crystallized in step (2).

According to the invention process, one or more sources for $YO_2$ are provided in step (1), wherein said one or more sources may be provided in any conceivable form provided that a zeolitic material comprising $YO_2$ and $X_2O_3$ and having the CHA-type framework structure is crystallized in step (2). Preferably, $YO_2$ is provided as such and/or has a compound which comprises $YO_2$ as a chemical moiety and/or as a compound which (partly or entirely) is chemically transformed to $YO_2$ during the inventive process.

As regards $YO_2$ and/or precursors thereof employed in the inventive process, there is no particular restriction as to the one or more elements for which Y stands, provided that said element is a tetravalent element and that it is comprised in the zeolitic material crystallized in step (2). In particular, within the meaning of the present invention, $YO_2$ is at least partially and preferably entirely comprised in the framework structure of the zeolitic material as structure building element, as opposed to non-framework elements which can be present in the pores and cavities formed by the framework structure and typical for zeolitic materials in general. Thus, taking into account the aforementioned, Y may stand for any conceivable tetravalent element, Y standing either for a single or several tetravalent elements. Preferred tetravalent elements according to the present invention include Si, Sn, Ti, Zr, Ge, as well as combinations of any two or more thereof. According to preferred embodiments of the present invention, Y stands for Si and/or Sn, wherein according to particularly preferred embodiments of the present invention, Y comprises Si and even more preferably Y is Si.

In preferred embodiments of the present invention, wherein Y stands for Si or for a combination of Si with one or more further tetravalent elements, the source for $SiO_2$ preferably provided in step (1) can also be any conceivable source. Thus, by way of example, any type of silicas and/or silicates and/or silica derivatives may be used, wherein preferably the one or more sources for $YO_2$ comprises one or more compounds selected from the group consisting of fumed silica, silica hydrosols, reactive amorphous solid silicas, silica gel, silicic acid, water glass, sodium metasilicate hydrate, sesquisilicate, disilicate, colloidal silica, pyrogenic silica, silicic acid esters, or mixtures of any two or more of the afore-mentioned compounds may equally be used. According to particularly preferred embodiments, the one or more sources for $YO_2$ used in step (1) of the inventive process are selected from the group consisting of fumed silica, silica hydrosols, reactive amorphous solid silicas, silica gel, silicic acid, colloidal silica, silicic acid esters, and mixtures of two or more thereof. According to said particularly preferred embodiments, it is further preferred that the one or more sources for $YO_2$ are selected from the group consisting of fumed silica, silica hydrosols, reactive amorphous solid silicas, silica gel, colloidal silica, and mixtures of two or more thereof, wherein even more preferably according to the inventive process, the one or more sources for $YO_2$ comprises fumed silica and/or colloidal silica, preferably colloidal silica.

Regarding the one or more optionally substituted ethyltrimethylammonium cation-containing compounds provided in the mixture according to step (1) of the inventive process, there is no particular restriction as to the type and/or amount thereof provided that the type and/or amount thereof which is provided in step (1) allows for the crystallization of a zeolitic material having the CHA-type framework structure in step (2). According to preferred embodiments, the one or more optionally substituted ethyltrimethylammonium cation-containing compounds contain one or more salts. In principle, according to said preferred embodiments, there is no particular restriction as to the counter ion to the one or more optionally substituted ethyltrimethylammonium cations, again provided that these allow for the crystallization of a zeolitic material having a CHA-type framework structure in step (2) of the inventive process. Thus, by way of example, the one or more optionally substituted ethyltrimethylammonium cation-containing compounds may comprise one or more salts selected from halides, hydroxides, sulfates, nitrates, phosphates, acetates, and mixtures of two or more thereof. As regards the halide salts, these are preferably chloride and/or bromide salts, wherein even more preferably chloride salts are employed. According to preferred embodiments of the present invention, the one or more optionally substituted ethyltrimethylammonium cation-containing compounds comprise one or more of one or more salts selected from the group consisting of chlorides, hydroxides, sulfates, and mixtures of two or more thereof, wherein more preferably the one or more optionally substituted ethyltrimethylammonium cation-containing compounds are hydroxides and/or chlorides. According to particularly preferred embodiments, the one or more optionally substituted ethyltrimethylammonium cation-containing compounds are provided as their hydroxide salts in step (1) of the inventive process.

Thus, according to particularly preferred embodiments of the inventive process which are further preferred, the one or more optionally substituted ethyltrimethylammonium cation-containing compounds provided in step (1) comprise one or more optionally substituted ethyltrimethylammonium hydroxides, and even more preferably ethyltrimethylammonium hydroxide.

As regards the moieties by which the optionally substituted ethyltrimethylammonium-cation according to the present invention may be substituted, there is no particular restriction in this respect provided that a zeolitic material having a CHA-type framework structure may be crystallized in step (2). Thus, by way of example, the one or more optional substituents of the optionally substituted ethyltrimethylammonium-cation may be selected from the group consisting of $(C_1-C_3)$alkoxy, hydroxyl, halides, and combinations of two or more thereof, preferably from the group consisting of $(C_1-C_2)$alkoxy, hydroxyl, chloro, bromo, fluoro, and combinations of two or more thereof, more preferably from the group consisting of hydroxyl, chloro, and combinations thereof, wherein even more preferably the one or more optional substituents is hydroxo. As regards the number of substituents which are present on the optionally substituted ethyltrimethylammonium-cation according to particular embodiments of the present invention, their number may range anywhere from 1 to 4, wherein preferably from 1 to 3 substituents are present on the optionally substituted ethyltrimethylammonium-cation, more preferably 1 or 2, wherein even more preferably one substituent is present on the optionally substituted ethyltrimethylammonium-cation according to particular embodiments of the present invention. According to the present invention, it is however particularly preferred that the ethyltrimethylammonium-cation is unsubstituted.

Regarding the one or more tetraalkylammonium cations $R^1R^2R^3R^4N^+$ further provided in the mixture according to step (1) of the inventive process, there is no particular restriction as to the type and/or amount thereof provided that $R^1$, $R^2$, and $R^3$ independently from one another stand for alkyl and $R^4$ stands for a cycloalkyl moiety, provided that the type and/or amount thereof which is provided in step (1) allows for the crystallization of a zeolitic material having the CHA-type framework structure in step (2). Thus, regarding the alkyl moieties $R^1$, $R^2$, and $R^3$ of the one or more tetraalkylammonium cations $R^1R^2R^3R^4N^+$ provided in step (1) of the inventive process, these may, by way of example, independently from one another stand for optionally substituted and/or optionally branched $(C_1-C_6)$alkyl. According to the present invention, $R^1$, $R^2$, and $R^3$ may be the same, or two of $R^1$, $R^2$, and $R^3$ may be the same and one different from the others, or $R^1$, $R^2$, and $R^3$ may each be different from one another, wherein it is preferred that at least two of $R^1$, $R^2$, and $R^3$ are the same alkyl moiety, and wherein even more preferably $R^1$, $R^2$, and $R^3$ are the same alkyl moiety according to particular embodiments of the present invention. As regards preferred embodiments of the present invention, $R^1$, $R^2$, and $R^3$ independently from one another stand for optionally substituted and/or optionally branched $(C_1-C_5)$alkyl, wherein more preferably $R^1$, $R^2$, and $R^3$ are independently from one another selected from the group consisting of $(C_1-C_4)$alkyl, more preferably $(C_1-C_3)$alkyl, wherein even more preferably $R^1$. $R^2$, and $R^3$ independently form one another stand for optionally substituted methyl or ethyl. According to particularly preferred embodiments of the present invention, at least one, preferably two, and even more preferably all of $R^1$, $R^2$, and $R^3$ stand for optionally substituted methyl, preferably for unsubstituted methyl.

Therefore, as concerns the one or more tetraalkylammonium cations $R^1R^2R^3R^4N^+$ further provided in the mixture according to step (1) of the inventive process, it is preferred according to the present invention that $R^1$, $R^2$, and $R^3$ independently from one another stand for optionally substituted and/or optionally branched $(C_1-C_3)$alkyl, preferably $(C_1-C_5)$alkyl, more preferably $(C_1-C_4)$alkyl, more preferably $(C_1-C_3)$alkyl, and even more preferably for optionally substituted methyl or ethyl, wherein even more preferably $R^1$, $R^2$, and $R^3$ stand for optionally substituted methyl, preferably unsubstituted methyl.

As regards the cycloalkyl moiety $R^4$ of the one or more tetraalkylammonium cations $R^1R^2R^3R^4N^+$ provided in step (1) of the inventive process, $R^4$ may stand for any suitable cycloalkyl group and is preferably cycloalkyl selected from the group consisting optionally heterocyclic and/or optionally substituted cycloalkyl. As regards the number of chain members forming the optionally heterocyclic cycloalkyl moiety, no particular restriction applies in this respect according to the present invention, provided that a zeolitic material having a CHA-type framework structure may be crystallized in step (2) of the inventive process. Thus, by way of example, the optionally heterocyclic cycloalkyl moiety may be formed from any suitable number of chain members, wherein it is preferred that the ring moiety is formed from optionally heterocyclic 5- to 8-membered cycloalkyl, more preferably 5- to 7-membered cycloalkyl, more preferably 5- or 6-membered cycloalkyl, wherein even more preferably the optionally heterocyclic cycloalkyl is a 6-membered cycloalkyl. As regards the moieties by which the optionally heterocyclic cycloalkyl moieties according to the present invention may be substituted, there is again no particular restriction in this respect provided that a zeolitic material having a CHA-type framework structure may be crystallized in step (2). Thus, by way of example, the one or more optional substituents of the optionally heterocyclic moiety may be selected from the group consisting of $(C_1-C_3)$alkyl, $(C_1-C_3)$alkoxy, hydroxyl, halides, $(C_1-C_3)$carboxyl, $(C_1-C_3)$carbonyl, $(C_1-C_3)$amine and combinations of two or more thereof, preferably from the group consisting of $(C_1-C_2)$alkyl, $(C_1-C_2)$alkoxy, hydroxyl, chloro, bromo, fluoro, and combinations of two or more thereof, more preferably from the group consisting of methyl, hydroxyl, chloro, and combinations of two or more thereof, wherein even more preferably the one or more optional substituents is methyl and/or hydroxo, preferably methyl. As regards the number of substituents which are present on the optionally heterocyclic cycloalkyl moiety according to particular embodiments of the present invention, their number may range anywhere from 1 to 4, wherein preferably from 1 to 3 substituents are present on the optionally heterocyclic cycloalky, more preferably 1 or 2, wherein even more preferably one substituent is present on the optionally heterocylic cycloalkyl moiety of $R^4$ according to particular embodiments of the present invention. According to the present invention, it is however particularly preferred that $R^4$ stands for optionally heterocyclic cycloalkyl which is unsubstituted, and even more preferably for cyclohexyl.

Regarding the heteroatom which may be present in embodiments of the present invention wherein $R^4$ is an optionally substituted heterocyclic cycloalkyl, no particular restriction applies according to the present invention, neither with respect to the type of heteroatoms which may be present in the heterocyclic cycloalkyl moiety, nor with respect to their number, provided that a zeolitic material having the CHA-type framework structure may be crystallized in step (2). Thus, by way of example, the one or more heteroatoms comprised in the heterocyclic cycloalkyl may comprise one or more elements selected from the group consisting of N, O, S, Se, P, Cl, Br, I, and combinations of two or more thereof, wherein preferably the one or more heteroatoms comprise one or more elements selected from the group consisting of N, O, S, Se, P, and combinations of two or more thereof, more preferably from the group consisting of N, O, S, and combinations of two or three thereof, wherein even more preferably the one or more heteroatoms comprise N and/or O, preferably O. As regards the number of heteroatoms which are contained as chain members of the heterocyclic cycloalkyl according to particular embodiments of the present invention, their number may range anywhere from 1 to 4, wherein preferably from 1 to 3 heteroatoms are present in the heterocyclic cycloalky, more preferably 1 or 2, wherein even more preferably one heteroatom is contained in the heterocylic cycloalkyl moiety of $R^4$ according to particular embodiments of the present invention. It is, however, particularly preferred according to the present invention that the cycloalkyl moiety $R^4$ of the one or more tetraalkylammonium cation $R^1R^2R^3R^4N^+$-containing compounds provided in step (1) of the inventive process is cycloalkyl which does not contain a heteroatom, preferably cyclohexyl.

Therefore, as concerns the one or more tetraalkylammonium cations $R^1R^2R^3R^4N^+$ further provided in the mixture according to step (1) of the inventive process, it is preferred according to the present invention that $R^4$ stands for optionally heterocyclic and/or optionally substituted 5- to 8-membered cycloalkyl, preferably for 5- to 7-membered cycloalkyl, more preferably for 5- or 6-membered cycloalkyl, wherein even more preferably $R^4$ stands for optionally heterocyclic and/or optionally substituted 6-membered cycloalkyl, preferably optionally substituted cyclohexyl, and more preferably non-substituted cyclohexyl.

Furthermore, according to particularly preferred embodiments of the inventive process, the one or more tetraalkylammonium cation $R^1R^2R^3R^4N^+$-containing compounds comprise one or more N,N,N-tri$(C_1-C_4)$alkyl-$(C_5-C_7)$cycloalkylammonium compounds, preferably one or more N,N,N-tri$(C_1-C_3)$alkyl-$(C_5-C_6)$cycloalkylammonium compounds, more preferably one or more N,N,N-tri$(C_1-C_2)$alkyl-$(C_5-C_6)$cycloalkylammonium compounds, more preferably one or more N,N,N-tri$(C_1-C_2)$alkyl-cyclopentylammonium and/or one or more N, N, N-tri$(C_1-C_2)$alkylcyclohexylammonium compounds, more preferably one or more compounds selected from N,N,N-triethyl-cyclohexylammonium, N,N-diethyl-N-methyl-cyclohexylammonium, N,N-dimethyl-N-ethyl-cyclohexylammonium, N,N,N-trimethyl-cyclohexylammonium compounds, and mixtures of two or more thereof, wherein it is even more preferred according to the inventive process that the one or more tetraalkylammonium cation $R^1R^2R^3R^4N^+$-containing compounds comprise one or more N,N,N-trimethyl-cyclohexylammonium compounds, wherein it is even further preferred that the one or more tetraalkylammonium cation $R^1R^2R^3R^4N^+$-containing compounds provided in step (1) of the inventive process consists of one or more N,N,N-trimethyl-cyclohexylammonium compounds, even more preferably of a single N,N,N-trimethyl-cyclohexylammonium compound.

According to the present invention, there is no particular restriction as to the type of the one or more tetraalkylammonium cations $R^1R^2R^3R^4N^+$-containing compounds which may be provided in step (1) of the inventive process provided that the one or more tetraalkylammonium cations $R^1R^2R^3R^4N^+$ contained therein may act as structure directing agent upon crystallization of the reaction mixture in step (2) of the inventive process. According to preferred embodiments, the one or more tetraalkylammonium cations $R^1R^2R^3R^4N$-containing compounds contain one or more salts. In principle, according to said preferred embodiments, there is no particular restriction as to the counter ion to the one or more tetraalkylammonium cations $R^1R^2R^3R^4N^+$, again provided that these allow for the crystallization of a zeolitic material having a CHA-type framework structure in step (2) of the inventive process by the structure directing action of one or more of the aforementioned tetraalkylammonium cations $R^1R^2R^3R^4N^+$. Thus, by way of example, the one or more tetraalkylammonium cation $R^1R^2R^3R^4N^+$-containing compounds may comprise one or more salts selected from halides, hydroxides, sulfates, nitrates, phosphates, acetates, and mixtures of two or more thereof. As regards the halide salts, these are preferably chloride and/or bromide salts, wherein even more preferably chloride salts are employed. According to preferred embodiments of the present invention, the one or more tetraalkylammonium cation $R^1R^2R^3R^4N^+$-containing compounds comprise one or more one of more salts selected from the group consisting of chlorides, hydroxides, sulfates, and mixtures of two or more thereof, wherein more preferably the one or more tetraalkylammonium cation $R^1R^2R^3R^4N^+$-containing compounds are tetraalkylammonium hydroxides and/or chlorides. According to particularly preferred embodiments, the one or more tetraalkylammonium cations $R^1R^2R^3R^4N'$-containing compounds are provided as their hydroxide salts in step (1) of the inventive process.

Thus, according to particularly preferred embodiments of the inventive process which are further preferred, the one or more tetraalkylammonium cation $R^1R^2R^3R^4N^+$-containing compounds provided in step (1) comprise one or more compounds selected from the group consisting of N,N,N-tri($C_1$-$C_4$)alkyl-($C_5$-$C_7$)cycloalkylammonium hydroxides, preferably of N,N,N-tri($C_1$-$C_3$)alkyl-($C_5$-$C_7$)cycloalkylammonium hydroxides, more preferably of N,N,N-tri($C_1$-$C_2$)alkyl-($C_5$-$C_6$)cycloalkylammonium hydroxides, more preferably of N,N,N-tri($C_1$-$C_2$)alkyl-cyclopentylammonium and/or N,N,N-tri($C_1$-$C_2$)alkyl-cyclohexylammonium hydroxides, wherein it is yet further preferred that the one or more tetraalkylammonium cation $R^1R^2R^3R^4N^+$-containing compounds is selected from the group consisting of N,N,N-triethyl-cyclohexylammonium hydroxide, N, N-diethyl-N-methyl-cyclohexylammonium hydroxide, N,N-dimethyl-N-ethyl-cyclohexylammonium hydroxide, N,N,N-trimethyl-cyclohexylammonium hydroxide, and mixtures of two or more thereof. According to embodiments of the present invention which are even further preferred, the one or more tetraalkylammonium cation $R^1R^2R^3R^4N^+$-containing compounds comprise N,N,N-trimethyl-cyclohexylammonium hydroxide, wherein even more preferably the tetraalkylammonium cation $R^1R^2R^3R^4N^+$-containing compound provided in step (1) is N,N,N-trimethyl-cyclohexylammonium hydroxide.

According to the present invention the mixture provided in step (1) further comprises one or more sources for $X_2O_3$, wherein X is a trivalent element. As regards the elements which may be employed as the trivalent element X comprised in the one or more sources for $X_2O_3$ provided in step (1), there is no particular restriction according to the present invention as to which elements or element mixtures may be employed, provided that a zeolitic material having a CHA-type framework structure is crystallized in step (2) comprising $YO_2$ and $X_2O_3$ as framework elements. According to preferred embodiments of the present invention, X is selected from the group consisting of Al, B, In, Ga, and mixtures of two or more thereof, wherein preferably X is Al and/or B. According to particularly preferred embodiments of the present invention, X comprises Al, wherein even more preferably X is Al.

According to the present invention, the mixture provided in step (1) comprises one or more sources for $X_2O_3$. In instances wherein one or more sources of $Al_2O_3$ is contained in the mixture, it is preferred that said one or more sources comprises one or more compounds selected from the group consisting of alumina, aluminates, aluminum salts, and mixtures of two or more thereof, wherein the aluminates are preferably one or more aluminate salts selected from the group consisting of alkaline metal aluminates, aluminum hydroxide, and mixtures of two or more thereof, the alkaline metal preferably being sodium and/or potassium, and more preferably being sodium. According to the present invention it is further preferred that the one or more sources or $X_2O_3$ comprise one or more compounds selected from the group consisting of alumina, aluminum salts, and mixtures of two or more thereof, wherein more preferably the one or more sources for $X_2O_3$ are selected from the group consisting of alumina, aluminum tri($C_1$-$C_5$)alkoxide, AlO(OH), Al(OH)$_3$, aluminum halides, and mixtures of two or more thereof, wherein the aluminum halides are preferably aluminum chloride and/or chloride and/or bromide, more preferably aluminum fluoride and/or chloride, and even more preferably aluminum chloride. It is yet further preferred that the one or more sources for $X_2O_3$ comprise one or more compounds selected from the group consisting of aluminum chloride, aluminum sulfate, aluminum phosphate, aluminum fluorosilicate, and mixtures of two or more thereof, wherein more preferably the one or more sources for $X_2O_3$ comprise one or more compounds selected from the group consisting of aluminum tri($C_2$-$C_4$)alkoxide, AlO(OH), Al(OH)$_3$, aluminum chloride, aluminum sulfate, aluminum phosphate, and mixtures of two or more thereof. It is particularly preferred according to the present invention that the one or more sources for $X_2O_3$ comprise one or more compounds selected from the group consisting of aluminum tri($C_2$-$C_3$) alkoxide, AlO(OH), Al(OH)$_3$, aluminum chloride, aluminum sulfate, and mixtures of two or more thereof, more preferably from the group consisting of aluminum tripropoxides, AlO(OH), aluminum sulfate, and mixtures of two or more thereof, wherein more preferably the one or more sources for $X_2O_3$ comprises aluminum triisopropoxide, and wherein even more preferably the one or more sources for $X_2O_3$ consists of aluminum triisopropoxide.

In step (1) according to the present invention, the mixture can be prepared by any conceivable means, wherein mixing by agitation is preferred, preferably by means of stirring.

In preferred embodiments of the inventive process, the mixture provided in step (1) further comprises one or more solvents. According to the inventive process, there is no particular restriction whatsoever neither with respect to the type and/or number of the one or more solvents, nor with respect to the amount in which they may be used in the inventive process provided that a zeolitic material having the CHA-type framework structure may be crystallized in step (2). According to the inventive process it is however preferred that the one or more solvents comprise water, and more preferably distilled water, wherein according to particularly preferred embodiments distilled water is used as the only solvent in the mixture provided in step (1).

In preferred embodiments of the inventive process wherein one or more solvents are employed, there is no particular restriction as to the amount in which they may be used, wherein in particularly preferred embodiments employing water and more preferably distilled water, the H$_2$O:YO$_2$ molar ratio of the mixture may range by way of example anywhere from 1 to 40, wherein preferably the molar ratio employed is comprised in the range of from 3 to 30, more preferably of from 5 to 25, more preferably of from 8 to 20, more preferably of from 10 to 17, more preferably of from 11 to 15, and even more preferably of from 11.5 to 13. According to particularly preferred embodiments of the present invention wherein water and preferably distilled water is comprised among the one or more solvents provided in step (1) and even more preferably is the sole solvent used in the reaction mixture crystallized in step (2), the H$_2$O:YO$_2$ molar ratio is comprised in the range of from 12 to 12.5.

As regards the amount in which the one or more optionally substituted ethyltrimethylammonium cations may be provided in the mixture in step (1) of the inventive process, no particular restriction applies provided that a zeolitic material having a CHA-type framework structure may be crystallized in step (2) of the inventive process. Thus, by way of example, the molar ratio of the one or more optionally substituted ethyltrimethylammonium cations C$_2$H$_5$N(CH$_3$)$_3$N$^+$:YO$_2$ provided in the mixture may range anywhere from 0.005 to 0.5, wherein preferably the molar ratio is comprised in the range of from 0.01 to 0.25, more preferably from 0.03 to 0.2, more preferably from 0.05 to 0.15, more preferably from 0.07 to 0.12, and more preferably from 0.08 to 0.11. According to particularly preferred embodiments of the present invention, the molar ratio of the one or more tetraalkylammonium cations C$_2$H$_5$N(CH$_3$)$_3$N$^+$:YO$_2$ provided in the mixture according to step (1) is comprised in the range of from 0.085 to 0.095.

Same applies accordingly relative to the amount in which the one or more tetraalkylammonium cations R$^1$R$^2$R$^3$R$^4$N$^+$ may be provided in the mixture in step (1) of the inventive process, such that no particular restriction applies in this respect as well, provided that a zeolitic material having a CHA-type framework structure may be crystallized in step (2) of the inventive process.

Thus, by way of example, the molar ratio of the one or more tetraalkylammonium cations R$^1$R$^2$R$^3$R$^4$N$^+$:YO$_2$ provided in the mixture may range anywhere from 0.001 to 2.0, wherein preferably the molar ratio is comprised in the range of from 0.005 to 1.0, more preferably from 0.01 to 0.5, more preferably from 0.03 to 0.3, more preferably from 0.05 to 0.25, more preferably from 0.08 to 0.22, more preferably from 0.01 to 0.2, more preferably from 0.12 to 0.18, and more preferably from 0.13 to 0.17. According to particularly preferred embodiments of the present invention, the molar ratio of the one or more tetraalkylammonium cations R$^1$R$^2$R$^3$R$^4$N$^+$:YO$_2$ provided in the mixture according to step (1) is comprised in the range of from 0.14 to 0.16.

Concerning the relative amounts of the one or more tetraalkylammonium cations C$_2$H$_5$N(CH$_3$)$_3$N$^+$ and R$^1$R$^2$R$^3$R$^4$N$^+$ to one another, these may be used in any suitable relation to one another provided that a CHA-type framework structure may be crystallized in step (2) of the inventive process. Thus, with respect to the molar ratio C$_2$H$_5$N(CH$_3$)$_3$N$^+$:R$^1$R$^2$R$^3$R$^4$N$^+$ of the one or more tetraalkylammonium cations C$_2$H$_5$N(CH$_3$)$_3$N$^+$ and the one or more tetraalkylammonium cations R$^1$R$^2$R$^3$R$^4$N contained in the mixture provided according to step (1), no particular restriction applies such that, by way of example, the molar ratio C$_2$H$_5$N(CH$_3$)$_3$N$^+$:R$^1$R$^2$R$^3$R$^4$N$^+$ may range anywhere from 0.01 to 5, wherein preferably the molar ratio is comprised in the range of from 0.05 to 2, more preferably from 0.1 to 1.5, more preferably from 0.2 to 1.2, more preferably from 0.3 to 1, more preferably from 0.4 to 0.8, and more preferably from 0.5 to 0.7. According to the present invention, it is particularly preferred that the molar ratio C$_2$H$_5$N(CH$_3$)$_3$N$^+$:R$^1$R$^2$R$^3$R$^4$N$^+$ in the mixture provided according to step (1) is comprised in the range of from 0.55 to 0.65.

As regards the crystallization performed in step (2) of the inventive process, no particular restriction applies according to the present invention as to the actual means employed for allowing the crystallization of a zeolitic material from the mixture of step (1). Thus, any suitable means may be employed wherein it is preferred that the crystallization is achieved by heating of the mixture of step (1). According to said preferred embodiments, no particular restriction again applies with respect to the temperature at which said crystallization may be achieved, wherein it is preferred that the crystallization is conducted under heating at a temperature comprised in the range of from 90 to 250° C., more preferably of from 100 to 220° C., more preferably from 130 to 200° C., more preferably from 150 to 190° C., and more preferably from 160 to 180° C. According to the present invention it is particularly preferred that the preferred heating of the mixture provided in step (1) in step (2) for the crystallization of a zeolitic material is conducted at a temperature comprised in the range of from 165 to 175° C.

Concerning the heating preferably employed in step (2) of the inventive process as means for the crystallization of the zeolitic material, said heating may in principle be conducted under any suitable pressure provided that crystallization is achieved. In preferred embodiments of the present invention, the mixture according to step (1) is subjected in step (2) to a pressure which is elevated with regard to normal pressure. The term "normal pressure" as used in the context of the present invention relates to a pressure of 101,325 Pa in the ideal case. However, this pressure may vary within boundaries known to the person skilled in the art. By way of example, this pressure can be in the range of from 95,000 to 106,000 or from 96,000 to 105,000 or of from 97,000 to 104,000 or from 98,000 to 103,000 or of from 99,000 to 102,000 Pa.

In preferred embodiments of the inventive process wherein a solvent is present in the mixture according to step (1), it is furthermore preferred that heating in step (2) is conducted under solvothermal conditions, meaning that the mixture is crystallized under autogenous pressure of the solvent which is used, for example by conducting heating in an autoclave or other crystallization vessel suited for generating solvothermal conditions. In particularly preferred embodiments wherein the solvent comprises water, preferably distilled water, heating in step (2) is accordingly preferably conducted under hydrothermal conditions.

The apparatus which can be used in the present invention for crystallization is not particularly restricted, provided that the desired parameters for the crystallization process can be realized, in particular with respect to the preferred embodiments requiring particular crystallization conditions. In the preferred embodiments conducted under solvothermal conditions, and in particular under hydrothermal conditions, any type of autoclave or digestion vessel can be used.

Furthermore, as regards the period in which the preferred heating in step (2) of the inventive process is conducted for crystallizing the zeolitic material, there is again no particular restriction in this respect, provided that the period of heating is suitable for achieving crystallization. Thus, by way of example, the period of heating may range anywhere from 3 to 120 h, preferably from 5 to 72 h, more preferably from 8 to 48 h, more preferably from 12 to 36 h, and more preferably from 16 to 32 h. According to the present invention it is particularly preferred that heating in step (2) of the inventive process is conducted for a period of from 20 to 28 h.

According to preferred embodiments of the present invention, wherein the mixture is heated in step (2), said heating may be conducted during the entire crystallization process or during only one or more portions thereof, provided that a zeolitic material is crystallized. Preferably, heating is conducted during the entire duration of crystallization.

Further regarding the means of crystallization in step (2) of the inventive process, it is principally possible according to the present invention to perform said crystallization either under static conditions or by means of agitating the mixture. According to embodiments involving the agitation of the mixture, there is no particular restriction as to the means by which said agitation may be performed such that any one of vibrational means, rotation of the reaction vessel, and/or mechanical stirring of the reaction mixture may be employed to this effect wherein according to said embodiments it is preferred that agitation is achieved by stirring of the reaction mixture. According to alternatively preferred embodiments, however, crystallization is performed under static conditions, i.e. in the absence of any particular means of agitation during the crystallization process.

In general, the process of the present invention can optionally comprise further steps for the work-up and/or further physical and/or chemical transformation of the zeolitic material crystallized in step (2) from the mixture provided in step (1). The crystallized material can for example be subject to any sequence of isolation and/or washing procedures, wherein the zeolitic material obtained from crystallization in step (2) is preferably subject to at least one isolation and at least one washing procedure.

Isolation of the crystallized product can be achieved by any conceivable means. Preferably, isolation of the crystallized product can be achieved by means of filtration, ultra-filtration, diafiltration, centrifugation and/or decantation methods, wherein filtration methods can involve suction and/or pressure filtration steps.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent.

Preferably, the separated zeolitic material is washed until the pH of the washing agent, preferably the washwater, is in the range of from 6 to 8, preferably from 6.5 to 7.5.

Furthermore, the inventive process can optionally comprise one or more drying steps. In general, any conceivable means of drying can be used. Drying procedures preferably include heating and/or applying vacuum to the zeolitic material. In envisaged embodiments of the present invention, one or more drying steps may involve spray drying, preferably spray granulation, of the zeolitic material.

In embodiments which comprise at least one drying step, the drying temperatures are preferably in the range of from 25° C. to 150° C., more preferably of from 60 to 140° C., more preferably of from 70 to 130° C. and even more preferably in the range of from 75 to 125° C. The durations of drying are preferably in the range of from 2 to 48 h, more preferably in the range of 4 to 36 hours, more preferably of from 6 to 24 h, and even more preferably of from 8 to 12 h.

In general, the optional washing and/or isolation and/or ion-exchange procedures comprised in the inventive process can be conducted in any conceivable order and repeated as often as desired.

Therefore, according to preferred embodiments of the present invention, the process for the preparation of a zeolitic material further comprises one or more of the following steps of (3) adjusting the pH of the crystallized mixture obtained in (2), preferably to a pH ranging from 3 to 11, more preferably from 4 to 10, more preferably from 5 to 9, more preferably from 6 to 8, and more preferably from 6.5 to 7.5, and/or (4) isolating the zeolitic material from the crystallized mixture in (2) or (3), preferably by filtration, and/or (5) washing the zeolitic material obtained in (2), (3), or (4), and/or (6) drying and/or calcining the zeolitic material obtained in (2), (3), (4), or (5), and/or (7) subjecting the zeolitic material to an ion-exchange procedure, wherein the steps (3) and/or (4) and/or (5) and/or (6) and/or (7) can be conducted in any order, and wherein one or more of said steps is preferably repeated one or more times.

As regards the adjustment of the pH in step (3) of particular and preferred embodiments of the inventive process, it is preferred according to the present invention that said step is performed with the direct product from crystallization in step (2), wherein no portion of the immediate reaction product from crystallization has been subject to any intermediate treatment and/or separation step of any sort. Accordingly it is preferred according to the present invention that step (3) is performed on the direct reaction product obtained from crystallization in step (2) of the inventive process.

With respect to the calcination of the zeolitic material according to (6) after optional isolation, washing and/or drying thereof, no particular restriction applies such that in principle said calcination may be conducted at any suitable temperature and for any suitable duration. Thus, by way of example, the calcination may be conducted at a temperature in the range of from 400 to 850° C., wherein preferably, the calcination is conducted at a temperature ranging from 450 to 700° C., more preferably from 500 to 600° C., and more preferably from 525 to 575° C. Furthermore, the duration of the calcination may range anywhere from 2 to 48 h, wherein the calcination is preferably conducted for a period ranging from 3 to 24 h, more preferably from 4 to 12 h, more preferably from 4.5 to 8 h, and more preferably from 5 to 6 h. According to the inventive process it is particularly preferred that calcination of the zeolitic material according to (6) is conducted at a temperature in the range of from 400 to 850° C. for 2 to 48 h, more preferably at a temperature in the range of from 450 to 700° C. for 3 to 24 h, more preferably at a temperature in the range of from 500 to 600° C. or 4 to 12 h, more preferably at a temperature in the range of from 525 to 575° C. for 4.5 to 8 h, and more preferably at a temperature in the range of from 525 to 575° C. for 5 to 6 h.

According to the present invention it is however preferred that in step (6) the zeolitic material is spray dried, wherein more preferably the zeolitic material obtained in step (2) is not subject to any step of isolation according to (4) and/or of washing according to (5) prior to being subject to spray drying in (6). According to the inventive process it is yet further preferred that the reaction product obtained in step (2) is directly subject to spray drying in step (6), wherein according to the meaning of the present invention, the preferred direct spray drying of the reaction product in step (2) means that the reaction product is not subject to any intermediate treatment and/or separation step prior to step (6), wherein more preferably the direct reaction product obtained in step (2) is neither subject to an intermediate treatment step of any kind, nor are any components added or removed from the crystallized mixture obtained in step (2) prior to being subject to spray drying in step (6).

Thus, according to the inventive process, the zeolitic material crystallized in step (2) can optionally be subject to at least one step of an ion-exchange procedure, wherein the term "ion-exchange" according to the present invention generally refers to non-framework ionic elements and/or molecules contained in the zeolitic material which are accordingly exchanged by other ions, which are generally provided from an external source. Preferably, the non-framework ionic element comprises one or more of the one or more alkali metals M preferably comprised in the zeolitic material having a CHA-type framework structure crystallized in step (2), more preferably Na and/or K, and even more preferably Na.

In general, any conceivable ion-exchange procedure with all possible ionic elements and/or molecules can be conducted on the zeolitic material. Preferably, as ionic elements at least one cation and/or cationic element is employed which is preferably selected from the group consisting of $H^+$, $NH_4^+$, Sr, Zr, Cr, Mg, Mo, Fe, Co, Ni, Cu, Zn, Ru, Rh, Pd, Ag, Os, Ir, Pt, Au, and mixtures of two or more thereof, more preferably from the group consisting of $H^+$, $NH_4^+$, Sr, Cr, Mo, Fe, Co, Ni, Cu, Zn, Ag, and mixtures of two or more thereof, more preferably from the group consisting of $H^+$, $NH_4^+$, Cr, Mg, Mo, Fe, Ni, Cu, Zn, Ag, and mixtures of two or more thereof. According to particularly preferred embodiments of the present invention, the one or more cations and/or cationic elements are selected from the group consisting of Mg, Mo, Fe, Ni, Cu, Zn, Ag, and mixtures of two or more thereof, wherein more preferably the one or more cation and/or cationic elements comprise Cu and/or Fe, preferably Cu, wherein even more preferably the one or more cation and/or cationic elements consist of Cu and/or Fe, preferably of Cu. Preferably, the zeolitic material is first ion-exchanged with $H^+$ and/or $NH_4^+$, and more preferably with $NH_4^+$, before being subject to a further ion-exchange procedure, more preferably before being subject to ion-exchange with at least one cation and/or cationic element selected from the group consisting of Sr, Zr, Cr, Mg, Mo, Fe, Co, Ni, Cu, Zn, Ru, Rh, Pd, Ag, Os, Ir, Pt, Au, and mixtures of two or more thereof, more preferably from the group consisting of Sr, Cr, Mo, Fe, Co, Ni, Cu, Zn, Ag, and mixtures of two or more thereof, more preferably from the group consisting of Cr, Mg, Mo, Fe, Ni, Cu, Zn, Ag, and mixtures of two or more thereof, more preferably from the group consisting of Mg, Mo, Fe, Ni, Cu, Zn, Ag, and mixtures of two or more thereof, wherein more preferably the zeolitic material is first ion-exchanged with one or more cation and/or cationic elements comprising Cu and/or Fe, preferably Cu, wherein more preferably the one or more cation and/or cationic elements consist of Cu and/or Fe, preferably of Cu. As regards preferred embodiments of the present invention wherein the zeolitic material is first ion-exchanged with an $NH_4^+$ before being subject to a further ion-exchange procedure, this may also be achieved by transformation of $H^+$ ions already contained in the zeolitic material into $NH_4$ ions by appropriate treatment with ammonia or any precursor compound thereof. As regards the one or more ionic non-framework elements which are ion-exchanged, there is no particular restriction according to the present invention as to which ionic non-framework elements present in the zeolitic material may be ion-exchanged according to the aforementioned preferred embodiments, wherein preferably the one or more ionic non-framework elements to be exchanged comprise $H^+$ and/or an alkali metal, the alkali metal preferably being selected from the group consisting of Li, Na, K, Cs, and combinations of two or more thereof, more preferably from the group consisting of Li, Na, K, and combinations of two or more thereof, wherein more preferably the alkali metal is Na and/or K, and even more preferably Na.

In general, the zeolitic material obtained according to the inventive process may be any conceivable zeolitic material, wherein preferably said zeolitic material formed in step (2) comprises one or more zeolites having the CHA-type framework structure. Among the preferred zeolitic materials comprising one or more zeolites having the CHA-type framework structure, there is no particular restriction neither with respect to the type and/or number thereof, nor with respect to the amount thereof in the zeolitic material. According to preferred embodiments of the present invention, the one or more zeolites having the CHA framework structure comprise one or more zeolites selected from the group consisting of $(Ni(deta)_2)$-UT-6, Chabazite, |Li-Na| [Al—Si—O]-CHA, DAF-5, Dehyd. Na-Chabazite, K-Chabazite, LZ-218, Linde D, Linde R, Phi, SSZ-62, UiO-21, Willhendersonite, ZK-14, ZYT-6, and mixtures of two or more thereof, more preferably from the group consisting of $(Ni(deta)_2)$-UT-6, Chabazite, |Li-Na| [Al—Si—O]-CHA, DAF-5, Dehyd. Na-Chabazite, K-Chabazite (Iran), LZ-218, Linde D, Linde R, Phi, SSZ-62, UiO-21, Willhendersonite, ZK-14, ZYT-6, and combinations of two or more thereof, wherein even more preferably the zeolitic material formed in step (2) comprises Chabazite.

According to the inventive process, it is particularly preferred that the mixture provided in step (1) and crystallized in step (2) at no point contains any substantial amount of an organic structure directing agent other than the one or more tetraalkylammonium cation $R^1R^2R^3R^4N^+$ containing compounds according to any of the particular and preferred embodiments of the present invention, wherein such organic structure directing agents other than the tetraalkylammonium compounds used in the inventive process preferably designate any other conceivable organotemplates which may suitably be used in the synthesis of zeolitic materials having a CHA-type framework structure either by themselves, or in combination with the one or more tetraalkylammonium cation $R^1R^2R^3R^4N^+$-containing compounds according to the present invention. According to a preferred meaning of the present invention, the organic structure directing agent other than the one or more tetraalkylammonium cation $R^1R^2R^3R^4N^+$-containing compounds designates any one or more compounds selected from dialkyl amines, and/or heterocyclic amines, including any combination of two or more thereof, wherein preferably said one or more other organic structure directing agent is selected from the group consisting of di($C_1$-$C_5$)alkyl amines, oxygen containing heterocyclic amines with 5 to 8 ring members, and combinations of two or more thereof, more preferably from the group consisting of di($C_2$-$C_4$)alkyl amines, oxygen containing heterocyclic amines with 5 to 7 ring members, and combinations of two or more thereof, more preferably from the group consisting of di($C_2$-$C_3$)alkyl amines, oxygen containing heterocyclic amines with 5 or 6 ring members, and combinations of two or more thereof, and/or related organotemplates such as any suitable N-alkyl-3-quinuclidinol compound, N,N,N-trialkyl-exoaminonorbornane compound, N,N,N-trimethyl-1-adamantylammonium compound, N,N,N-trimethyl-2-adamantylammonium compound, N,N,N-trimethylcyclohexylammonium compound, N,N-dimethyl-3,3-dimethylpiperidinium compound, N,N-methylethyl-3,3-dimethylpiperidinium compound, N,N-dimethyl-2-methylpiperidinium compound, 1,3,3,6,6-pentamethyl-6-azonio-bicyclo(3.2.1)octane compound, N,N-dimethylcyclohexylamine compound, or any suitable N,N,N-trimethylbenzylammonium compound, including combinations of two or more thereof. According to particularly preferred embodiments of the present invention, the mixture provided in step (1) does not contain any substantial amount of a trimethyl benzyl ammonium containing compound, and preferably not any substantial amount of a trialkyl benzyl ammonium compound, wherein even more preferably the mixture provided in step (1) only contains one or more N,N,N-trimethyl-cyclohexylammonium compounds and preferably N,N,N-trimethyl-cyclohexylammonium hydroxide as structure directing agent for the crystallization of a zeolitic material having a CHA-type framework structure in step (2).

Therefore, it is preferred according to the present invention that the mixture provided in step (1) does not contain any substantial amount of a trimethyl benzyl ammonium containing compound, preferably of a trialkyl benzyl ammonium compound wherein preferably the mixture provided in step (1) does not contain any substantial amount of an organotemplate other than the one or more tetraalkylammonium cation $R^1R^2R^3R^4N^+$-containing compounds as structure directing agent, wherein more preferably the mixture provided in step (1) does not contain any substantial amount of a structure directing agent other than the one or more tetraalkylammonium cation $R^1R^2R^3R^4N^+$-containing compounds, and wherein even more preferably, the mixture provided in step (1) only contains one or more N,N,N-trimethyl-cyclohexylammonium compounds and preferably N,N,N-trimethyl-cyclohexylammonium hydroxide as structure directing agent for the crystallization of a zeolitic material having a CHA-type framework structure in step (2).

According to specific embodiments of the present invention, not more than an impurity of said one or more other organic structure directing agent may, however, be present in the reaction mixture, for example, as a result of said one or more other organic structure directing agents still being present in seed crystals preferably used in the inventive process. Such other organotemplates contained in seed crystal material may not, however, participate in the crystallization process since they are trapped within the seed crystal framework and therefore may not act structure directing agents within the meaning of the present invention.

Within the meaning of the present invention, the term "substantially" as employed in the present application with respect to the amount of any one or more organotemplate other than the one or more tetraalkylammonium cation $R^1R^2R^3R^4N^+$-containing compounds as structure directing agent contained in the mixture provided in step (1) indicates an amount of 0.1 wt.-% or less of the total amount of any other one or more organotemplate, preferably 0.05 wt.-% or less, more preferably 0.001 wt.-% or less, more preferably 0.0005 wt.-% or less, and even more preferably 0.0001 wt.-% or less thereof. Said amounts of one or more other organotemplates, if at all present an any one of the materials used in the synthetic process, may also be denoted as "impurities" or "trace amounts" within the meaning of the present invention. Furthermore, it is noted that the terms "organotemplate" and "organic structure directing agent" are synonymously used in the present application.

According to the process of the present invention, seed crystals may optionally be provided in step (1), wherein said seed crystals preferably comprise a zeolitic material of the same type of framework structure as obtained from crystallization in step (2), wherein more preferably the seed crystals comprise a zeolitic material as obtained according to the inventive process. According to particularly preferred embodiments, the seed crystals comprise one or more zeolitic materials having a CHA-type framework structure. According to said preferred embodiments, the seed crystals may comprise any zeolitic material having a CHA-type framework structure, provided that a zeolitic material is crystallized in step (2), which is preferably a zeolitic material having the CHA-type framework structure, wherein more preferably the zeolitic material having a CHA-type framework structure comprised in the seed crystals is a zeolitic material obtained according to the inventive process, and wherein even more preferably the zeolitic material having a CHA-type framework structure comprised in the seed crystals is the same as the zeolitic material having a CHA-type framework structure which is then crystallized in step (2). Particularly preferred according to the present invention are seed crystals comprising one or more zeolites selected from the group consisting of (Ni(deta)$_2$)-UT-6, Chabazite, |Li-Na| [Al—Si—O]-CHA, DAF-5, Dehyd. Na-Chabazite, K-Chabazite, LZ-218, Linde D, Linde R, Phi, SSZ-62, UiO-21, Willhendersonite, ZK-14, ZYT-6, and mixtures of two or more thereof, wherein more preferably the seed crystals comprise one or more zeolites selected from the group consisting of (Ni(deta)$_2$)-UT-6, Chabazite, |Li—Na| [Al—Si—O]-CHA, DAF-5, Dehyd. Na-Chabazite, K-Chabazite (Iran), LZ-218, Linde D, Linde R, Phi, SSZ-62, UiO-21, Willhendersonite, ZK-14, ZYT-6, and mixtures of two or more thereof, and wherein even more preferably the seed crystals comprise Chabazite. According to an even more preferred embodiments Chabazite is employed as seed crystals in the inventive process, wherein preferably said Chabazite seed crystals are either obtainable according to the inventive process or have been obtained according to said process.

Concerning the Chabazite seed crystals preferably provided in step (1), there is in principle no particular restriction as the their chemical and/or physical properties, provided that a zeolitic material having a CHA-type framework structure comprising $YO_2$ and $X_2O_3$ is crystallized in step (2). Thus, as regards the $SiO_2$:$Al_2O_3$ molar ratio of the Chabazite seed crystals preferably used in the inventive process, no particular restriction applies, such that the seed crystals may display any suitable $SiO_2$:$Al_2O_3$ molar ratio. Thus, by way of examples, the $SiO_2$:$Al_2O_3$ molar ratio of the preferred Chabazite seed crystals may range anywhere from 4 to 200, preferably from 10 to 100, more preferably from 16 to 60, more preferably from 20 to 40, more preferably from 25 to 35, and even more preferably from 29 to 33.

Furthermore, regarding the non-framework ionic elements and/or molecules which may be contained in the Chabazite seed crystals preferably provided in step (1) of the inventive process, again no particular restrictions apply, wherein preferably the one or more non-framework elements and/or molecules comprise at least one cation and/or cationic elements, wherein said at least one cation and/or cationic element is preferably selected from the group consisting of $H^+$, $NH_4^+$, Li, Na, K, Cs, and combinations of two or more thereof, more preferably from the group consisting of H+, $NH_4^+$, Na, K, and combinations of two or more thereof, more preferably from the group consisting of $H^+$, $NH_4^+$, Na, and combinations of two or more thereof, wherein more preferably the at least one cation and/or cationic element is $H^+$ and/or Na, more preferably Na.

As regards the porosity and/or surface area of the Chabazite seed crystals preferably provided in step (1) of the inventive process, these may adopt any suitable values. Thus, as regards the BET surface area of the preferred Chabazite seed crystals as determined by nitrogen sorption at 77 K according to ISO 9277:2010, it may accordingly range anywhere from 100 to 850 $m^2/g$, wherein preferably the surface area is comprised in the range of from 300 to 800 $m^2/g$, more preferably from 400 to 750 $m^2/g$, more preferably from 500 to 700 $m^2/g$, more preferably from 550 to 650 $m^2/g$, and even more preferably from 580 to 640 $m^2/g$. According to particularly preferred embodiments of the present invention, the BET surface area of the Chabazite seed crystals preferably provided in step (1) of the inventive process as determined by nitrogen sorption at 77 K according to ISO 9277:2010 ranges from 600 to 630 m=/g.

Concerning the average particle size of the Chabazite seed crystals preferably provided in step (1) of the inventive process, they may accordingly display any conceivable particle size, and in particular any conceivable particle size D10 and/or D50 and/or D90. Thus, as concerns the particle size D10 of the preferred Chabazite seed crystals, no particular restriction applies such that by way of example, the particle size D10 thereof may be comprised in the range of anywhere from 5 to 200 nm. According to the present invention it is however preferred that the particle size D10 of the preferred Chabazite seed crystals lies within the range of from 10 to 150 nm, more preferably from 15 to 100 nm, more preferably from 20 to 70 nm, and more preferably from 25 to 50 nm. According to the present invention it is particularly preferred that the particle size D10 of the preferred Chabazite seed crystals lies within the range of from 30 to 40 nm.

With respect to the average particle size D50 of the preferred Chabazite seed crystals, same applies accordingly such that in principle said values may adopt any conceivable value. Thus, by way of example, the average particle size D50 of the preferred Chabazite seed crystals may be comprised in the range of from 50 to 1,000 nm, wherein preferably the average particle size D50 lies in the range of from 100 to 700 nm, more preferably from 150 to 500 nm, more preferably from 200 to 400 nm, and more preferably from 250 to 350 nm. According to the present invention it is particularly preferred that the average particle size D50 of the preferred Chabazite seed crystals lies in the range of from 270 to 290 nm.

As mentioned in the foregoing relative to the particle sizes D10 and D50, in general, no particular restrictions apply relative to the particle size D90 as well such that the preferred Chabazite seed crystals may adopt any conceivable particle size D90 value. Thus, by way of example, the particle size D90 of the preferred Chabazite seed crystals may be comprised in the range of anywhere from 500 to 3,000 nm, wherein it is preferable that the particle size D90 is comprised in the range of from 800 to 2,500 nm, more preferably from 1,000 to 2,000 nm, more preferably from 1,200 to 1,800 nm, more preferably from 1,300 to 1,700 nm, more preferably from 1,400 to 1,650 nm, more preferably from 1,450 to 1,600 nm, and more preferably from 1,500 to 1,580 nm. According to the present invention it is particularly preferred that the particle size D90 of the preferred Chabazite seed crystals is comprised in the range of from 1,530 to 1,550 nm.

Finally, the Chabazite seed crystals preferably provided in step (1) may be subject to any suitable treatment prior to their use. Thus, by way of Example, the preferred Chabazite seed crystals may be subject to any ion-exchange and/or thermal treatment prior to their use, such that the Chabazite seed crystals may be used as such, and in particular in the uncalcined form as obtained from synthesis, or may be subject to calcination prior to their use. According to the inventive process it is however preferred that the preferred Chabazite seed crystals are calcined prior to their use in the inventive process, wherein calcination is preferably performed at a temperature ranging from 400 to 850° C., wherein preferably, the calcination is conducted at a temperature ranging from 450 to 700° C., more preferably from 525 to 650° C., and more preferably from 575 to 625° C. Furthermore, the duration of the calcination may range anywhere from 1 to 48 h, wherein the calcination is preferably conducted for a period ranging from 2 to 24 h, more preferably from 3 to 12 h, more preferably from 3.5 to 8 h, and more preferably from 4 to 6 h.

According to the inventive process, any suitable amount of seed crystals can be provided in the mixture according to step (1), provided that a zeolitic material is crystallized in step (2). In general, the amount of seed crystals contained in the mixture according to step (1) ranges from 0.1 to 20 wt.-% based on 100 wt.-% of $YO_2$ in the at least one source for $YO_2$, preferably from 0.5 to 15 wt.-%, more preferably from 1 to 12 wt.-%, more preferably from 1.5 to 10 wt.-%, more preferably from 2 to 8 wt.-%, more preferably from 2.5 to 6 wt.-%, and more preferably from 3 to 5 wt.-%. According to particularly preferred embodiments of the inventive process, from 3.5 to 4.5 wt.-% of seed crystals according to any of the particular and preferred embodiments of the present invention are employed, based on 100 wt.-% of $YO_2$ in the at least one source for $YO_2$ provided in step (1) of the inventive process.

Concerning the further elements or compounds which may be contained in the mixture provided in step (1), there is no particular restriction according to the present invention in this respect, provided that a zeolitic material having the CHA-type framework structure may be obtained in step (2) of the inventive process. Thus, according to particular embodiments of the present invention, the mixture provided in step (1) may comprise one or more alkali metals M, wherein within the meaning of the present invention, the one or more alkali metals M preferably stands one or more elements selected from the group consisting of Li, Na, K, Rb, Cs, and combinations of two or more thereof, more preferably from the group consisting of Li, Na, K, and combinations of two or more thereof, wherein even more preferably the one of more alkali metals M stand for Na and/or K, and even more preferably for Na.

As regards particular embodiments of the present invention wherein the mixture provide in step (1) comprises one or more alkali metals M according to any of the particular and preferred meanings of the present invention, there is no particular restriction as to the amounts in which they may be contained in said mixture, provided that a zeolitic material having the CHA-type framework structure may be obtained in step (2) of the inventive process. According to particularly preferred embodiments of the present invention, however, the mixture provided in step (1) which is crystallized in step (2) contains 3 wt.-% or less of one or more alkali metals M based on 100 wt.-% of $YO_2$. According to embodiments which are further preferred, the mixture provided in step (1) contains 1 wt.-% or less of one or more alkali metals M, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and even more preferably 0.0001 wt.-% or less of one or more metals M based on 100 wt.-% of $YO_2$. According to particularly preferred embodiments of the present invention it is even further preferred that the mixture provided in step (1) and crystallized in step (2) contains no alkali metal M.

The present invention further comprises preferred embodiments of the inventive process wherein one or more sources of one or more elements suitable for isomorphous substitution of at least a portion of the Y atoms and/or of the X atoms in the zeolite framework structure having the CHA-type framework structure is added to the mixture according to step (1). In this respect, there is no particular restriction according to the present invention neither as to the type and/or number nor as to the amount of which said one or more sources of one or more elements suitable for isomorphous substitution may be employed. Thus, in principle, any one or more elements suitable for isomorphous substitution may be employed provided that they are at least partly incorporated into the framework structure of the zeolitic material crystallized in step (2) of the inventive process. According to preferred embodiments, the one or more elements are selected from the group consisting of B, Fe, Ti, Sn, Ga, Ge, Zr, V, Nb, Cu, Zn, Li, Be, and mixtures of two or more thereof, wherein more preferably the one or more elements are selected from the group consisting of B, Fe, Ti, Sn, Zr, Cu, and mixtures of two or more thereof. According to particularly preferred embodiments of the present invention, the one or more elements suitable for isomorphous substitution provided in step (1) comprise Fe and/or Cu, preferably Fe, wherein even more preferably the one or more elements are Fe and/or Cu. According to embodiments of the present invention which are particularly preferred, Cu is added as the element suitable for isomorphous substitution of at least a portion of the Y and/or of the X atoms in the mixture according to step (1).

As noted above, no particular restriction applies with respect to the amount of the one or more sources for isomorphous substitution preferably provided in the mixture in step (1) of the inventive process. Thus, by way of example, the molar ratio of $YO_2$ to the one or more elements suitable for isomorphous substitution in the mixture of step (1) of the inventive process may be comprised in the range of anywhere from 5 to 200, wherein it is preferred that said ratio is comprised in the range of from 10 to 100, more preferably of from 20 to 70, and even preferably of from 25 to 50. According to particularly preferred embodiments of the present invention wherein one or more elements suitable for isomorphous substitution are included in the mixture of step (1), it is preferred that the molar ratio of $YO_2$ to said one or more elements is comprised in the range of from 30 to 40.

The present invention further relates to a zeolitic material having a CHA-type framework structure which is either obtained by the process according to the present invention or by any conceivable process which leads to a zeolitic material having a CHA-type framework structure as obtainable according to the inventive process, wherein in particular the inventive process designates any of the particular and preferred embodiments thereof as defined in the present application.

Furthermore, the present invention also relates to a synthetic zeolitic material having a CHA-type framework structure, preferably obtainable and/or obtained according to the process of any of claims 1 to 24, wherein the CHA-type framework structure comprises $YO_2$ and $X_2O_3$, wherein Y is a tetravalent element and X is a trivalent element, and wherein the IR-spectrum of the zeolitic material comprises:
  a first absorption band (B1) ranging from 3,720 to 3,750 $cm^{-1}$; and
  a second absorption band (B2) ranging from 1,850 to 1,890 $cm^{-1}$;
  wherein the ratio of the maximum absorbance of the first absorption band to the second absorption band B1:B2 ranges from 1 to 2.5, preferably from 1.2 to 2, more preferably from 1.25 to 1.9, more preferably from 1.3 to 1.8, more preferably from 1.35 to 1.75, more preferably from 1.4 to 1.7, more preferably from 1.45 to 1.65, more preferably from 1.48 to 1.6, more preferably from 1.5 to 1.58, and more preferably from 1.52 to 1.56.

With respect to the first absorption band (B1) in the range of from 3,720 to 3,750 $cm^{-1}$, said band is attributed to stretching vibration of hydroxyl groups from isolated or nearly isolated silanol in the zeolitic material, and in particular from surface silanol groups. According to the present invention, it is preferred that the first absorption band (B1) is in the range of from 3,722 to 3,745 $cm^{-1}$, more preferably from 3,726 to 3,742 $cm^{-1}$, more preferably from 3,730 to 3,740 $cm^{-1}$, more preferably from 3,732 to 3,738 $cm^{-1}$, and more preferably from 3,734 to 3,736 $cm^{-1}$. As concerns the second absorption band (B2) in the range of from 1,850 to 1,890 $cm^{-1}$ on the other hand, it is preferred that said absorption is in the range of from 1,855 to 1,880 $cm^{-1}$, more preferably from 1.860 to 1,875 $cm^{-1}$, more preferably from 1,863 to 1,870 $cm^{-1}$, and more preferably from 1,865 to 1,867 $cm^{-1}$. Thus, according to the present invention it is particularly preferred that the first absorption band (B1) is in the range of from 3,722 to 3,745 $cm^{-1}$ and the second absorption band (B2) is in the range of from 1,855 to 1,880 $cm^{-1}$, more preferably that (B1) is in the range of from 3,726 to 3,742 $cm^{-1}$ and (B2) is in the range of from 1,860 to 1,875 $cm^{-1}$, more preferably that (B1) is in the range of from 3,730 to 3,740 $cm^{-1}$ and (B2) is in the range of from 1,863 to 1,870 $cm^{-1}$, more preferably that (B1) is in the range of from 3,732 to 3,738 $cm^{-1}$ and (B2) is in the range of from 1,865 to 1,867 $cm^{-1}$, and more preferably that (B1) is in the range of from 3,734 to 3,736 $cm^{-1}$ and (B2) is in the range of from 1,865 to 1,867 $cm^{-1}$.

As regards the state of the synthetic zeolitic material having a CHA-type framework structure from which the IR-spectrum is obtained, in general, no particular restriction applies for the synthetic zeolitic materials of the present invention such that the values of the absorption bands and the ratio of the maximum absorbance if the first and second absorption bands in the IR-spectrum as defined in the present application may refer to the IR-spectrum of the synthetic zeolitic material as obtained directly after crystallization or after any suitable workup thereof by any one or more suitable washing, drying, and calcination steps. According to the present invention it is however preferred that the IR-spectrum is directly obtained from the zeolitic material as-crystallized wherein after isolation, washing and drying thereof, the material has only been subject to calcination for removal of the organic template, wherein preferably calcination has been conducted according to any of the particular and preferred embodiments as defined in the present application, wherein more preferably calcination has been conducted at 550° C. for a duration of 5 h under air.

Regarding the further physical and/or chemical characteristics of the synthetic zeolitic material according to the present invention, no particular restrictions apply, provided that the zeolitic material displays a CHA-type framework structure and that the IR-spectrum of the synthetic zeolitic material displays absorption bands according to any of the particular and preferred embodiments of the present invention as defined in the present application. Consequently, as regards the average particle size of the zeolitic material, it may accordingly display any conceivable particle size, and in particular any conceivable particle size D10 and/or D50 and/or D90. Within the meaning of the present invention, the terms "D10", "D50", and "D90" respectively refer to the particle size in number of the synthetic zeolitic material of the present invention, wherein D10 refers to the particle size wherein 10% of the particles of the zeolitic material by number lie below said value, D50 refers to the particle size wherein 50% of the particles of the zeolitic material by number lie below said value, and D90 accordingly refers to the particle size wherein 90% of the particles of the zeolitic material by number lie below said particle size.

As concerns the particle size D10 of the inventive zeolitic material, no particular restriction applies such that by way of example, the particle size D10 of the zeolitic material may be comprised in the range of anywhere from 50 to 400 nm. According to the present invention it is however preferred that the particle size D10 of the zeolitic material lies within the range of from 90 to 360 nm, more preferably from 120 to 330 nm, more preferably from 150 to 300 nm, and more preferably from 180 to 270 nm. According to the present invention it is particularly preferred that the particle size D10 of the zeolitic material lies within the range of from 200 to 250 nm.

With respect to the average particle size D50 of the inventive zeolitic material, same applies accordingly such that in principle said values may adopt any conceivable value. Thus, by way of example, the average particle size D50 of the zeolitic material may be comprised in the range of from 150 to 600 nm, wherein preferably the average particle size D50 lies in the range of from 200 to 550 nm, more preferably from 240 to 510 nm, more preferably from 270 to 480 nm, more preferably from 300 to 450 nm, and more preferably from 330 to 420 nm. According to the present invention it is particularly preferred that the average particle size D50 of the inventive zeolitic material lies in the range of from 350 to 400 nm.

As mentioned in the foregoing relative to the particle sizes D10 and D50, in general, no particular restrictions apply relative to the particle size D90 as well such that the inventive zeolitic material may adopt any conceivable particle size D90 value. Thus, by way of example, the particle size D90 of the inventive zeolitic material may be comprised in the range of anywhere from 450 to 950 nm, wherein it is preferable that the particle size D90 is comprised in the range of from 500 to 900 nm, more preferably from 540 to 850 nm, more preferably from 570 to 800 nm, more preferably from 600 to 770 nm, more preferably from 630 to 740 nm, and more preferably from 650 to 720 nm. According to the present invention it is particularly preferred that the particle size D90 of the zeolitic material is comprised in the range of from 670 to 700 nm.

As for the determination of the IR-spectra of the inventive zeolitic materials, in principle no particular restrictions apply as to the state of the zeolitic material in which the particle size D10 and/or D50 and/or D90 is determined. Thus, within the meaning of the present invention, the particle size D10 and/or D50 and/or D90 of the inventive zeolitic material refers to the respective particle size of the zeolitic material either in the as-crystallized state or after having been subject to any suitable workup thereof by any one or more suitable washing, drying, and calcination steps. According to the present invention it is however preferred that the particle size D10 and/or D50 and/or D90 is directly obtained from the zeolitic material as-crystallized wherein preferably the zeolitic material has not been subject to any further treatment after crystallization other than optional isolation, optional washing, and/or optional drying. Thus, according to the present invention it is yet further preferred that the particle size D10 and/or D50 and/or D90 as defined in the present application are directly obtained from the as-crystallized zeolitic material after isolation, washing, and/or drying thereof, and preferably after isolation, washing, and drying thereof. It is, however, further preferred according to the present invention that the particle size D10 and/or D50 and/or D90 is directly obtained from the zeolitic material as-crystallized wherein after isolation, washing and drying thereof, the material has only been subject to calcination for removal of the organic template, wherein preferably calcination has been conducted according to any of the particular and preferred embodiments as defined in the present application, wherein more preferably calcination has been conducted at 550° C. for a duration of 5 h under air.

According to the present invention it is further preferred that the particle size D10, the average particle size D50, and the particle size D90 of the zeolitic material is comprised within defined ranges wherein the particle size D10 of the zeolitic material is comprised in the range of from 150 to 300 nm, more preferably from 180 to 270 nm, and more preferably from 200 to 250 nm, and the average particle size D50 of the zeolitic material is comprised in the range of from 300 to 450 nm, preferably from 330 to 420 nm, and more preferably from 350 to 400 nm, and the particle size D90 of the zeolitic material is comprised in the range of from 500 to 900 nm, preferably from 570 to 800 nm, more preferably from 630 to 740 nm, and more preferably from 670 to 700 nm. More preferably, it is preferred that the particle size D10 of the zeolitic material is comprised in the range of from 150 to 300 nm, the average particle size D50 of the zeolitic material is comprised in the range of from 300 to 450 nm, and the particle size D90 of the zeolitic material is comprised in the range of from 500 to 900 nm, preferably from 570 to 800 nm. More preferably, the particle size D10 of the zeolitic material is comprised in the range of from 180 to 270 nm, the average particle size D50 is comprised in the range of from 330 to 420 nm and the particle size D90 is comprised in the range of from 630 to 740 nm. According to the present invention it is particularly preferred that the particle size D10 of the zeolitic material is comprised in the range of from 200 to 250 nm, the average particle size D50 in the range of from 350 to 400 nm, and the particle size D90 is comprised in the range of from 670 to 700 nm.

According to the present invention, it is preferred that at least a portion of the Y atoms and/or of the X atoms of the CHA-type framework structure of the zeolitic materials is isomorphously substituted by one or more elements. In this respect, there is no particular restriction as to the one or more elements which may substitute Y atoms and/or X atoms of the CHA-type framework structure wherein preferably said elements are selected from the group consisting of B, Fe, Ti, Sn, Ga, Ge, Zr, V, Nb, Cu, Zn, Li, Be, and mixtures of two or more thereof, wherein even more preferably, the one or more elements are selected from the group consisting of B, Fe, Ti, Sn, Zr, Cu, and mixtures of two or more thereof. According to particularly preferred embodiments and in particular according to particularly preferred embodiments of the alternative zeolitic material of the present invention, at least a portion of the Y atoms and/or of the X atoms in the CHA-type framework structure is isomorphously substituted by Fe and/or Cu, and preferably by Cu.

As regards the amount of the one or more elements in the zeolitic materials which substitute at least a portion of the Y atoms and/or of the X atoms in the CHA-type framework structure, no particular restriction applies according to the present invention. Thus, by way of example, the molar ratio of $YO_2$ to the one or more elements isomorphously substituted in the CHA-type framework structure may range anywhere from 2 to 100, wherein the molar ratio is preferably comprised in the range of from 5 to 50, more preferably of from 8 to 30, more preferably of from 10 to 20, and even more preferably of from 13 to 15. According to particularly preferred embodiments, the molar ratio of $YO_2$ to the one or more elements isomorphously substituting Y atoms and/or X atoms in the CHA-type framework structure are comprised in the range of from 13 to 15.

As regards the CHA-type framework structure of the inventive zeolitic material, besides $YO_2$ and $X_2O_3$ contained therein as framework elements, no particular restriction applies as to any other elements which may be contained therein as further framework elements. Thus, besides or in addition to the preferred elements suitable for isomorphous substitution according the particular and preferred embodiments of the present invention which may be contained in the CHA-type framework structure of the zeolitic material, any further one or more elements than the afore-mentioned may also be contained therein as framework elements in addition to the one or more tetravalent elements Y and the one or more trivalent elements X. According to particular embodiments of the present invention, however, it is preferred that the zeolitic material having a CHA-type framework does not contain any substantial amount of P and/or As therein as framework element. Within the meaning of the present invention, the term "substantial" with respect to the amount of an element contained in the framework structure of the inventive zeolitic material preferably indicates an amount of 5 wt.-% or less of a framework element based on 100 wt.-% of $YO_2$ contained in the framework structure, preferably an amount of 1 wt.-% or less, more preferably of 0.5 wt.-% or less, more preferably of 0.1 wt.-% or less, more preferably of 0.05 wt.-% or less, more preferably of 0.01 wt.-% or less, more preferably of 0.005 wt.-% or less, more preferably of 0.001 wt.-% or less, more preferably of 0.0005 wt.-% or less, and even more preferably of 0.0001 wt.-% or less of a framework element based on 100 wt.-% of $YO_2$.

According to said particularly preferred embodiments wherein zeolitic material having a CHA-type framework does not contain any substantial amount of P and/or As, it is yet further preferred according to the present invention that the CHA-type framework does not contain any substantial amount of one or more elements selected from the group consisting of P, As, V, and combinations of two or more thereof, and more preferably no substantial amount of any one or more elements selected from the group consisting of P, As, Sb, Bi, V, Nb, Ta, and combinations of two or more thereof. According to yet further particularly preferred embodiments of the present invention, the inventive zeolitic material having a CHA-type framework structure does not contain any substantial amount of any pentavalent elements Z as framework element.

It is further preferred according to the present invention that the zeolitic material does not comprise any substantial amount of SSZ-13 and/or SSZ-15, wherein within the meaning of the present invention "substantial" with respect to the amount of SSZ-13 and/or SSZ-15 refers to an amount of 5 wt.-% or less thereof based on 100 wt.-% of the zeolitic material having a CHA-type framework structure according to any of the particular and preferred embodiments of the present invention, and preferably to an amount of 1 wt.-% or less, more preferably of 0.5 wt.-% or less, more preferably of 0.1 wt.-% or less, more preferably of 0.05 wt.-% or less, more preferably of 0.01 wt.-% or less, more preferably of 0.005 wt.-% or less, more preferably of 0.001 wt.-% or less, more preferably of 0.0005 wt.-% or less, and even more preferably of 0.0001 wt.-% or less of SSZ-13 and/or SSZ-15.

Concerning $YO_2:X_2O_3$ molar ratio displayed by the zeolitic materials of the present invention, any conceivable molar ratio may be adopted. Thus, by way of example, the $YO_2:X_2O_3$ molar ratio of the inventive materials may be comprised anywhere in the range of from 4 to 200, wherein preferably the $YO_2:X_2O_3$ molar ratio is comprised in the rage of from 10 to 120, more preferably of from 15 to 80, more preferably of from 18 to 50, more preferably of from 20 to 30, and even more preferably of from 22 to 28. According to particularly preferred embodiments of the present invention, the $YO_2:X_2O_3$ molar ratio of the zeolitic materials is comprised in the range of from 24 to 26.

According to the present invention, the zeolitic materials having an CHA-type framework structure comprise $YO_2$. In principle, Y stands for any conceivable tetravalent element, Y standing for either or several tetravalent elements. Preferred tetravalent elements according to the present invention include Si, Sn, Ti, Zr, and Ge, and combinations thereof. More preferably, Y stands for Si, Ti, or Zr, or any combination of said tetravalent elements, even more preferably for Si, and/or Sn. According to the present invention, it is particularly preferred that Y stands for Si.

As regards $X_2O_3$ optionally comprised in the CHA-framework structure of the zeolitic materials, X may in principle stand for any conceivable trivalent element, wherein X stands for one or several trivalent elements. Preferred trivalent elements according to the present invention include Al, B, In, and Ga, and combinations thereof. More preferably, X stands for Al, B, or Ga, or any combination of said trivalent elements, even more preferably for Al and/or B. According to the present invention, it is particularly preferred that X stands for Al.

In addition to the framework elements of the zeolitic materials of the present invention having an CHA-type framework structure, said zeolitic materials preferably further contains one or more types of non-framework elements which do not constitute the framework structure and are accordingly present in the pores and/or cavities formed by the framework structure and typical for zeolitic materials in general. In this respect, there is no particular restriction as to the types of non-framework elements which may be contained in the zeolitic materials, nor with respect to the amount in which they may be present therein. It is, however, preferred that the zeolitic materials comprise one or more cation and/or cationic elements as ionic non-framework elements, wherein again no particular restriction applies as to the type or number of different types of ionic non-framework elements which may be present in the zeolitic materials, nor as to their respective amount According to preferred embodiments of the present invention, the ionic non-framework elements preferably comprise one or more cations and/or cationic elements selected from the group consisting of $H^+$, $NH_4^+$, Mg, Sr, Zr, Cr, Mo, Fe, Co, Ni, Cu, Zn, Ru, Rh, Pd, Ag, Os, Ir, Pt, Au, and mixtures of two or more thereof, wherein more preferably these are selected from the group consisting of $H^+$, $NH_4^+$, Mg, Sr, Cr, Mo, Fe. Co, Ni, Cu, Zn, Ag, and mixtures of two or more thereof, more preferably from the group consisting of $H^+$. $NH_4^+$, Mg, Cr, Mo, Fe, Ni, Cu, Zn, Ag, and mixtures of two or more thereof. According to particularly preferred embodiments of the present invention, the ionic non-framework elements comprise one or more cations and/or cationic elements selected from the group consisting of Mg, Mo. Fe, Ni, Cu, Zn, Ag, and mixtures of two or more thereof, wherein more preferably the one or more cation and/or cationic elements comprise Cu and/or Fe, preferably Cu, wherein even more preferably the one or more cation and/or cationic elements consist of Cu and/or Fe, preferably of Cu.

Concerning the amounts in which the one or more non-framework elements may be contained in the inventive zeolitic materials according to any of the particular and preferred embodiments of the present invention, no general restriction applies such that in principle any suitable amount of one or more cation and/or cationic elements may be contained as non-framework element therein. Thus, by way of example, the one or more cation and/or cationic elements comprised as ionic non-framework elements in the inventive zeolitic materials may be contained therein in an amount ranging anywhere from 0.01 to 25 wt.-% based on 100 wt.-% of $YO_2$ comprised in the zeolitic material, wherein preferably the one or more cations and/or cationic elements are contained in the zeolitic material in an amount ranging from 0.05 to 15.0 wt.-%, and more preferably from 0.1 to 10.0 wt.-%, more preferably from 0.5 to 6.0 wt.-%, more preferably from 1.0 to 4.0 wt.-%, more preferably from 1.5 to 3.5 wt.-%, and more preferably from 2.0 to 3.0 wt.-%. According to the present invention it is however particularly preferred that the one or more cations and/or cationic elements are contained in the inventive zeolitic material in an amount ranging from 2.3 to 2.7 wt.-% based on 100 wt.-% of $YO_2$ comprised in the zeolitic material.

As regards the $^{27}Al$ MAS NMR of the inventive zeolitic materials having the CHA-type framework structure comprising $X_2O_3$ wherein X includes Al or is preferably Al, there is no particular restriction as to the number and/or respective ppm values and/or relative intensities of the signals which may be comprised in the NMR spectrum. According to the present invention, however, it is preferred that the $^{27}Al$ MAS NMR spectrum of the inventive materials comprises a first peak (P1) comprised in the range of from 55.0 to 61.5 ppm and a second peak (P2) comprised in the range of from −0.0 to −7.0 ppm, wherein the integration of the first and second peaks in the $^{27}Al$ MAS NMR spectrum of the zeolitic material preferably offers a ratio of the integration values P1:P2 of 1:(0.005-0.2). More preferably, the first peak (P1) is comprised in the range of from 56.0 to 60.5 ppm, and the second peak (P2) is comprised in the range of from −0.5 to −6.0 ppm, wherein the integration of the first and second peaks offers a ratio of the integration values P1:P2 of 1:(0.01-0.18). More preferably, the first peak (P1) is comprised in the range of from 56.5 to 60.0 ppm and the second peak (P2) is comprised in the range of from −1.0 to −5.5 ppm, wherein the integration of the first and second peaks offers a ratio of the integration values P1:P2 of 1:(0.03-0.16). More preferably, the first peak (P1) is comprised in the range of from 57.0 to 59.5 ppm and the second peak (P2) is comprised in the range of from −1.5 to −5.0 ppm, wherein the integration of the first and second peaks offers a ratio of the integration values P1:P2 of 1:(0.05-0.15). More preferably, the first peak (P1) is comprised in the range of from 57.5 to 59.0 ppm and the second peak (P2) is comprised in the range of from −2.0 to −4.5 ppm, wherein the integration of the first and second peaks offers a ratio of the integration values P1:P2 of 1:(0.08-0.14). More preferably, the first peak (P1) is comprised in the range of from 57.8 to 58.7 ppm and the second peak (P2) is comprised in the range of from −2.3 to −4.1 ppm, wherein the integration of the first and second peaks offers a ratio of the integration values P1:P2 of 1:(0.08-0.14). More preferably, the first peak (P1) is comprised in the range of from 58.0 to 58.5 ppm and the second peak (P2) is comprised in the range of from −2.5 to −3.8 ppm, wherein the integration of the first and second peaks offers a ratio of the integration values P1:P2 of 1:(0.09-0.13). According to particularly preferred embodiments of the present invention, the $^{27}Al$ MAS NMR of the zeolitic material comprises a first peak (P1) comprised in the range of from 58.4 to 58.5 ppm and a second peak (P2) comprised in the range of from −2.7 to −3.6 ppm, preferably in the range of from −2.8 to −3.4 ppm, wherein the integration of the first and second peaks in the $^{27}Al$ MAS NMR of the zeolitic material preferably offers a ratio of the integration values P1:P2 of 1:(0.1-0.12).

There is no particular restriction according to the present invention as to the state in which the zeolitic material is subject to the $^{27}Al$ MAS NMR experiment. It is however preferred, in particular regarding the intensity of the first and second peaks observed in the $^{27}Al$ MAS NMR spectrum that the inventive zeolitic material having a CHA-type framework structure has not been subject to a dealumination treatment or even more preferably to any treatment susceptible of substantially influencing the content of framework aluminum present in the zeolitic material as-crystallized. Accordingly, according to a particularly preferred embodiment of the present invention, the $^{27}Al$ MAS NMR of the zeolitic material according to any of the particular and preferred embodiments wherein X comprises Al refers to a $^{27}Al$ MAS NMR spectrum and to the according values obtained therein wherein the zeolitic material has not been subject to any post-synthetic treatment and is therefore an untreated zeolitic material as-crystallized. According to the present invention it is, however, further preferred that the $^{27}Al$ MAS NMR of the zeolitic material according to any of the particular and preferred embodiments wherein X comprises Al refers to a $^{27}Al$ MAS NMR spectrum and to the according values obtained therein obtained from the zeolitic material as-crystallized wherein after isolation, washing and drying thereof, the material has only been subject to calcination for removal of the organic template, wherein preferably calcination has been conducted according to any of the particular and preferred embodiments as defined in the present application, wherein more preferably calcination has been conducted at 550° C. for a duration of 5 h under air.

Therefore embodiments of the zeolitic material having a CHA-type framework structure are preferred according to the present invention wherein the $^{27}Al$ MAS NMR of the zeolitic material, and preferably of the untreated zeolitic material as-crystallized, comprises:

a first peak (P1) ranging from 55.0 to 61.5 ppm, preferably from 56.0 to 60.5 ppm, more preferably from 56.5 to 60.0 ppm, more preferably from 57.0 to 59.5 ppm, more preferably from 57.5 to 59.0 ppm, more preferably from 57.8 to 58.7 ppm, more preferably from 58.0 to 58.5 ppm, and even more preferably from 58.4 to 58.5 ppm; and a second peak (P2) ranging from −0.0 to −7.0 ppm, preferably from −0.5 to −6.0 ppm, more preferably from −1.0 to −5.5 ppm, more preferably from −1.5 to −5.0 ppm, more preferably from −2.0 to −4.5 ppm, more preferably from −2.3 to −4.1 ppm, more preferably from −2.5 to −3.8 ppm, more preferably from −2.7 to −3.6 ppm, and even more preferably from −2.8 to −3.4 ppm; wherein the integration of the first and second peaks in the $^{27}$Al MAS NMR of the zeolitic material offers a ratio of the integration values P1:P2 ranges from 1:(0.005-0.2), preferably from 1:(0.01-0.18), more preferably from 1:(0.03-0.16), more preferably from 1:(0.05-0.15), more preferably from 1:(0.08-0.14), more preferably from 1:(0.09-0.13), and even more preferably from 1:(0.1-0.12).

As regards the $^{29}$Si MAS NMR of the inventive zeolitic material having the CHA-type framework structure comprising YO$_2$ wherein Y includes Si or is preferably Si, there is no particular restriction as to the number and/or respective ppm values and/or relative intensities of the signals displayed in the NMR spectrum. According to the present invention, however, it is preferred that the $^{29}$Si MAS NMR comprises:

a first peak (P'1) in the range of from −102.0 to −106.0 ppm, and a second peak (P'2) in the range of from −108.0 to −112.5 ppm, wherein more preferably the integration of the first and second peaks in the $^{29}$Si MAS NMR of the zeolitic material offers a ratio of the integration values P'1:P'2 comprised in the range of from 0.1 to 0.9. More preferably, the first peak (P'1) is comprised in the range of from −102.5 to −105.5 ppm, and preferably of from −103.0 to −105.0 ppm, and the second peak (P'2) is in the range of from −109.0 to −111.5 ppm, wherein the integration of the first and second peaks preferably offers a ratio of the integration values P'1:P'2 comprised in the range of from 0.2 to 0.7, and preferably of from 0.25 to 0.6. More preferably, the first peak (P'1) is comprised in the range of from −103.2 to −104.8 ppm, and preferably of from −103.4 to −104.5 ppm and the second peak (P'2) is in the range of from −109.5 to −111.0 ppm, wherein the integration of the first and second peaks preferably offers a ratio of the integration values P'1:P'2 comprised in the range of from 0.3 to 0.5, more preferably of from 0.35 to 0.45. More preferably, the first peak (P'1) is comprised in the range of from −103.6 to −104.3 ppm, and the second peak (P'2) is in the range of from −110.0 to −110.5 ppm, wherein the integration of the first and second peaks preferably offers a ratio of the integration values P'1:P'2 comprised in the range of from 0.37 to 0.43. According to the present invention it is however particularly preferred that the $^{29}$Si MAS NMR of the zeolitic material comprises a first peak (P'1) comprised in the range of from −103.8 to −104.1 ppm and a second peak (P'2) in the range of from −110.1 to −110.3 ppm, wherein the integration of the first and second peaks in the NMR of the zeolitic material preferably offers a ratio of the integration values P'1:P'2 comprised in the range of from 0.39 to 0.41.

There is no particular restriction according to the present invention as to the state in which the zeolitic material is subjected to the $^{29}$Si MAS NMR experiment. It is however preferred that the values given in the present application relative to the $^{29}$Si MAS NMR spectrum are obtained from the zeolitic material which has not been subject to any post-synthetic treatment and is therefore an untreated zeolitic material as-crystallized. According to the present invention it is, however, further preferred that the values given in the present application relative to the $^{29}$Si MAS NMR spectrum are directly obtained from the zeolitic material as-crystallized wherein after isolation, washing and drying thereof, the material has only been subject to calcination for removal of the organic template, wherein preferably calcination has been conducted according to any of the particular and preferred embodiments as defined in the present application, wherein more preferably calcination has been conducted at 550° C. for a duration of 5 h under air.

Therefore, it is preferred according to the present invention that the $^{29}$Si MAS NMR of the zeolitic material having a CHA-type framework structure as defined in any of the particular and preferred embodiments of the present invention comprises:

a first peak (P'1) ranging from −102.0 to −106.0 ppm, preferably from −102.5 to −105.5 ppm, preferably from −103.0 to −105.0 ppm, preferably from −103.2 to −104.8 ppm, preferably from −103.4 to −104.5 ppm, preferably from −103.6 to −104.3 ppm, and even more preferably from −103.8 to −104.1 ppm; and a second peak (P'2) ranging from −108.0 to −112.5 ppm, preferably from −109.0 to −111.5 ppm, preferably from −109.5 to −111.0 ppm, preferably from −110.0 to −110.5 ppm, and even more preferably from −110.1 to −110.3 ppm, wherein the integration of the first and second peaks in the $^{29}$Si MAS NMR of the zeolitic material offers a ratio of the integration values P'1:P'2 ranging from 0.1 to 0.9, preferably from 0.2 to 0.7, more preferably from 0.25 to 0.6, more preferably from 0.3 to 0.5, more preferably from 0.35 to 0.45, more preferably from from 0.37 to 0.43, and even more preferably from 0.39 to 0.41.

There is no particular restriction according to the present invention as to the suitable physical and/or chemical characteristics of the inventive zeolitic materials. Thus, as regards for example the porosity and/or surface area of the inventive materials, these may adopt any suitable values. Thus, as regards the BET surface area of the zeolitic materials as determined by nitrogen sorption at 77 K according to ISO 9277:2010, it may accordingly range anywhere from 200 to 950 m$^2$/g, wherein preferably the surface area of the inventive zeolitic materials is comprised in the range of from 400 to 850 m$^2$/g, more preferably from 500 to 800 m$^2$/g, more preferably from 550 to 750 m$^2$/g, more preferably from 580 to 700 m$^2$/g, more preferably from 610 to 680 m$^2$/g. According to particularly preferred embodiments of the present invention, the BET surface area of the zeolitic materials as determined according to DIN 66135 ranges from 635 to 665 m$^2$/g.

As regards the micropore volume of the zeolitic material as determined according to DIN 66133, on the other hand, it may range anywhere from 0.5 to 3 cm$^3$/g, wherein preferably the micropore volume of the inventive zeolitic material is comprised in the range of from 0.8 to 2.5 cm$^3$/g, more preferably from 1 to 2.2 cm$^3$/g, more preferably from 1.1 to 2 cm$^3$/g, more preferably from 1.2 to 1.8 cm$^3$/g, more preferably from 1.3 to 1.7 cm$^3$/g, and more preferably from 1.4 to 1.6 cm$^3$/g. According to particularly preferred embodiments of the present invention, the micropore volume of the zeolitic materials as determined according to DIN 66133 ranges from 1.45 to 1.55 cm$^3$/g.

There is no particular restriction according to the present invention as to the state in which the zeolitic material is subjected to the BET surface area and micropore volume analysis. It is however preferred that the BET surface area and micropore volume values respectively given in the present application are obtained from the zeolitic material as-crystallized wherein after isolation, washing and drying thereof, the material has only been subject to calcination for removal of the organic template, wherein preferably calcination has been conducted according to any of the particular and preferred embodiments as defined in the present application, wherein more preferably calcination has been conducted at 550° C. for a duration of 5 h under air.

In general, there is no particular restriction according to the present invention as to the specific type or types of zeolitic materials having a CHA-type framework which may be contained in the inventive zeolitic material. It is, however, preferred that the inventive zeolitic material comprises one or more zeolites selected from the group consisting of (Ni(deta)$_2$)-UT-6, Chabazite, |Li-Na| [Al—Si—O]-CHA, DAF-5, Dehyd. Na-Chabazite, K-Chabazite, LZ-218, Linde D, Linde R, Phi, SSZ-62, UiO-21, Willhendersonite, ZK-14, ZYT-6, and combinations of two or more thereof. More preferably the inventive zeolitic material having a CHA-type framework structure comprises one or more zeolites selected from the group consisting of (Ni(deta)$_2$)-UT-6, Chabazite, |Li-Na| [Al—Si—O]-CHA, DAF-5, Dehyd. Na-Chabazite, K-Chabazite (Iran), LZ-218, Linde D, Linde R, Phi, SSZ-62, UiO-21, Willhendersonite, ZK-14, ZYT-6, and combinations of two or more thereof. According to particularly preferred embodiments of the present invention, the inventive zeolitic material comprises Chabazite, wherein even more preferably the inventive zeolitic material according to particular and preferred embodiments of the present invention is Chabazite.

Depending on the specific needs of its application, the zeolitic material of the present invention can be employed as such, like in the form of a powder, a spray powder or a spray granulate obtained from above-described separation techniques, e.g. decantation, filtration, centrifugation, or spraying.

In many industrial applications, it is often desired on the part of the user not to employ the zeolitic material as powder or sprayed material, i.e. the zeolitic material obtained by the separation of the material from its mother liquor, optionally including washing and drying, and subsequent calcination, but a zeolitic material which is further processed to give moldings. Such moldings are required particularly in many industrial processes, e.g. in many processes wherein the zeolitic material of the present invention is employed as catalyst or adsorbent.

Accordingly, the present invention also relates to a molding comprising the inventive zeolitic material.

In general, the powder or sprayed material can be shaped without any other compounds, e.g. by suitable compacting, to obtain moldings of a desired geometry, e.g. tablets, cylinders, spheres, or the like.

Preferably, the powder or sprayed material is admixed with or coated by a suitable refractory binder. In general, suitable binders are all compounds which impart adhesion and/or cohesion between the zeolitic material particles to be bonded which goes beyond the physisorption which may be present without a binder. Examples of such binders are metal oxides, such as, for example, $SiO_2$, $Al_2O_3$, $TiO_2$, $ZrO_2$ or MgO or clays, or mixtures of two or more of these compounds. Naturally occurring clays which can be employed include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. In addition, the zeolitic material according to the present invention can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The zeolitic material of the present invention may therefore also be provided in the form of extrudates, pellets, tablets or particles of any other suitable shape, for use as a packed bed of particulate catalyst, or as shaped pieces such as plates, saddles, tubes, or the like.

Also preferably, the powder or the sprayed material, optionally after admixing or coating by a suitable refractory binder as described above, is formed into a slurry, for example with water, which is deposited upon a suitable refractory carrier. The slurry may also comprise other compounds such as, e.g., stabilizers, defoamers, promoters, or the like. Typically, the carrier comprises a member, often referred to as a "honeycomb" carrier, comprising one or more refractory bodies having a plurality of fine, parallel gas flow passages extending there through. Such carriers are well known in the art and may be made of any suitable material such as cordierite or the like.

In general, the zeolitic material described above can be used as molecular sieve, adsorbent, catalyst, catalyst support or binder thereof. For example, the zeolitic material can be used as molecular sieve to dry gases or liquids, for selective molecular separation, e.g. for the separation of hydrocarbons or amines; as ion exchanger; as chemical carrier; as adsorbent, in particular as adsorbent for the separation of hydrocarbons or amines; or as a catalyst. Most preferably, the zeolitic material according to the present invention is used as a catalyst and/or as a catalyst support.

According to a preferred embodiment of the present invention, the zeolitic material of the invention is used in a catalytic process, preferably as a catalyst and/or catalyst support, and more preferably as a catalyst. In general, the zeolitic material of the invention can be used as a catalyst and/or catalyst support in any conceivable catalytic process, wherein processes involving the conversion of at least one organic compound is preferred, more preferably of organic compounds comprising at least one carbon-carbon and/or carbon-oxygen and/or carbon-nitrogen bond, more preferably of organic compounds comprising at least one carbon-carbon and/or carbon-oxygen bond, and even more preferably of organic compounds comprising at least one carbon-carbon bond. In particularly preferred embodiments of the present invention, the zeolitic material is used as a catalyst and/or catalyst support in a fluid catalytic cracking (FCC) process.

Furthermore, it is preferred according to the present invention, that the zeolitic material is used as a catalyst for producing light olefins from non-petroleum feedstock by conversion of oxygenates, such as lower alcohols (methanol, ethanol), ethers (dimethyl ether, methyl ethyl ether), esters (dimethyl carbonate, methyl formate) and the like to olefins, and especially in the conversion of lower alcohols to light olefins. According to particularly preferred embodiments, the zeolitic material of the present invention is used in the conversion of methanol to olefin (MTO)

According to a further embodiment of the present invention, the zeolitic material of the invention is preferably used in a catalytic process involving the conversion of at least one compound comprising at least one nitrogen-oxygen bond. Particularly preferred according to the present invention is the use of the zeolitic material as a catalyst and/or catalyst support in a selective catalytic reduction (SCR) process for the selective reduction of nitrogen oxides $NO_x$; for the oxidation of $NH_3$, in particular for the oxidation of $NH_3$ slip in diesel systems; for the decomposition of $N_2O$. According to particularly preferred embodiments of the present invention, the zeolitic material used in a catalytic process involving the conversion of at least one compound comprising at least one nitrogen-oxygen bond comprises Cu and/or Fe, and more preferably Cu.

Therefore, the present invention also relates to a method for selectively reducing nitrogen oxides $NO_x$ by contacting a stream containing $NO_x$ with a catalyst containing the zeolitic material according to the present invention under suitable reducing conditions; to a method of oxidizing $NH_3$, in particular of oxidizing $NH_3$ slip in diesel systems, by contacting a stream containing $NH_3$ with a catalyst containing the zeolitic material according to the present invention under suitable oxidizing conditions; to a method of decomposing of $N_2O$ by contacting a stream containing $N_2O$ with a catalyst containing the zeolitic material according to the present invention under suitable decomposition conditions; to a method of controlling emissions in Advanced Emission Systems such as Homogeneous Charge Compression Ignition (HCCI) engines by contacting an emission stream with a catalyst containing the zeolitic material according to the present invention under suitable conditions; to a fluid catalytic cracking FCC process wherein the zeolitic material according to the present invention is employed as additive; to a method of converting an organic compound by contacting said compound with a catalyst containing the zeolitic material according to the present invention under suitable conversion conditions; to a "stationary source" process wherein a catalyst is employed containing the zeolitic material according to the present invention.

Therefore, the present invention also relates to a method for selectively reducing nitrogen oxides $NO_x$, wherein a gaseous stream containing nitrogen oxides $NO_x$, preferably also containing ammonia and/urea, is contacted with the zeolitic material according to the present invention or the zeolitic material obtainable or obtained according to the present invention, preferably in the form of a molded catalyst, still more preferably as a molded catalyst wherein the zeolitic material is deposited on a suitable refractory carrier, still more preferably on a "honeycomb" carrier.

The nitrogen oxides which are reduced using a catalyst containing the zeolitic material according to the present invention or the zeolitic material obtainable or obtained according to the present invention may be obtained by any process, e.g. as a waste gas stream. Among others, waste gas streams as obtained in processes for producing adipic acid, nitric acid, hydroxylamine derivatives, caprolactame, glyoxal, methyl-glyoxal, glyoxylic acid or in processes for burning nitrogenous materials may be mentioned.

Most preferably, the zeolitic material according to the present invention or the zeolitic material obtainable or obtained according to the present invention is used as a molded catalyst, still more preferably as a molded catalyst wherein the zeolitic material is deposited on a suitable refractory carrier, still more preferably on a "honeycomb" carrier, for the selective reduction of nitrogen oxides $NO_x$, i.e. for selective catalytic reduction of nitrogen oxides. In particular, the selective reduction of nitrogen oxides wherein the zeolitic material according to the present invention is employed as catalytically active material is carried out in the presence ammonia or urea. While ammonia is the reducing agent of choice for stationary power plants, urea is the reducing agent of choice for mobile SCR systems. Typically, the SCR system is integrated in the engine and vehicle design and, also typically, contains the following main components: SCR catalyst containing the zeolitic material according to the present invention; a urea storage tank; a urea pump; a urea dosing system; a urea injector/nozzle; and a respective control unit.

Furthermore, it is preferred according to the present invention that the zeolitic material is used as a molecular trap for organic compounds. In general, any type of organic compound may be trapped in the zeolitic material, wherein it is preferred that the compound is reversibly trapped, such that it may be later released from the zeolitic material, preferably wherein the organic compound is released—preferably without conversion thereof—by an increase in temperature and/or a decrease in pressure. Furthermore, it is preferred that the zeolitic material is used to trap organic compounds of which the dimensions allow them to penetrate the microporous system of the molecular structure. According to yet further embodiments of the present invention, it is preferred that the trapped compounds are released under at least partial conversion thereof to a chemical derivative and/or to a decomposition product thereof, preferably to a thermal decomposition product thereof.

When preparing specific catalytic compositions or compositions for different purposes, it is also conceivable to blend the zeolitic material according to the present invention with at least one other catalytically active material or a material being active with respect to the intended purpose. It is also possible to blend at least two different inventive materials which may differ in their $YO_2:X_2O_3$ molar ratio, and in particular in their $SiO_2:Al_2O_3$ molar ratio, and/or in the presence or absence of one or more further metals such as one or more transition metals and/or in the specific amounts of a further metal such as a transition metal, wherein according to particularly preferred embodiments, the one or more transition metal comprises Cu and/or Fe, more preferably Cu. It is also possible to blend at least two different inventive materials with at least one other catalytically active material or a material being active with respect to the intended purpose.

Also, the catalyst may be disposed on a substrate. The substrate may be any of those materials typically used for preparing catalysts, and will usually comprise a ceramic or metal honeycomb structure. Any suitable substrate may be employed, such as a monolithic substrate of the type having fine, parallel gas flow passages extending there through from an inlet or an outlet face of the substrate, such that passages are open to fluid flow there through (referred to as honeycomb flow through substrates). The passages, which are essentially straight paths from their fluid inlet to their fluid outlet, are defined by walls on which the catalytic material is disposed as a washcoat so that the gases flowing through the passages contact the catalytic material. The flow passages of the monolithic substrate are thin-walled channels, which can be of any suitable cross-sectional shape and size such as trapezoidal, rectangular, square, sinusoidal, hexagonal, oval, circular, etc. Such structures may contain from about 60 to about 400 or more gas inlet openings (i.e., cells) per square inch (2.54 cm×2.54 cm) of cross section.

The substrate can also be a wall-flow filter substrate, where the channels are alternately blocked, allowing a gaseous stream entering the channels from one direction (inlet direction), to flow through the channel walls and exit from the channels from the other direction (outlet direction).

The catalyst composition can be coated on the flow through or wall-flow filter. If a wall flow substrate is utilized, the resulting system will be able to remove particulate matter along with gaseous pollutants. The wall-flow filter substrate can be made from materials commonly known in the art, such as cordierite, aluminum titanate or silicon carbide. It will be understood that the loading of the catalytic composition on a wall flow substrate will depend on substrate properties such as porosity and wall thickness, and typically will be lower than loading on a flow through substrate.

The ceramic substrate may be made of any suitable refractory material, e.g., cordierite, cordierite-alumina, silicon nitride, zircon mullite, spodumene, alumina-silica magnesia, zircon silicate, sillimanite, a magnesium silicate, zircon, petalite, alpha-alumina, an aluminosilicate, and the like.

The substrates useful for the catalysts of embodiments of the present invention may also be metallic in nature and be composed of one or more metals or metal alloys. The metallic substrates may be employed in various shapes such as corrugated sheet or monolithic form. Suitable metallic supports include the heat resistant metals and metal alloys such as titanium and stainless steel as well as other alloys in which iron is a substantial or major component. Such alloys may contain one or more of nickel, chromium and/or aluminum, and the total amount of these metals may advantageously comprise at least 15 wt. % of the alloy, e.g., 10-25 wt. % of chromium, 3-8 wt. % of aluminum and up to 20 wt. % of nickel. The alloys may also contain small or trace amounts of one or more other metals such as manganese, copper, vanadium, titanium, and the like. The surface or the metal substrates may be oxidized at high temperatures, e.g., 1000° C. and higher, to improve the resistance to corrosion of the alloys by forming an oxide layer on the surfaces of the substrates. Such high temperature-induced oxidation may enhance the adherence of the refractory metal oxide support and catalytically promoting metal components to the substrate.

In alternative embodiments, zeolitic material according to the present invention may be deposited on an open cell foam substrate. Such substrates are well known in the art, and are typically formed of refractory ceramic or metallic materials.

Especially preferred is the use of a catalyst containing the zeolitic material according to the present invention or the zeolitic material obtainable or obtained according to the present invention for removal of nitrogen oxides $NO_x$ from exhaust gases of internal combustion engines, in particular diesel engines, which operate at combustion conditions with air in excess of that required for stoichiometric combustion, i.e., lean.

Therefore, the present invention also relates to a method for removing nitrogen oxides $NO_x$ from exhaust gases of internal combustion engines, in particular diesel engines, which operate at combustion conditions with air in excess of that required for stoichiometric combustion, i.e., at lean conditions, wherein a catalyst containing the zeolitic material according to the present invention or the zeolitic material obtainable or obtained according to the present invention is employed as catalytically active material.

The present invention therefore relates to the use of the zeolitic material of the invention, in particular in the field of catalysis and/or in the treatment of exhaust gas, wherein said exhaust gas treatment comprises industrial and automotive exhaust gas treatment. In these and other applications, the zeolitic material of the present invention can by way of example be used as a molecular sieve, catalyst, and/or catalyst support.

In embodiments of the present invention involving the use of the zeolitic material of the invention in exhaust gas treatment, the zeolitic material is preferably used in the treatment of industrial or automotive exhaust gas, more preferably as a molecular sieve in said applications. In a particularly preferred embodiment, the zeolitic material used in exhaust gas treatment is comprised in a hydrocarbon trap.

Therefore, the present invention further relates to the use of a zeolitic material according to the present invention, and in particular according to preferred and particularly preferred embodiments thereof as defined in the present application, as a molecular sieve, as an adsorbent, for ion-exchange, as a catalyst and/or as a catalyst support, preferably as a catalyst for the selective catalytic reduction (SCR) of nitrogen oxides $NO_x$; for the storage and/or adsorption of $CO_2$; for the oxidation of $NH_3$, in particular for the oxidation of $NH_3$ slip in diesel systems; for the decomposition of $N_2O$; as an additive in fluid catalytic cracking (FCC) processes; and/or as a catalyst in organic conversion reactions, preferably in the conversion of alcohols to olefins, and more preferably in methanol to olefin (MTO) catalysis. According to the present invention it is however particular preferred that the organotemplate-free zeolitic material having a CHA-type framework structure is used as a catalyst for the selective catalytic reduction (SCR) of nitrogen oxides $NO_x$.

As regards the particularly preferred use of the zeolitic material for the selective catalytic reduction of $NO_x$, it is further preferred that the selective catalytic reduction is performed on exhaust gas containing $NO_x$, and more preferably on exhaust gas from a combustion engine, wherein the combustion engine is preferably a diesel engine or a lean burn gasoline engine.

Concerning the form in which the inventive zeolitic material is employed for the treatment of $NO_x$, no particular restriction applies, such that it may be employed as such or in connection with one or more further elements specifically adapted to the treatment of $NO_x$, and in particular of $NO_x$ in exhaust gases. Thus, it is particularly preferred that for the treatment of $NO_x$ and in particular of $NO_x$ in exhaust gas according to any of the particular and preferred embodiments of the present invention, the zeolitic material according to the present invention is provided as a catalyst for selective catalytic reduction (SCR) on a soot filter which comprises a porous wall flow substrate, the wall flow substrate comprising an inlet end, an outlet end, a substrate axial length extending between the inlet end and the outlet end, and a plurality of channels defined by internal walls of the wall flow substrate, wherein the plurality of channels comprise inlet channels having an open inlet end and a closed outlet end, and outlet channels having a closed inlet end and an open outlet end. As concerns the manner in which the zeolitic material according to the present invention is provided on the soot filter, no particular restrictions apply such that it may be provided thereon in any suitable manner. According to the present invention it is however preferred that the zeolitic material is provided on at least a portion of the surface of the inlet channel walls and on at least a portion of the surface of the pores within the channel walls underneath the surface of the channel walls coated with zeolitic material, wherein the portion of the inlet channel walls coated with the zeolitic material extends from the inlet end to x % of the substrate axial length with 0<x<100. Alternatively, or in addition thereto, and preferably in addition thereto, the zeolitic material is provided on at least a portion of the surface of the outlet channel walls and on at least a portion of the surface of the pores within the channel walls underneath the surface of the channel walls coated with the zeolitic material, wherein the portion of the outlet channel walls coated with the SCR catalyst extends from the outlet end to y % of the substrate axial length with 0<y<100.

Therefore, the present invention further relates to a catalyzed soot filter (CSF) for selective catalytic reduction (SCR), wherein the CSF comprises a porous wall flow substrate, the wall flow substrate comprising an inlet end, an outlet end, a substrate axial length extending between the inlet end and the outlet end, and a plurality of channels defined by internal walls of the wall flow substrate, wherein the plurality of channels comprise inlet channels having an open inlet end and a closed outlet end, and outlet channels having a closed inlet end and an open outlet end, wherein a zeolitic material according to any of the particular and preferred embodiment of the present invention as defined in the present application is provided on at least a portion of the surface of the inlet channel walls and on at least a portion of the surface of the pores within the channel walls underneath the surface of the channel walls coated with zeolitic material, wherein the portion of the inlet channel walls coated with the zeolitic material extends from the inlet end to x % of the substrate axial length with 0<x<100, and/or, preferably and wherein the zeolitic material is provided on at least a portion of the surface of the outlet channel walls and on at least a portion of the surface of the pores within the channel walls underneath the surface of the channel walls coated with the zeolitic material, wherein the portion of the outlet channel walls coated with the zeolitic material extends from the outlet end to y % of the substrate axial length with 0<y<100.

The present invention includes the following embodiments, wherein these include the specific combinations of embodiments as indicated by the respective interdependencies defined therein:

1. A process for the preparation of a zeolitic material having a CHA-type framework structure comprising $YO_2$ and $X_2O_3$, wherein said process comprises the steps of:
   (1) providing a mixture comprising one or more sources for $YO_2$, one or more sources for $X_2O_3$, one or more optionally substituted ethyltrimethylammonium cation-containing compounds, and one or more tetraalkylammonium cation $R^1R^2R^3R^4N^+$ containing compounds as structure directing agent;
   (2) crystallizing the mixture obtained in step (1) for obtaining a zeolitic material having a CHA-type framework structure;
   wherein Y is a tetravalent element and X is a trivalent element,
   wherein $R^1$, $R^2$, and $R^3$ independently from one another stand for alkyl, wherein $R^4$ stands for cycloalkyl, and
   wherein the $YO_2:X_2O_3$ molar ratio of the mixture in (1) ranges from 2 to 1,000, preferably from 3 to 500, more preferably from 5 to 300, more preferably from 10 to 100, more preferably from 15 to 50, more preferably from 20 to 40, more preferably from 23 to 35, more preferably from 25 to 30, and more preferably from 27 to 29.

2. The process of embodiment 1, wherein the mixture provided in step (1) preferably does not contain any substantial amount of a source for $Z_2O_5$, wherein Z is P, preferably P and As, wherein more preferably Z is any pentavalent element which is a source for $Z_2O_5$ in the CHA-type framework structure crystallized in step (2).

3. The process of embodiment 1 or 2, wherein $R^1$, $R^2$, and $R^3$ independently from one another stand for optionally substituted and/or optionally branched $(C_1-C_6)$alkyl, preferably $(C_1-C_5)$alkyl, more preferably $(C_1-C_4)$alkyl, more preferably $(C_1-C_3)$alkyl, and even more preferably for optionally substituted methyl or ethyl, wherein even more preferably $R^1$, $R^2$, and $R^3$ stand for optionally substituted methyl, preferably unsubstituted methyl.

4. The process of any of embodiments 1 to 3, wherein $R^4$ stands for optionally heterocyclic and/or optionally substituted 5- to 8-membered cycloalkyl, preferably for 5- to 7-membered cycloalkyl, more preferably for 5- or 6-membered cycloalkyl, wherein even more preferably $R^4$ stands for optionally heterocyclic and/or optionally substituted 6-membered cycloalkyl, preferably optionally substituted cyclohexyl, and more preferably non-substituted cyclohexyl.

5. The process of any of embodiments 1 to 4, wherein the one or more tetraalkylammonium cation $R^1R^2R^3R^4N^+$-containing compounds comprise one or more N,N,N-tri$(C_1-C_4)$alkyl-$(C_5-C_7)$cycloalkylammonium compounds, preferably one or more N,N,N-tri$(C_1-C_3)$alkyl-$(C_5-C_6)$ cycloalkylammonium compounds, more preferably one or more N,N,N-tri$(C_1-C_2)$alkyl-$(C_5-C_6)$cycloalkylammonium compounds, more preferably one or more N,N,N-tri$(C_1-C_2)$alkyl-cyclopentylammonium and/or one or more N,N,N-tri$(C_1-C_2)$alkyl-cyclohexylammonium compounds, more preferably one or more compounds selected from N,N,N-triethyl-cyclohexylammonium, N,N-diethyl-N-methyl-cyclohexylammonium, N,N-dimethyl-N-ethyl-cyclohexylammonium, N,N,N-trimethyl-cyclohexylammonium compounds, and mixtures of two or more thereof, wherein more preferably the one or more tetraalkylammonium cation $R^1R^2R^3R^4N^+$-containing compounds comprise one or more N,N,N-trimethyl-cyclohexylammonium compounds, and wherein more preferably the one or more tetraalkylammonium cation $R^1R^2R^3R^4N^+$-containing compounds consist of one or more N,N,N-trimethyl-cyclohexylammonium compounds.

6. The process of any of embodiments 1 to 5, wherein the one or more optionally substituted ethyltrimethylammonium cation-containing compounds and/or the one or more tetraalkylammonium cation $R^1R^2R^3R^4N^+$-containing compounds are salts, preferably one or more salts selected from the group consisting of halides, preferably chloride and/or bromide, more preferably chloride, hydroxide, sulfate, nitrate, phosphate, acetate, and mixtures of two or more thereof, more preferably from the group consisting of chloride, hydroxide, sulfate, and mixtures of two or more thereof, wherein more preferably the one or more optionally substituted ethyltrimethylammonium cation-containing compounds and/or the one or more tetraalkylammonium cation $R^1R^2R^3R^4N^+$-containing compounds are hydroxides and/or chlorides, and even more preferably hydroxides.

7. The process of any of embodiments 1 to 6 wherein Y is selected from the group consisting of Si, Sn, Ti, Zr, Ge, and mixtures of two or more thereof, Y preferably being Si.

8. The process of any of embodiments 1 to 7, wherein the one or more sources for $YO_2$ comprises one or more compounds selected from the group consisting of fumed silica, silica hydrosols, reactive amorphous solid silicas, silica gel, silicic acid, water glass, sodium metasilicate hydrate, sesquisilicate, disilicate, colloidal silica, silicic acid esters, and mixtures of two or more thereof, preferably from the group consisting of fumed silica, silica hydrosols, reactive amorphous solid silicas, silica gel, silicic acid, colloidal silica, silicic acid esters, and mixtures of two or more thereof, more preferably from the group consisting of fumed silica, silica hydrosols, reactive amorphous solid silicas, silica gel, colloidal silica, and mixtures of two or more thereof, wherein even more preferably the one or more sources for $YO_2$ comprises fumed silica and/or colloidal silica, preferably colloidal silica.
9. The process of any of embodiments 1 to 8, wherein X is selected from the group consisting of Al, B, In, Ga, and mixtures of two or more thereof, X preferably being Al and/or B, and more preferably being Al.
10. The process of any of embodiments 1 to 9, wherein the one or more sources for $X_2O_3$ comprises one or more compounds selected from the group consisting of alumina, aluminates, aluminum salts, and mixtures of two or more thereof, preferably from the group consisting of alumina, aluminum salts, and mixtures of two or more thereof, more preferably from the group consisting of alumina, aluminum tri($C_1$-$C_5$)alkoxide, AlO(OH), Al(OH)$_3$, aluminum halides, preferably aluminum fluoride and/or chloride and/or bromide, more preferably aluminum fluoride and/or chloride, and even more preferably aluminum chloride, aluminum sulfate, aluminum phosphate, aluminum fluorosilicate, and mixtures of two or more thereof, more preferably from the group consisting of aluminum tri($C_2$-$C_4$)alkoxide, AlO(OH), Al(OH)$_3$, aluminum chloride, aluminum sulfate, aluminum phosphate, and mixtures of two or more thereof, more preferably from the group consisting of aluminum tri($C_2$-$C_3$) alkoxide, AlO(OH), Al(OH)$_3$, aluminum chloride, aluminum sulfate, and mixtures of two or more thereof, more preferably from the group consisting of aluminum tripropoxides, AlO(OH), aluminum sulfate, and mixtures of two or more thereof, wherein more preferably the one or more sources for $X_2O_3$ comprises aluminum triisopropoxide, and wherein even more preferably the one or more sources for $X_2O_3$ consists of aluminum triisopropoxide.
11. The process of any of embodiments 1 to 10, wherein the mixture according to step (1) further comprises one or more solvents, wherein said one or more solvents preferably comprises water, preferably distilled water, wherein more preferably water is contained as the one or more solvents in the mixture according to step (1), preferably distilled water.
12. The process of embodiment 11, wherein the $H_2O$:$YO_2$ molar ratio of the mixture in (1) ranges from 1 to 40, preferably from 3 to 30, more preferably from 5 to 25, more preferably from 8 to 20, more preferably from 10 to 17, more preferably from 11 to 15, more preferably from 11.5 to 13, and more preferably from 12 to 12.5.
13. The process of any of embodiments 1 to 12, wherein the molar ratio of the one or more optionally substituted ethyltrimethylammonium cations $C_2H_5N(CH_3)_3^+$:$YO_2$ in the mixture provided according to step (1) ranges from 0.005 to 0.5, preferably from 0.01 to 0.25, more preferably from 0.03 to 0.2, more preferably from 0.05 to 0.15, more preferably from 0.07 to 0.12, more preferably from 0.08 to 0.1, and even more preferably from 0.085 to 0.095.
14. The process of any of embodiments 1 to 13, wherein the molar ratio of the one or more tetraalkylammonium cations $R^1R^2R^3R^4N^+$:$YO_2$ in the mixture provided according to step (1) ranges from 0.001 to 2.0, preferably from 0.005 to 1.0, more preferably from 0.01 to 0.5, more preferably from 0.03 to 0.3, more preferably from 0.05 to 0.25, more preferably from 0.08 to 0.22, more preferably from 0.1 to 0.2, more preferably from 0.12 to 0.18, more preferably from 0.13 to 0.17, and even more preferably from 0.14 to 0.16.
15. The process of any of embodiments 1 to 14, wherein the molar ratio $C_2H_5N(CH_3)_3$:$R^1R^2R^3R^4N^+$ of the one or more optionally substituted ethyltrimethylammonium cations to the one or more tetraalkylammonium cations $R^1R^2R^3R^4N^+$ in the mixture provided according to step (1) ranges from 0.01 to 5, preferably from 0.05 to 2, more preferably from 0.1 to 1.5, more preferably from 0.2 to 1.2, more preferably from 0.3 to 1, more preferably from 0.4 to 0.8, more preferably from 0.5 to 0.7, and even more preferably from 0.55 to 0.65.
16. The process of any of embodiments 1 to 15, wherein the crystallization in step (2) involves heating of the mixture, preferably at a temperature ranging from 90 to 250° C., preferably from 100 to 220° C., more preferably from 130 to 200° C., more preferably from 150 to 190° C., more preferably from 160 to 180° C., and even more preferably from 165 to 175° C.
17. The process of any of embodiments 1 to 16, wherein the crystallization in step (2) is conducted under solvothermal conditions, preferably under hydrothermal conditions.
18. The process of any of embodiments 1 to 17, wherein the crystallization in step (2) involves heating of the mixture for a period ranging from 3 to 120 h, preferably from 5 to 72 h, more preferably from 8 to 48 h, more preferably from 12 to 36 h, more preferably from 16 to 32 h, and even more preferably from 20 to 28 h.
19. The process of any of embodiments 1 to 18, wherein the crystallization in step (2) involves agitating the mixture, preferably by stirring.
20. The process of any of embodiments 1 to 19 further comprising one or more of the following steps of
   (3) adjusting the pH of the crystallized mixture obtained in (2), preferably to a pH ranging from 3 to 11, more preferably from 4 to 10, more preferably from 5 to 9, more preferably from 6 to 8, and more preferably from 6.5 to 7.5, and/or
   (4) isolating the zeolitic material from the crystallized mixture in (2) or (3), preferably by filtration, and/or
   (5) washing the zeolitic material obtained in (2), (3), or (4), and/or
   (6) drying and/or calcining the zeolitic material obtained in (2), (3), (4), or (5), and/or
   (7) subjecting the zeolitic material to an ion-exchange procedure,
   wherein the steps (3) and/or (4) and/or (5) and/or (6) and/or (7) can be conducted in any order, and
   wherein one or more of said steps is preferably repeated one or more times.
21. The process of embodiment 20, wherein in (6) the zeolitic material is spray dried.
22. The process of embodiment 21, wherein the zeolitic material obtained in (2) is not subject to isolation according to (4) and/or washing according to (5) prior to being subject to spray drying in (6).
23. The process of embodiment 21 or 22, wherein the crystallized mixture obtained in (2) is directly subject to spray drying in (6).
24. The process of any of embodiments 20 to 23, wherein in the at least one step (7) one or more ionic non-framework elements contained in the zeolite framework is ion-exchanged, preferably against one or more cations and/or cationic elements, wherein the one or more cation and/or cationic elements are preferably selected from the group consisting of $H^+$, $NH_4^+$, Sr, Zr, Cr, Mg, Mo, Fe, Co, Ni, Cu, Zn, Ru, Rh, Pd, Ag, Os, Ir, Pt, Au, and mixtures of two or more thereof, more preferably from the group consisting of $H^+$, $NH_4^+$, Sr, Cr, Mo, Fe, Co, Ni, Cu, Zn, Ag, and mixtures of two or more thereof, more preferably from the group consisting of $H^+$, $NH_4^+$, Cr, Mg, Mo, Fe, Ni, Cu, Zn, Ag, and mixtures of two or more thereof, more preferably from the group consisting of Mg, Mo, Fe, Ni, Cu, Zn, Ag, and mixtures of two or more thereof, wherein more preferably the one or more cation and/or cationic elements comprise Cu and/or Fe, preferably Cu, wherein even more preferably the one or more cation and/or cationic elements consist of Cu and/or Fe, preferably of Cu, and wherein the one or more ionic non-framework elements preferably comprise $H^+$ and/or an alkali metal, the alkali metal preferably being selected from the group consisting of Li, Na, K, Cs, and combinations of two or more thereof, more preferably from the group consisting of Li, Na, K, and combinations of two or more thereof, wherein more preferably the alkali metal is Na and/or K, even more preferably Na.

25. The process of any of embodiments 1 to 24, wherein the mixture provided in step (1) does not contain any substantial amount of a trimethyl benzyl ammonium containing compound, preferably of a trialkyl benzyl ammonium compound wherein preferably the mixture provided in step (1) does not contain any substantial amount of an organotemplate other than the one or more tetraalkylammonium cation $R^1R^2R^3R^4N^+$-containing compounds as structure directing agent, wherein more preferably the mixture provided in step (1) does not contain any substantial amount of a structure directing agent other than the one or more tetraalkylammonium cation $R^1R^2R^3R^4N^+$-containing compounds, and wherein even more preferably, the mixture provided in step (1) only contains one or more N,N,N-trimethyl-cyclohexylammonium compounds and preferably N,N,N-trimethyl-cyclohexylammonium hydroxide as structure directing agent for the crystallization of a zeolitic material having a CHA-type framework structure in step (2).

26. The process of any of embodiments 1 to 25, wherein the mixture provided in step (1) further comprises seed crystals, preferably seed crystals comprising a zeolitic material having the CHA-type framework structure, wherein the zeolitic material of the seed crystals is preferably obtainable and/or obtained according to any one of embodiments 1 to 22.

27. The process of embodiment 26, wherein the amount of seed crystals in the mixture according to step (1) ranges from 0.1 to 20 wt.-% based on 100 wt.-% of $YO_2$ in the at least one source for $YO_2$, preferably from 0.5 to 15 wt.-%, more preferably from 1 to 12 wt.-%, more preferably from 1.5 to 10 wt.-%, more preferably from 2 to 8 wt.-%, more preferably from 2.5 to 6 wt.-%, more preferably from 3 to 5 wt.-%, and even more preferably from 3.5 to 4.5 wt.-% based on 100 wt.-% of $YO_2$.

28. A synthetic zeolitic material having a CHA-type framework structure obtainable and/or obtained according to the process of any of embodiments 1 to 27.

29. A synthetic zeolitic material having a CHA-type framework structure, preferably obtainable and/or obtained according to the process of any of embodiments 1 to 27, wherein the CHA-type framework structure comprises $YO_2$ and $X_2O_3$, wherein Y is a tetravalent element and X is a trivalent element, and wherein the IR-spectrum of the zeolitic material comprises:
a first absorption band (B1) ranging from 3,720 to 3,750 $cm^{-1}$; and
a second absorption band (B2) ranging from 1,850 to 1,890 $cm^{-1}$;
wherein the ratio of the maximum absorbance of the first absorption band to the second absorption band B1:B2 ranges from 1 to 2.5, preferably from 1.2 to 2, more preferably from 1.25 to 1.9, more preferably from 1.3 to 1.8, more preferably from 1.35 to 1.75, more preferably from 1.4 to 1.7, more preferably from 1.45 to 1.65, more preferably from 1.48 to 1.6, more preferably from 1.5 to 1.58, and more preferably from 1.52 to 1.56.

30. The zeolitic material of embodiment 28 or 29, wherein the particle size D10 of the zeolitic material ranges from 50 to 400 nm, preferably from 90 to 360 nm, more preferably from 120 to 330 nm, more preferably from 150 to 300 nm, more preferably from 180 to 270 nm, and more preferably from 200 to 250 nm.

31. The zeolitic material of embodiment 28 or 29, wherein the average particle size D50 of the zeolitic material ranges from 150 to 600 nm, preferably from 200 to 550 nm, more preferably from 240 to 510 nm, more preferably from 270 to 480 nm, more preferably from 300 to 450 nm, more preferably from 330 to 420 nm, and more preferably from 350 to 400 nm.

32. The zeolitic material of embodiment 28 or 29, wherein the particle size D90 of the zeolitic material ranges from 450 to 950 nm, preferably from 500 to 900 nm, more preferably from 540 to 850 nm, more preferably from 570 to 800 nm, more preferably from 600 to 770 nm, more preferably from 630 to 740 nm, more preferably from 650 to 720 nm, and more preferably from 670 to 700 nm.

33. The zeolitic material of embodiment 28 or 29, wherein the particle size D10 of the zeolitic material ranges from 150 to 300 nm, more preferably from 180 to 270 nm, and more preferably from 200 to 250 nm, wherein the average particle size D50 of the zeolitic material ranges from 300 to 450 nm, preferably from 330 to 420 nm, and more preferably from 350 to 400 nm, and wherein the particle size D90 of the zeolitic material ranges from 500 to 900 nm, preferably from 570 to 800 nm, more preferably from 630 to 740 nm, and more preferably from 670 to 700 nm.

34. The zeolitic material of any of embodiments 28 to 33, wherein the $^7Al$ MAS NMR of the zeolitic material comprises:
a first peak (P1) ranging from 55.0 to 61.5 ppm, preferably from 56.0 to 60.5 ppm, more preferably from 56.5 to 60.0 ppm, more preferably from 57.0 to 59.5 ppm, more preferably from 57.5 to 59.0 ppm, more preferably from 57.8 to 58.7 ppm, more preferably from 58.0 to 58.5 ppm, and even more preferably from 58.4 to 58.5 ppm; and
a second peak (P2) ranging from −0.0 to −7.0 ppm, preferably from −0.5 to −6.0 ppm, more preferably from −1.0 to −5.5 ppm, more preferably from −1.5 to −5.0 ppm, more preferably from −2.0 to −4.5 ppm, more preferably from −2.3 to −4.1 ppm, more preferably from −2.5 to −3.8 ppm, more preferably from −2.7 to −3.6 ppm, and even more preferably from −2.8 to −3.4 ppm;
wherein the integration of the first and second peaks in the $^{27}Al$ MAS NMR of the zeolitic material offers a ratio of the integration values P1:P2 ranges from 1:(0.005-

0.2), preferably from 1:(0.01-0.18), more preferably from 1:(0.03-0.16), more preferably from 1:(0.05-0.15), more preferably from 1:(0.08-0.14), more preferably from 1:(0.09-0.13), and even more preferably from 1:(0.1-0.12).

35. The zeolitic material of any of embodiments 28 to 34, wherein the $^{29}Si$ MAS NMR of the zeolitic material comprises:
   a first peak (P'1) ranging from −102.0 to −106.0 ppm, preferably from −102.5 to −105.5 ppm, preferably from −103.0 to −105.0 ppm, preferably from −103.2 to −104.8 ppm, preferably from −103.4 to −104.5 ppm, preferably from −103.6 to −104.3 ppm, and even more preferably from −103.8 to −104.1 ppm; and
   a second peak (P'2) ranging from −108.0 to −112.5 ppm, preferably from −109.0 to −111.5 ppm, preferably from −109.5 to −111.0 ppm, preferably from −110.0 to −110.5 ppm, and even more preferably from −110.1 to −110.3 ppm,
   wherein the integration of the first and second peaks in the $^{2}Si$ MAS NMR of the zeolitic material offers a ratio of the integration values P'1:P'2 ranging from 0.1 to 0.9, preferably from 0.2 to 0.7, more preferably from 0.25 to 0.6, more preferably from 0.3 to 0.5, more preferably from 0.35 to 0.45, more preferably from 0.37 to 0.43, and even more preferably from 0.39 to 0.41.

36. The zeolitic material of any of embodiments 28 to 35, wherein the CHA-type framework does not contain any substantial amount of P and/or As, preferably one or more elements selected from the group consisting of P, As, V, and combinations of two or more thereof, more preferably one or more elements selected from the group consisting of P, As, Sb, Bi, V, Nb, Ta, and combinations of two or more thereof, wherein even more preferably the framework structure does not contain any substantial amount of any pentavalent elements Z as framework element, and wherein the zeolitic material preferably does not comprise SSZ-13 and/or SSZ-15.

37. The zeolitic material of any of embodiments 28 to 36, wherein the $YO_2:X_2O_3$ molar ratio ranges from 4 to 200, preferably from 10 to 120, more preferably from 15 to 80, more preferably from 18 to 50, more preferably from 20 to 30, more preferably from 22 to 28, and even more preferably from 24 to 26.

38. The zeolitic material of any of embodiments 28 to 37, wherein Y is selected from the group consisting of Si, Sn, Ti, Zr, Ge, and mixtures of two or more thereof, Y preferably being Si.

39. The zeolitic material of any of embodiments 28 to 38, wherein X is selected from the group consisting of Al, B, In, Ga, and mixtures of two or more thereof, X preferably being Al and/or B, and more preferably being Al.

40. The zeolitic material of any of embodiments 28 to 39, wherein the zeolitic material comprises one or more cation and/or cationic elements as ionic non-framework elements, said one or more cation and/or cationic elements preferably comprising one or more selected from the group consisting of $H^+$, $NH_4^+$, Sr, Zr, Cr, Mg, Mo, Fe, Co, Ni, Cu, Zn, Ru, Rh, Pd, Ag, Os, Ir, Pt, Au, and mixtures of two or more thereof, more preferably from the group consisting of $H^+$, $NH_4^+$, Sr, Cr, Mo, Fe, Co, Ni, Cu, Zn, Ag, and mixtures of two or more thereof, more preferably from the group consisting of $H^+$, $NH_4^+$, Cr, Mg, Mo, Fe, Ni, Cu, Zn, Ag, and mixtures of two or more thereof, more preferably from the group consisting of Mg, Mo, Fe, Ni, Cu, Zn, Ag, and mixtures of two or more thereof, wherein more preferably the one or more cation and/or cationic elements comprise Cu and/or Fe, preferably Cu, wherein even more preferably the one or more cation and/or cationic elements consist of Cu and/or Fe, preferably of Cu.

41. The zeolitic material of embodiment 40, wherein the one or more cations and/or cationic elements are contained in the zeolitic material in an amount ranging from 0.01 to 25 wt.-% based on 100 wt.-% of $YO_2$ comprised in the zeolitic material, preferably from 0.05 to 15.0 wt.-%, more preferably from 0.1 to 10.0 wt.-%, more preferably from 0.5 to 6.0 wt.-%, more preferably from 1.0 to 4.0 wt.-%, more preferably from 1.5 to 3.5 wt.-%, more preferably from 2.0 to 3.0 wt.-%, more preferably from 2.3 to 2.7 wt.-%.

42. The zeolitic material of any of embodiments 28 to 41, wherein the BET surface area of the zeolitic material determined according to ISO 9277:2010 ranges from 200 to 950 $m^2/g$, preferably from 400 to 850 $m^2/g$, more preferably from 500 to 800 $m^2/g$, more preferably from 550 to 750 $m^2/g$, more preferably from 580 to 700 $m^2/g$, more preferably from 610 to 680 $m^2/g$, more preferably from 635 to 665 $m^2/g$.

43. The zeolitic material of any of embodiments 28 to 42, wherein the micropore volume of the zeolitic material determined according to DIN 66133 ranges from 0.5 to 3 $cm^3/g$, preferably from 0.8 to 2.5 $cm^3/g$, more preferably from 1 to 2.2 $cm^3/g$, more preferably from 1.1 to 2 $cm^3/g$, more preferably from 1.2 to 1.8 $cm^3/g$, more preferably from 1.3 to 1.7 $cm^3/g$, more preferably from 1.4 to 1.6 $cm^3/g$, and more preferably from 1.45 to 1.55 $cm^3/g$.

44. A catalyzed soot filter (CSF) for selective catalytic reduction (SCR), wherein the CSF comprises a porous wall flow substrate,
   the wall flow substrate comprising an inlet end, an outlet end, a substrate axial length extending between the inlet end and the outlet end, and a plurality of channels defined by internal walls of the wall flow substrate, wherein the plurality of channels comprise inlet channels having an open inlet end and a closed outlet end, and outlet channels having a closed inlet end and an open outlet end,
   wherein a zeolitic material according to any of embodiments 28 to 43 is provided on at least a portion of the surface of the inlet channel walls and on at least a portion of the surface of the pores within the channel walls underneath the surface of the channel walls coated with zeolitic material, wherein the portion of the inlet channel walls coated with the zeolitic material extends from the inlet end to x % of the substrate axial length with 0<x<100,
   and/or, preferably and
   wherein the zeolitic material is provided on at least a portion of the surface of the outlet channel walls and on at least a portion of the surface of the pores within the channel walls underneath the surface of the channel walls coated with the zeolitic material, wherein the portion of the outlet channel walls coated with the zeolitic material extends from the outlet end to y % of the substrate axial length with 0<y<100.

45. Use of a synthetic zeolitic material having a CHA-type framework structure according to any of embodiments 28 to 44 as a molecular sieve, as an adsorbent, for ion-exchange, or as a catalyst and/or as a catalyst support, preferably as a catalyst for the selective catalytic reduction (SCR) of nitrogen oxides $NO_x$; for the storage and/or adsorption of $CO_2$; for the oxidation of $NH_3$, in particular for the oxidation of $NH_3$ slip in diesel systems; for the decomposition of $N_2O$; as an additive in fluid catalytic cracking (FCC) processes; and/or as a catalyst in organic conversion reactions, preferably in the conversion of alcohols to olefins, and more preferably in methanol to olefin (MTO) catalysis; more preferably for the selective catalytic reduction (SCR) of nitrogen oxides $NO_x$, and more preferably for the selective catalytic reduction (SCR) of nitrogen oxides $NO_x$ in exhaust gas from a combustion engine, preferably from a diesel engine or from a lean burn gasoline engine.

EXAMPLES

Figure 1A:
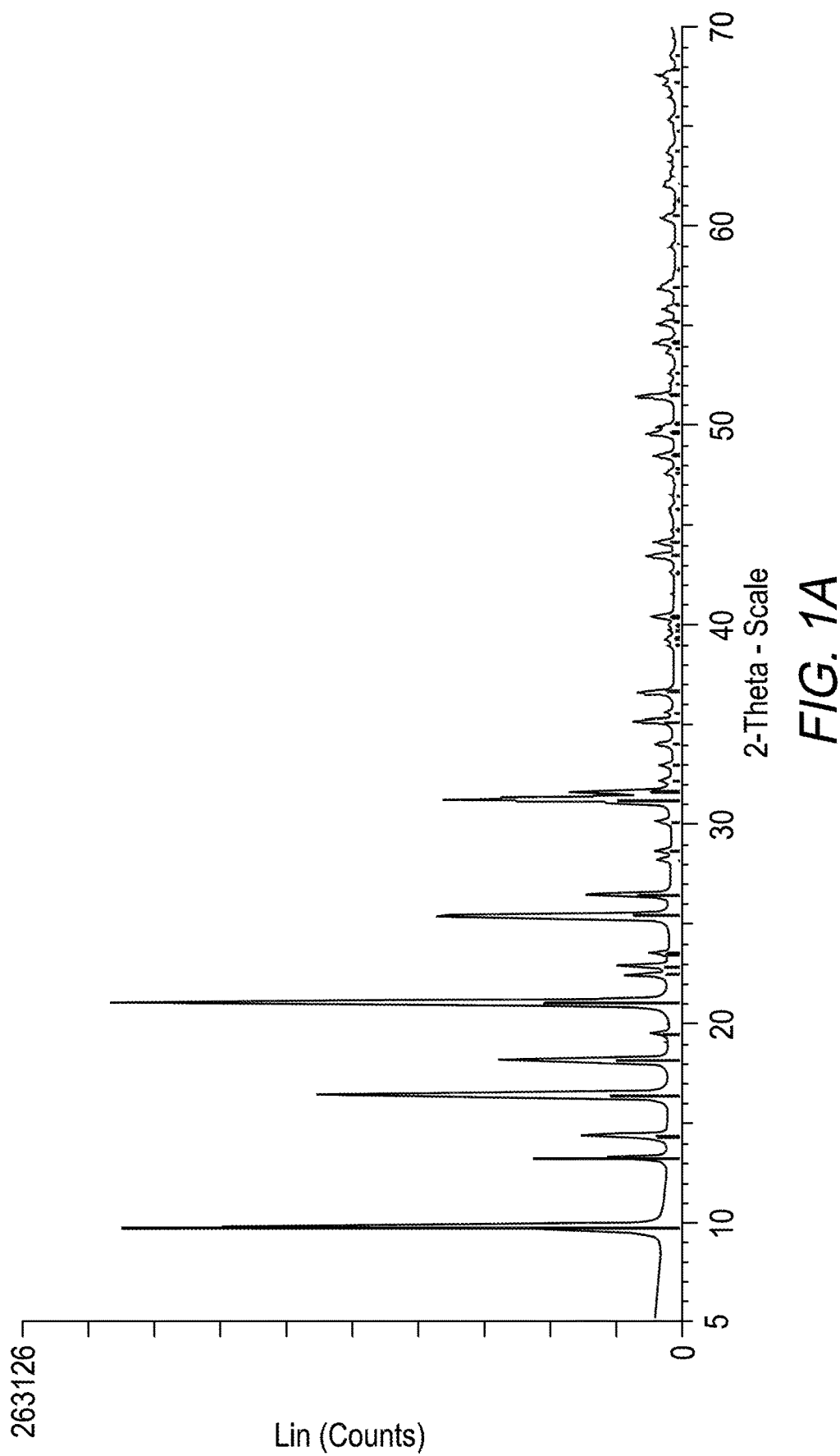
FIGS. 1a, 2a, 3a, and 5a display the X-ray diffraction patterns (measured using Cu K alpha-1 radiation) of the calcined products obtained according to Examples 1-3 and Comparative Example 2, respectively. For comparative purposes, the line pattern of the CHA type structure is indicated in the diffractogram of the respective figures. In the figure, the angle 2 theta in ° is shown along the abscissa and the intensities are plotted along the ordinate.

X-ray diffraction experiments on the powdered materials were performed using an Advance D8 Series 2 Diffractometer (Bruker/AXS) equipped with a Sol-X detector using the Cu K alpha-1 radiation.

$^{27}Al$ MAS solid-state NMR experiments were measured by direct excitation with 15°-pulse under 10 kHz Magic Angle Spinning using 250 ms recycle delay and 20 ms acquisition. The data was processed with 50 Hz exponential line broadening.

$^{29}Si$ MAS solid-state NMR experiments were performed using a Bruker Avance spectrometer with 300 MHz $^1H$ Larmor frequency (Bruker Biospin, Germany). Spectra were processed using Bruker Topspin with 30 Hz exponential line broadening, manual phasing, and manual baseline correction over the full spectrum width. Spectra were referenced with the polymer Q8M8 as an external secondary standard, by setting the resonance of the trimethylsilyl M group to 12.5 ppm.

The IR-spectra were obtained from samples free of a carrier material, wherein said sample were heated at 300° C. in high vacuum for 3 h prior to measurement. The measurements were performed using a Nicolet 6700 spectrometer in a high vacuum measurement cell with $CaF_2$ windows. The obtained data was transformed to absorbance values, and the analysis was performed on the spectra after base line correction.

The particle size distribution of the samples was performed by dispersing 0.1 g of the zeolite powder in 100 g $H_2O$ and treating by ultrasound for 10 minutes. The dynamic light scattering was performed on a Zetasizer Nano ZS with the Malvern Zeta Sizer Software. Version 6.34, applying 5 runs à 10 second measurement time for each sample. The given values are the average particle size by number in nanometer.

The micropore volume of the calcined samples was determined according to DIN 66133.

Example 1: Preparation of a Zeolitic Material Having the CHA Framework Structure Using Trimethylcyclohexylammonium and Ethyltrimethylammonium 530.71 g N,N,N-trimethylcyclohexylammoniumhydroxide (20 wt-% solution in $H_2O$) were mixed with 66.74 g of aluminiumtriisopropylate and 215.66 g ethyltrimethylammoniumhydroxide (20 wt-% solution in $H_2O$). Afterwards, 686.93 g LUDOX AS 40 (40 wt-% colloidal solution in $H_2O$) and 11.49 g CHA seeds were added to the stirred mixture. The resulting gel was placed in a stirred autoclave with a total volume of 2.5 L. The autoclave was heated within 7 h to 170° C. The temperature was kept constant for 72 h. Afterwards the autoclave was cooled down to room temperature. Then, the solids were separated by filtration and intensive washing until the washwater had a pH of 7. Finally the solid was dried for 10 hours at 120° C. Solid yield=335 g. The material was calcined at 550° C. for 5 hours.

The characterization of the calcined material via XRD is displayed in FIG. 1a and displays the CHA-type framework structure of the product and afforded an average crystal size of 101 nm and a crystallinity of 87%. The calcined material displayed a BET surface area of 665 $m^2/g$, a pore volume of 1.29 $cm^3/g$ and a median pore width of 2.76 nm. The elemental analysis of the calcined material showed 93.4 wt-% $SiO_2$, 6.5 wt-% $Al_2O_3$, and 0.1 wt-% $Na_2O$ in the sample, thus affording an $SiO_2:Al_2O_3$ atomic ratio (SAR) of 24.5.

Figure 1B:
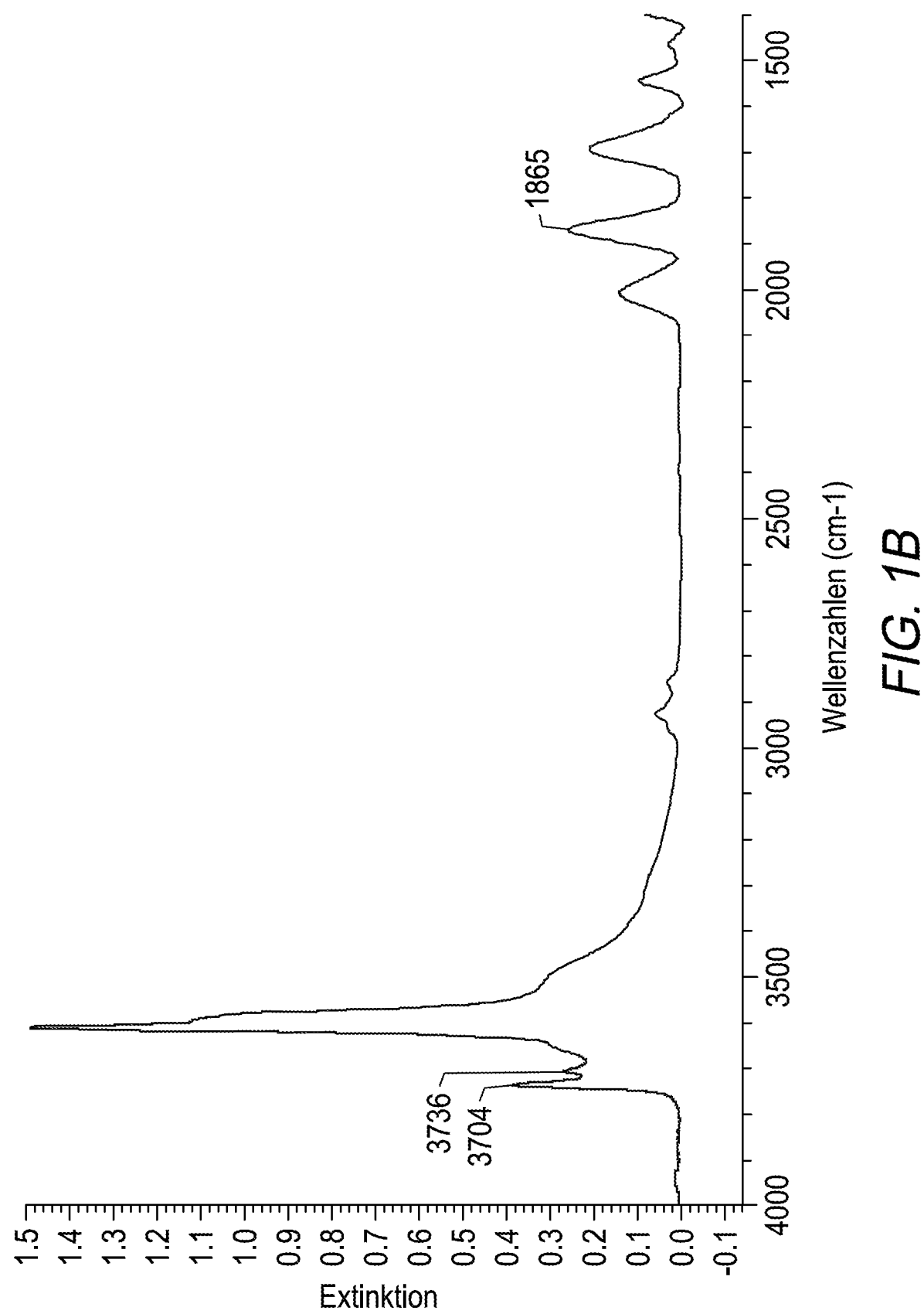
FIGS. 1b, 2b, 3b, 4a, and 5b display the IR-spectra obtained for the calcined products obtained according to Examples 1-3, and Comparative Examples 1 and 2, respectively. In the figures, the wavenumbers in $cm^{-1}$ is shown along the abscissa, and the absorbance is plotted along the ordinate.

The IR-spectrum of the calcined sample is shown in FIG. 1b, wherein amongst others absorption bands having maxima at 3,736 $cm^{-1}$ and 1,865 $cm^{-1}$ may be seen, which display a ratio of maximum absorption of the former to the latter of 1.48.

The particle size distribution of the calcined sample afforded a D10 value of 0.21 μm, a D50 value of 0.27 μm, and a D90 value of 0.67 μm.

Figure 1C:
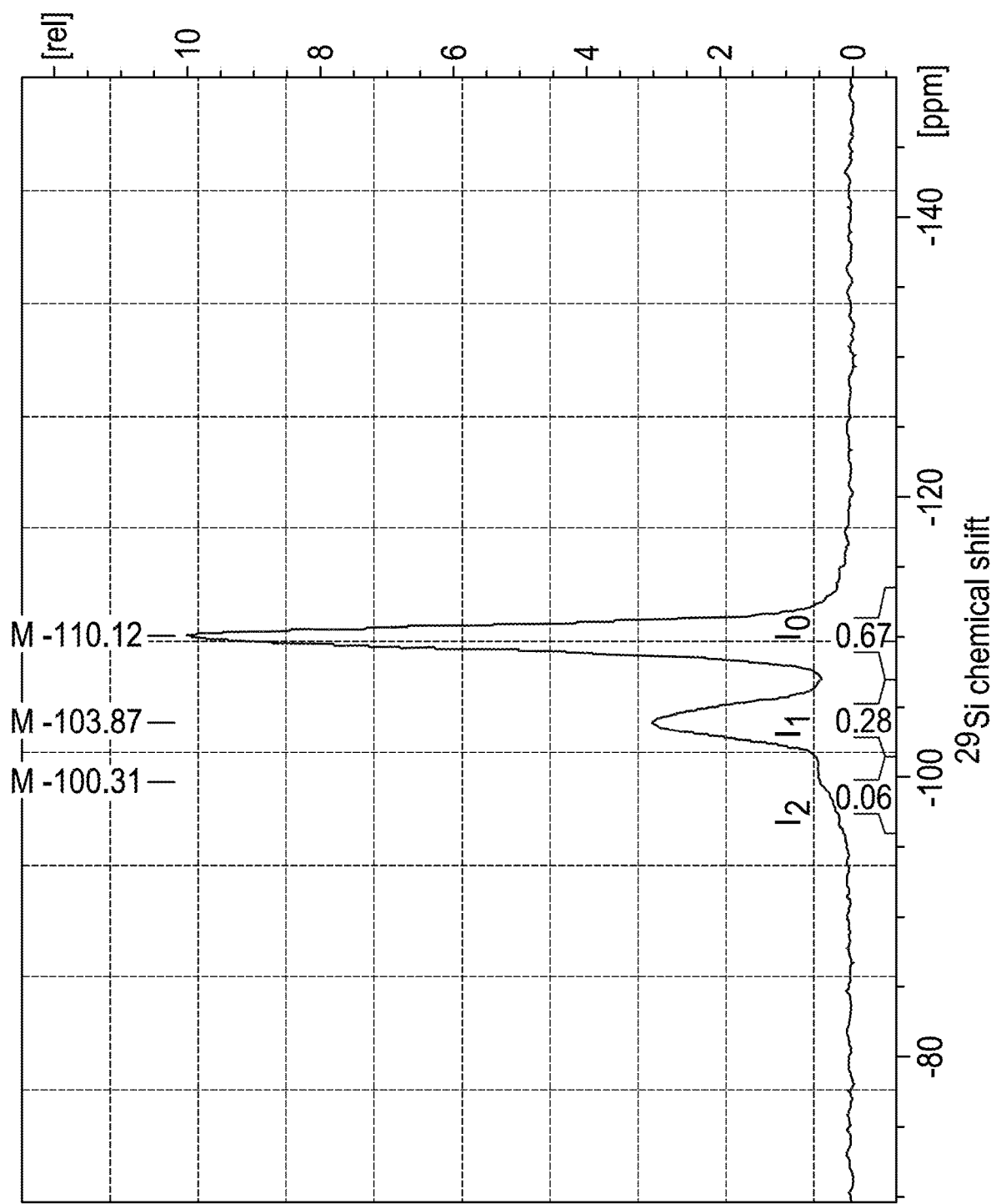
FIGS. 1c. 2c, 3c, 4b, and 5c display the $^{27}Al$ MAS solid-state NMR spectra obtained for the calcined products of Examples 1-3 and Comparative Examples 1 and 2, respectively. In the figures, the chemical shift in ppm is shown along the abscissa, and the relative intensity in arbitrary units is plotted along the ordinate. Furthermore, the integration of the relative peak intensities is displayed above the abscissa for the relevant peaks, of which the ppm-values for the maxima is indicated above the respective peak preceded by the indication "M" for maximum.

The $^{29}Si$ MAS NMR of the calcined zeolitic material is displayed in FIG. 1c and displays peaks at −103.87 and −110.12 ppm, wherein the integration of the peaks offers relative intensities of 0.418 and 1 for the signals, respectively.

Figure 1D:
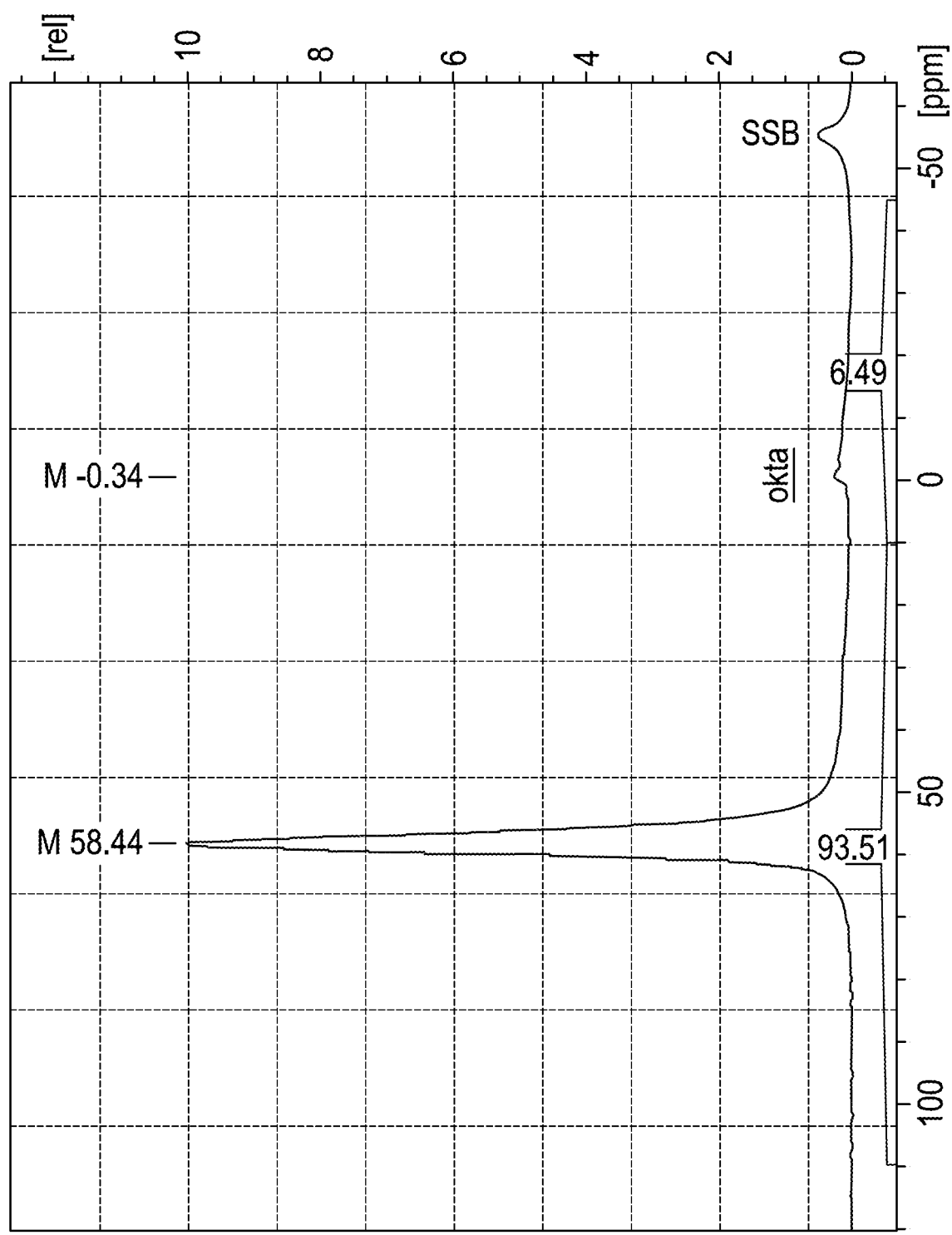
FIGS. 1d, 2d, 3d, 4c, and 5d display the $^{29}Al$ MAS solid-state NMR spectra obtained for the calcined products of Examples 1-3 and Comparative Examples 1 and 2, respectively. In the figures, the chemical shift in ppm is shown along the abscissa, and the relative intensity in arbitrary units is plotted along the ordinate. Furthermore, the integration of the relative peak intensities is displayed above the abscissa for the relevant peaks, of which the ppm-values for the maxima is indicated above the respective peak preceded by the indication "M" for maximum.

The $^{27}Al$ MAS NMR of the calcined zeolitic material is displayed in FIG. 1d and displays peaks at 58.44 and −0.34 ppm, wherein the integration of the peaks offers relative intensities of 1 and 0.069 for the signals, respectively.

Example 2: Preparation of a Zeolitic Material Having the CHA Framework Structure Using Trimethylcyclohexylammonium and Ethyltrimethylammonium 530.71 g N,N,N-trimethylcyclohexylammoniumhydroxide (20 wt-% solution in $H_2O$) were mixed with 66.74 g of aluminiumtriisopropylate and 215.66 g ethyltrimethylammoniumhydroxide (20 wt-% solution in $H_2O$). Afterwards, 686.93 g LUDOX AS 40 (40 wt-% colloidal solution in $H_2O$) and 11.49 g CHA seeds were added to the stirred mixture. The resulting gel was placed in a stirred autoclave with a total volume of 2.5 L. The autoclave was heated within 7 h to 170° C. The temperature was kept constant for 24 h. Afterwards the autoclave was cooled down to room temperature. Then, the solids were separated by filtration and intensive washing until the washwater had a pH of 7. Finally the solid was dried for 10 hours at 120° C. Solid yield=337 g. The material was calcined at 550° C. for 5 hours.

Figure 2A:
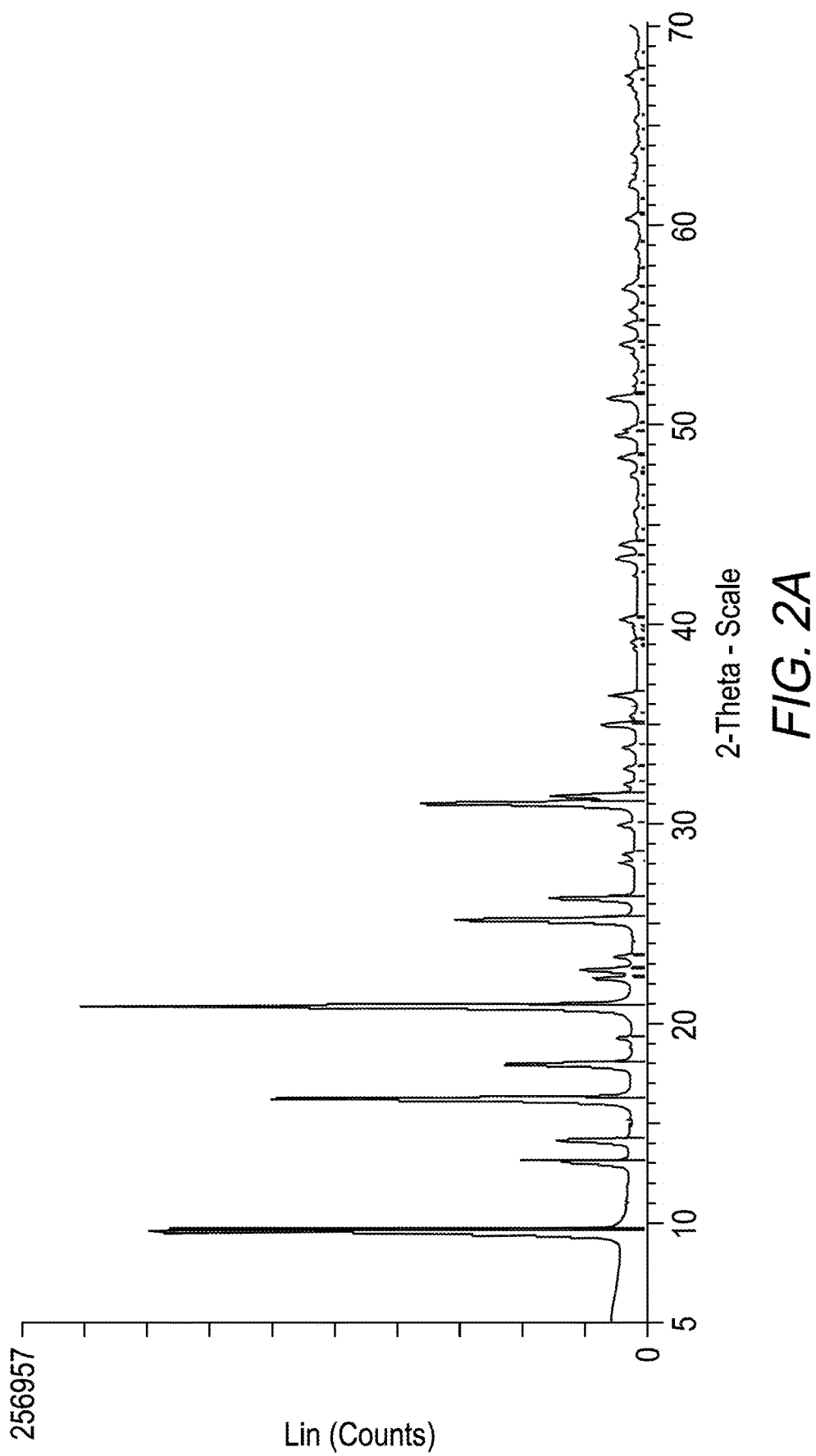

The characterization of the calcined material via XRD is displayed in FIG. 2a and displays the CHA-type framework structure of the product and afforded an average crystal size of 96 nm and a crystallinity of 86%. The calcined material displayed a BET surface area of 635 $m^2/g$, a pore volume of 1.80 $cm^3/g$ and a median pore width of 1.31 nm. The elemental analysis of the calcined material showed 93.4 wt-% $SiO_2$, 6.2 wt-% $Al_2O_3$, and 0.1 wt-% $Na_2O$ in the sample, thus affording an $SiO_2:Al_2O_3$ atomic ratio (SAR) of 24.7.

Figure 2B:
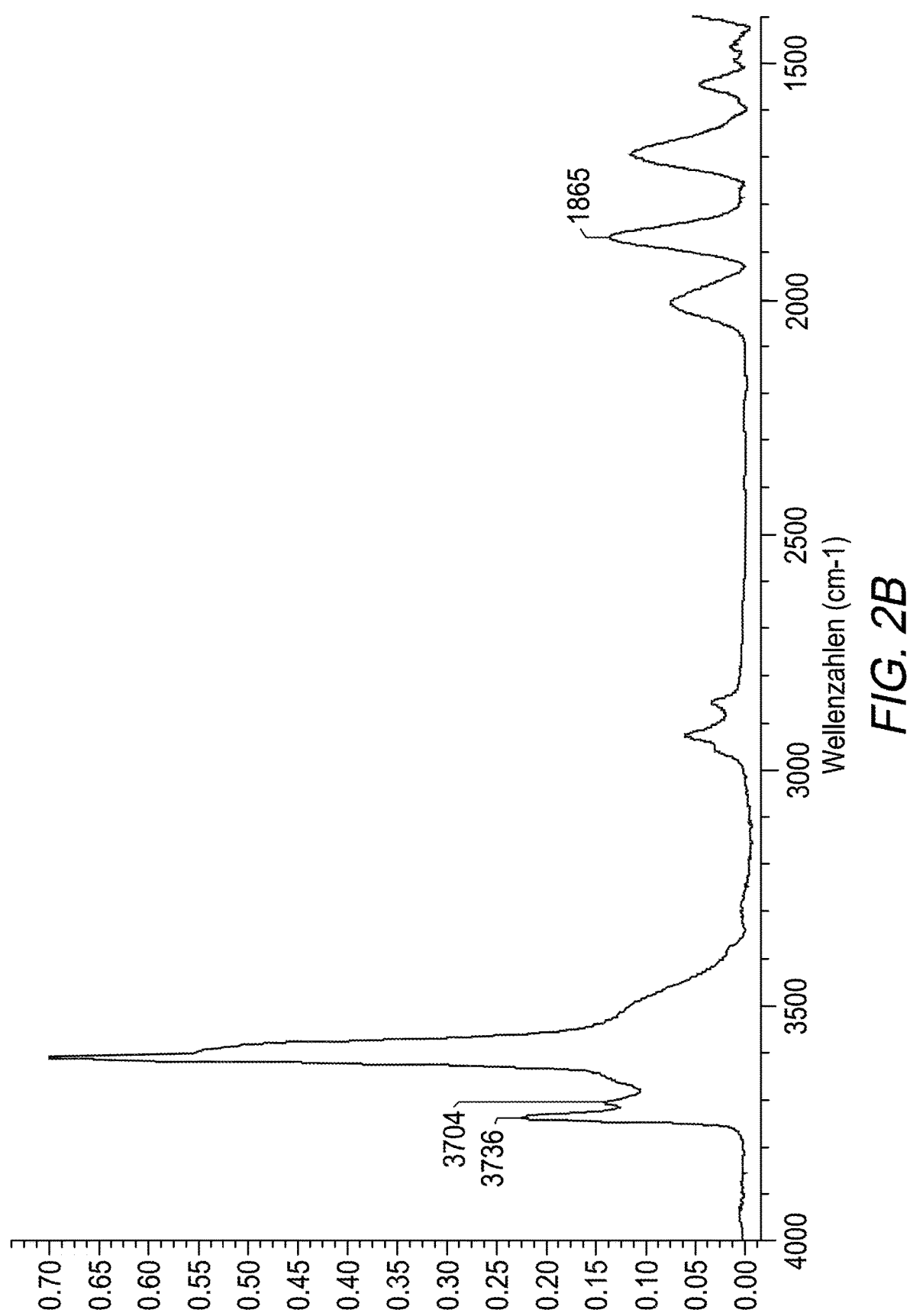

The IR-spectrum of the calcined sample is shown in FIG. 2b, wherein amongst others absorption bands having maxima at 3,736 $cm^{-1}$ and 1,865 $cm^{-1}$ may be seen, which display a ratio of maximum absorption of the former to the latter of 1.64.

The particle size distribution of the calcined sample afforded a D10 value of 0.30 μm, a D50 value of 0.48 μm, and a D90 value of 0.70 μm.

Figure 2C:
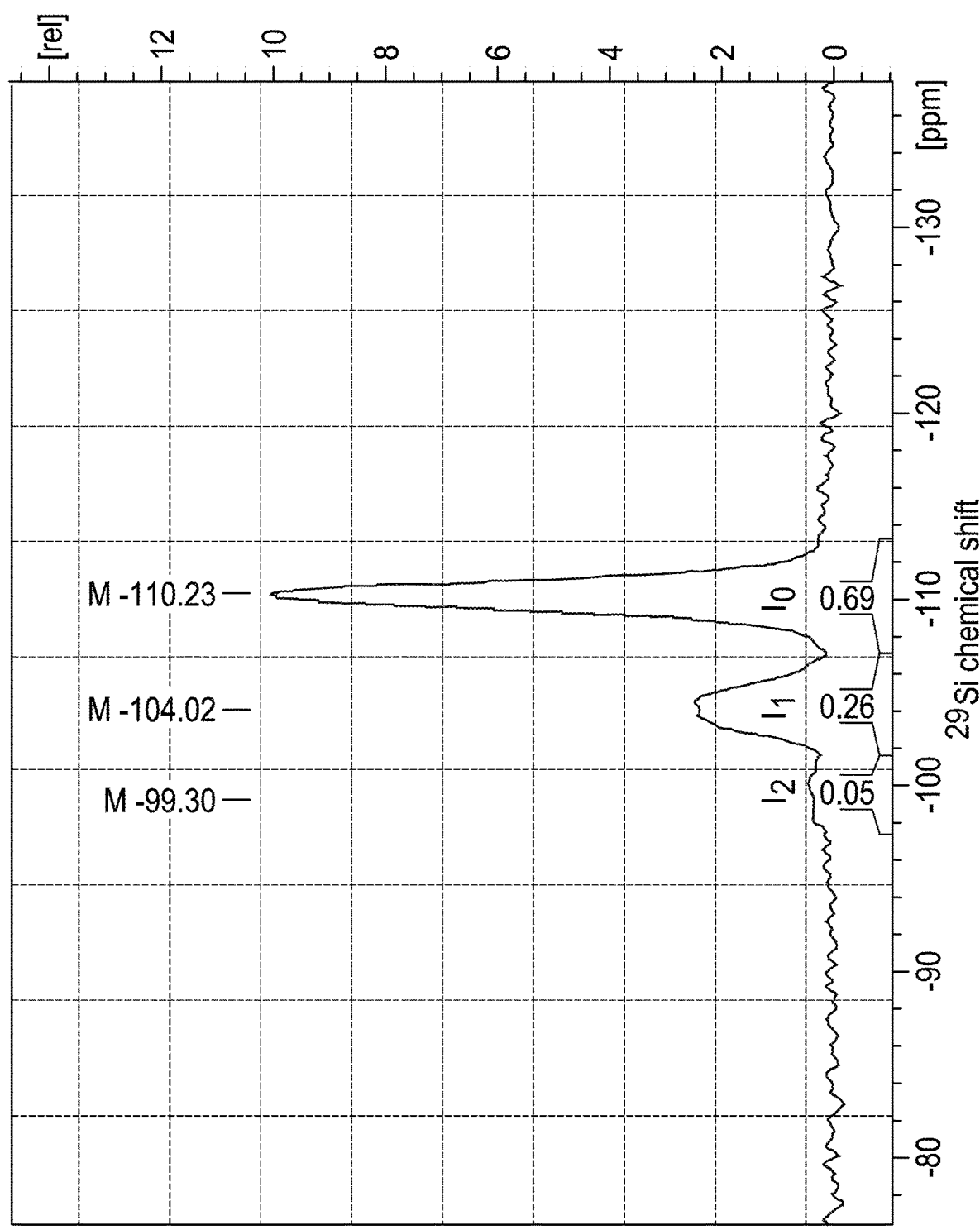

The $^{29}Si$ MAS NMR of the calcined zeolitic material is displayed in FIG. 2c and displays peaks at −104.02 and −110.23 ppm, wherein the integration of the peaks offers relative intensities of 0.377 and 1 for the signals, respectively.

Figure 2D:
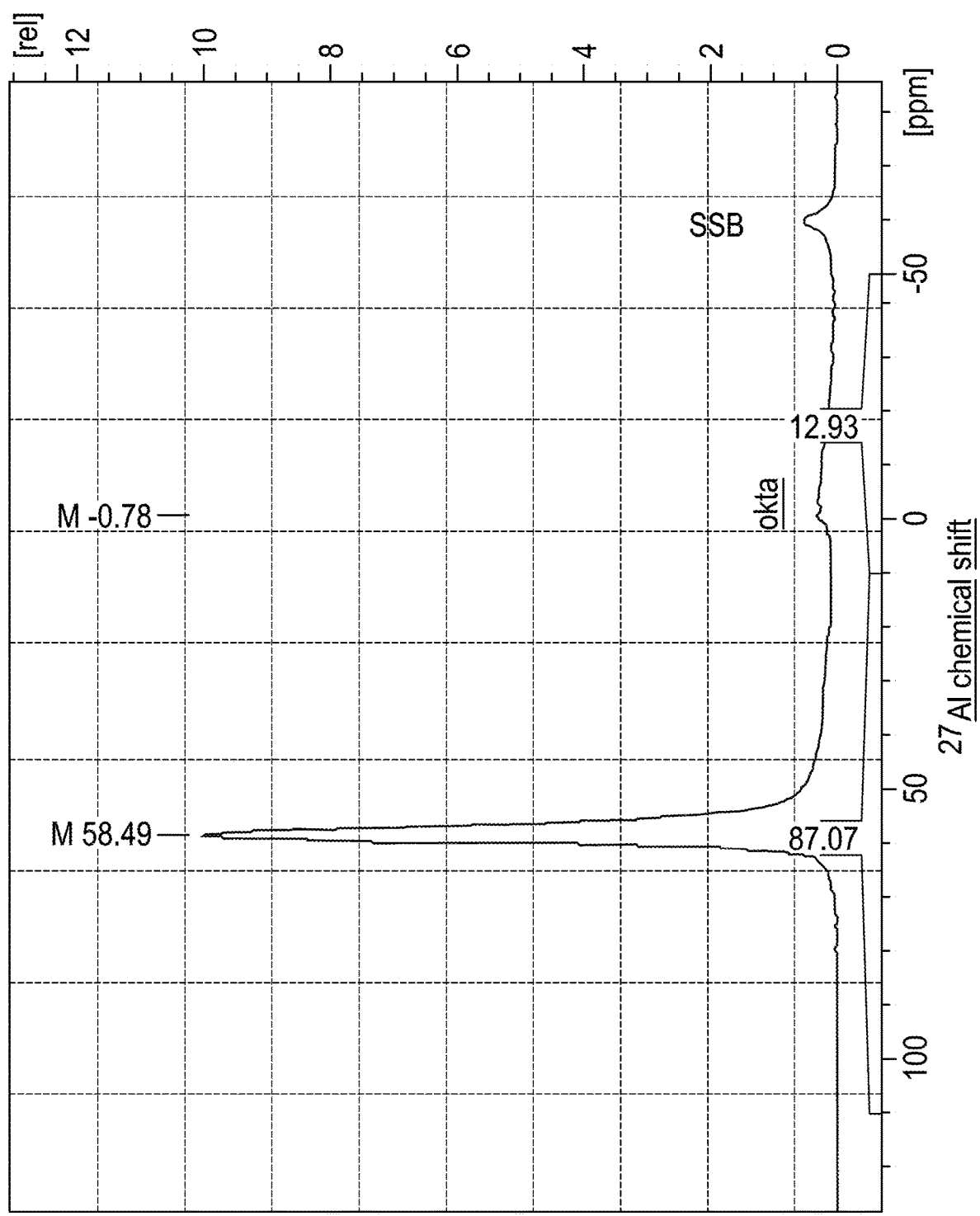

The $^{27}Al$ MAS NMR of the calcined zeolitic material is displayed in FIG. 2d and displays peaks at 58.49 and −0.78 ppm, wherein the integration of the peaks offers relative intensities of 1 and 0.149 for the signals, respectively.

Example 3: Preparation of a Zeolitic Material Having the CHA Framework Structure Using Trimethylcyclohexylammonium and Ethyltrimethylammonium 12.38 kg N,N,N-trimethylcyclohexylammoniumhydroxide (20 wt-% solution in $H_2O$) were mixed with 1.56 kg of aluminiumtriisopropylate and 5.03 kg ethyltrimethylammoniumhydroxide (20 wt-% solution in $H_2O$). Afterwards, 16.03 kg LUDOX AS 40 (40 wt-% colloidal solution in $H_2O$) and 268.12 g CHA seeds were added to the stirred mixture. The resulting gel was placed in a stirred autoclave with a total volume of 60 L. The autoclave was heated within 7 h to 170° C. The temperature was kept constant for 24 h. Afterwards the autoclave was cooled down to room temperature. Then, the solids were separated by filtration and intensive washing until the washwater had a pH of 7. Finally the solid was dried for 10 hours at 120° C. Solid yield=7.5 kg. The material was calcined at 550° C. for 5 hours.

Figure 3A:
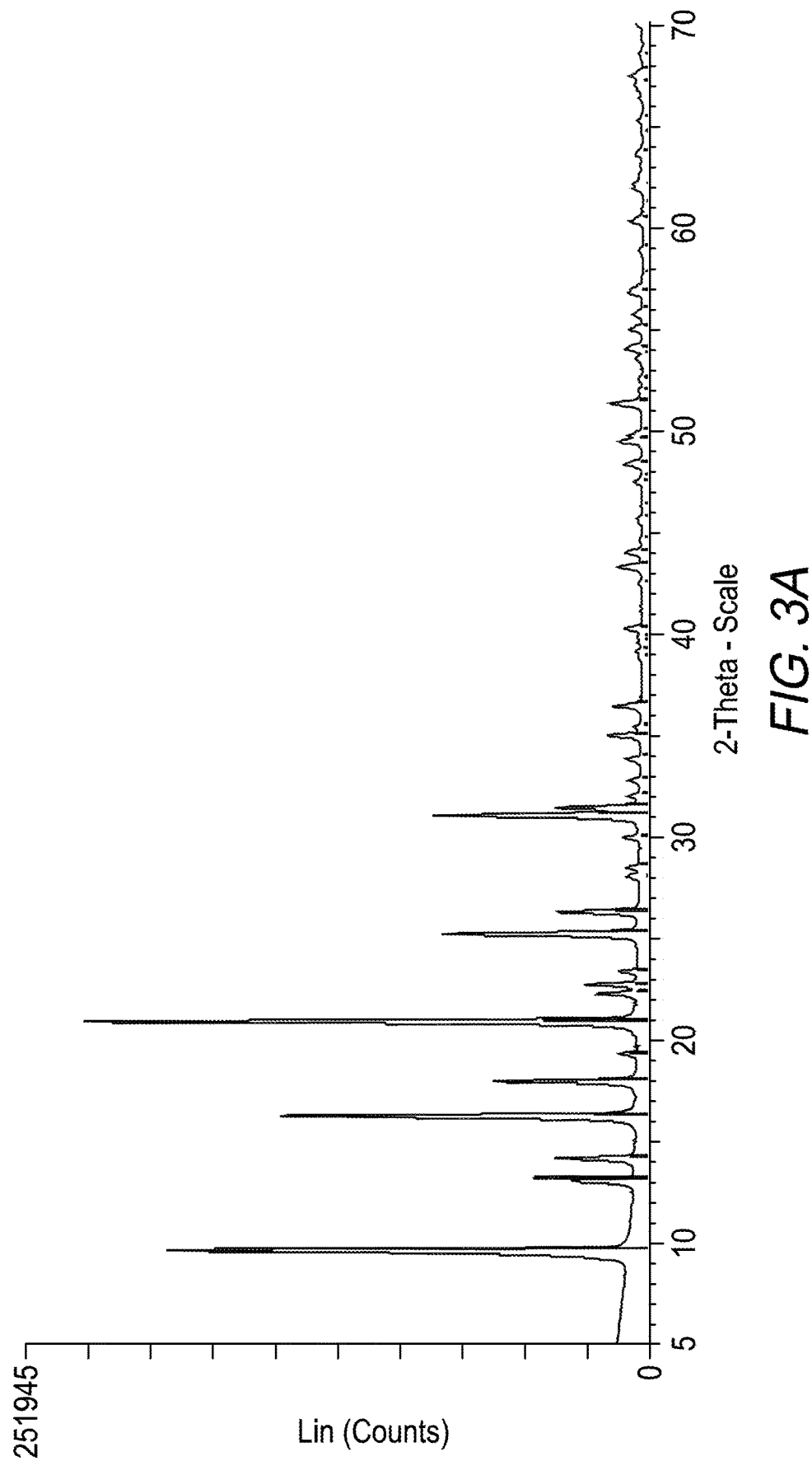

The characterization of the calcined material via XRD is displayed in FIG. 3a and displays the CHA-type framework structure of the product and afforded an average crystal size of 106 nm and a crystallinity of 90%. The calcined material displayed a BET surface area of 650 $m^2/g$, a pore volume of 1.20 $cm^3/g$ and a median pore width of 0.51 nm. The elemental analysis of the calcined material showed 93.7 wt-% $SiO_2$, 6.2 wt-% $Al_2O_3$, and 0.1 wt-% $Na_2O$ in the sample, thus affording an $SiO_2:Al_2O_3$ atomic ratio (SAR) of 25.6.

Figure 3B:
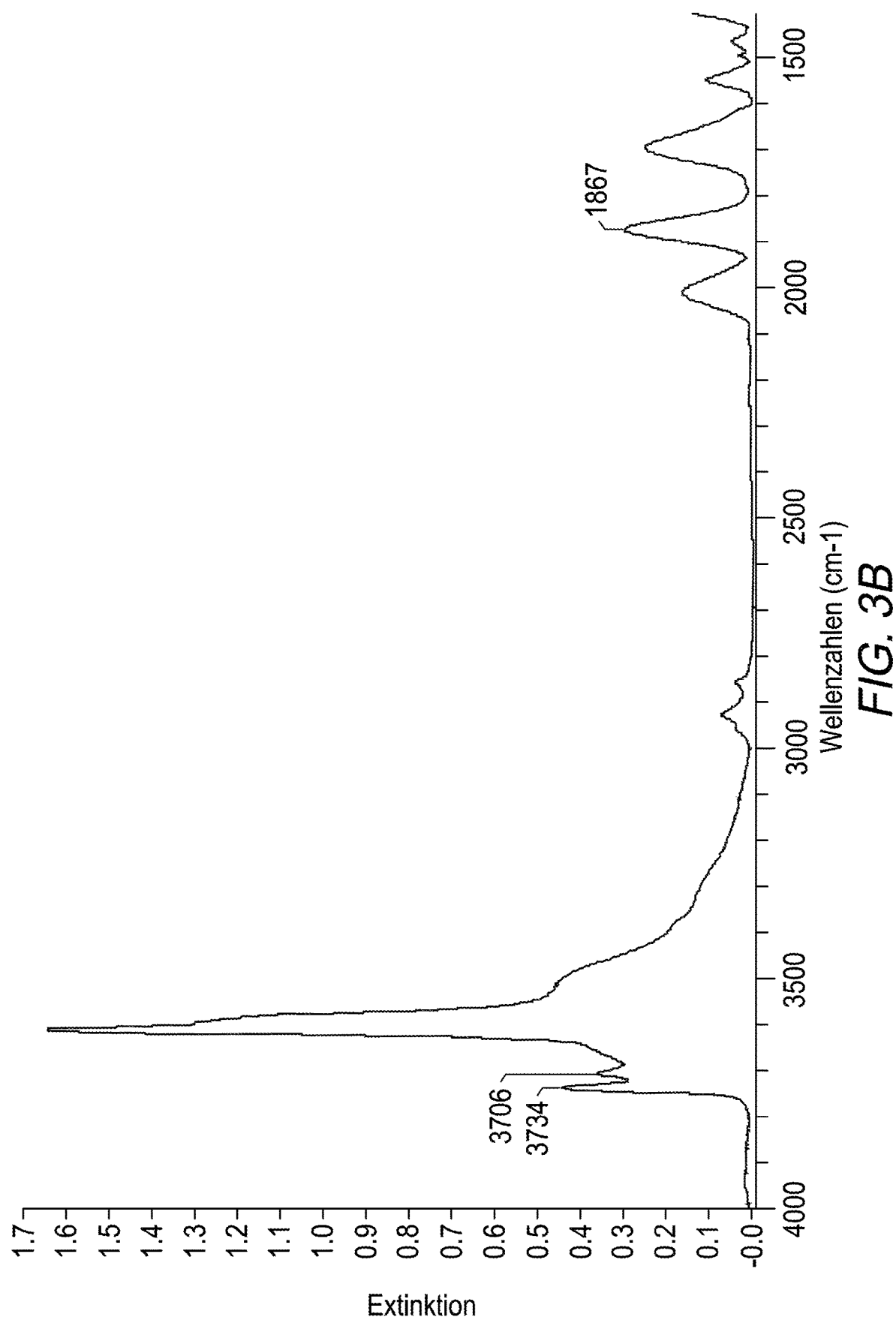

The IR-spectrum of the calcined sample is shown in FIG. 3b, wherein amongst others absorption bands having maxima at 3,734 $cm^{-1}$ and 1,867 $cm^{-1}$ may be seen, which display a ratio of maximum absorption of the former to the latter of 1.44.

The particle size distribution of the calcined sample afforded a D10 value of 0.15 μm, a D50 value of 0.43 μm, and a D90 value of 0.70 μm.

Figure 3C:
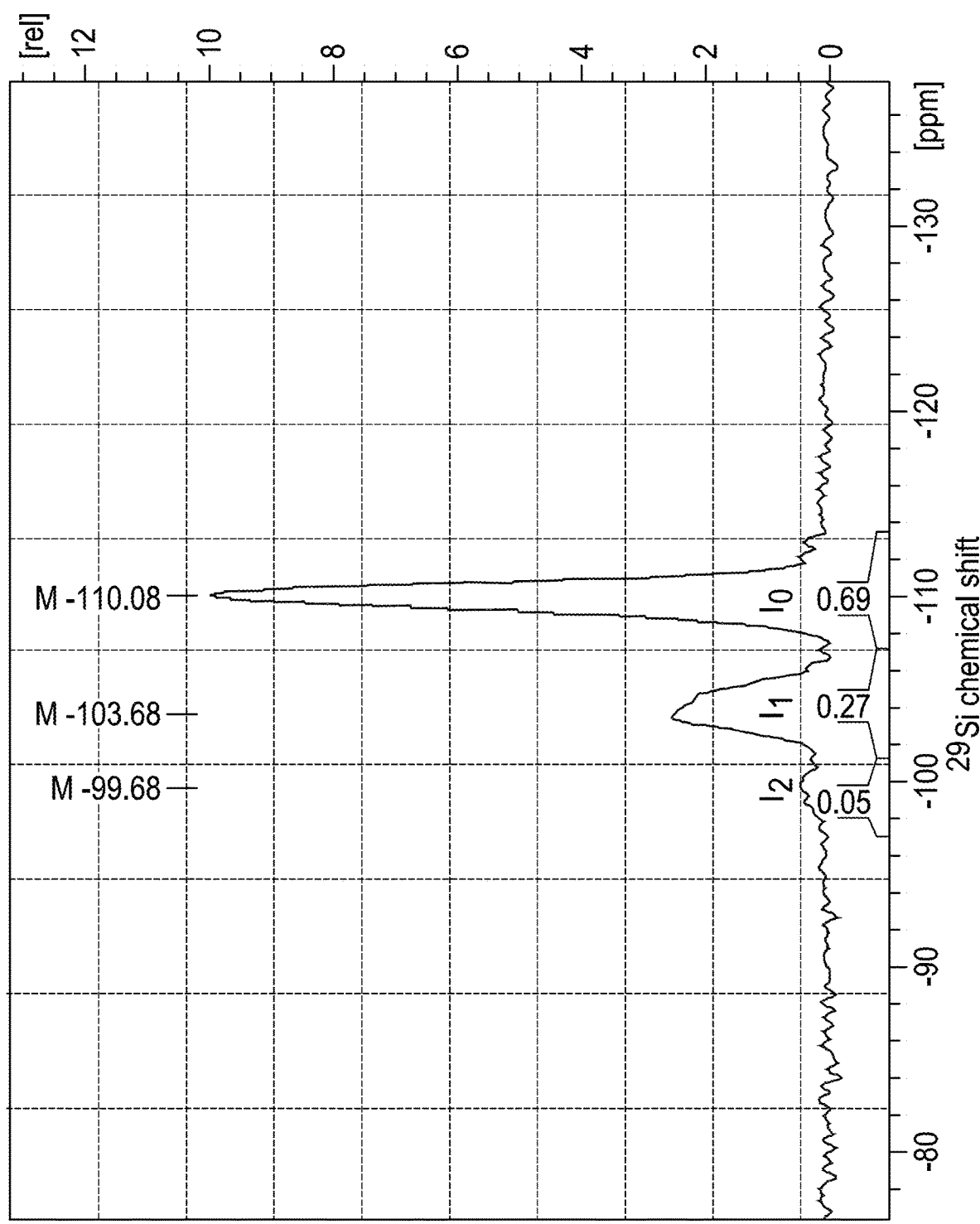

The $^{29}Si$ MAS NMR of the calcined zeolitic material is displayed in FIG. 3c and displays peaks at −103.68 and −110.08 ppm, wherein the integration of the peaks offers relative intensities of 0.391 and 1 for the signals, respectively.

Figure 3D:
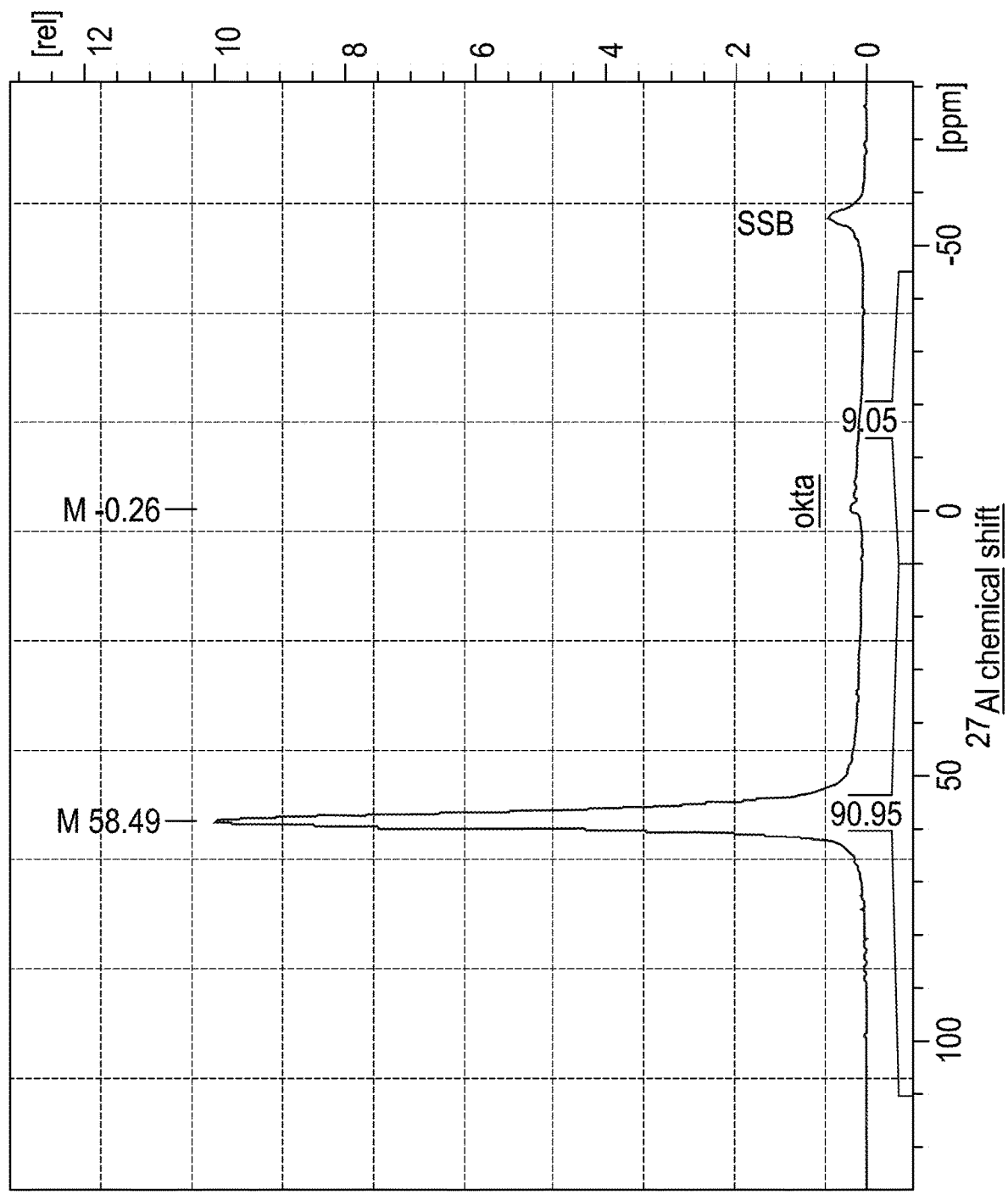

The $^{27}Al$ MAS NMR of the calcined zeolitic material is displayed in FIG. 3d and displays peaks at 58.49 and −0.26 ppm, wherein the integration of the peaks offers relative intensities of 1 and 0.1 for the signals, respectively.

Comparative Example 1: Preparation of a Zeolitic Material Having the CHA Framework Structure Using Trimethylcyclohexylammonium and Tetramethylammonium 534.54 g N,N,N-trimethycyclohexylammoniumhydroxide (20 wt-% solution in $H_2O$) were mixed with 56.54 g of aluminiumtriisopropylate and 150.62 g tetramethylammoniumhydroxide (25 wt-% solution in $H_2O$). Afterwards, 692.01 g LUDOX AS 40 (40 wt-% colloidal solution in $H_2O$) and 11 g CHA seeds were added to the stirred mixture. The resulting gel was placed in a stirred autoclave with a total volume of 2.5 L. The autoclave was heated within 7 h to 170° C. The temperature was kept constant for 15 h. Afterwards the autoclave was cooled down to room temperature. Then, the solids were separated by filtration and intensive washing until the washwater had a pH of 7. Finally the solid was dried for 10 hours at 120° C. Solid yield=327 g. The material was calcined at 550° C. for 5 hours.

The characterization of the calcined material via XRD confirmed the CHA-type framework structure of the product and afforded an average crystal size of 115 nm and a crystallinity of 91%.

The calcined material displayed a BET surface area of 621 $m^2/g$, a pore volume of 1.07 $cm^3/g$ and a median pore width of 0.68 nm. The elemental analysis of the calcined material showed 93.4 wt-% $SiO_2$, 6.4 wt-% $Al_2O_3$, and 0.2 wt-% $Na_2O$ in the sample, thus affording an $SiO_2:Al_2O_3$ atomic ratio (SAR) of 25.

Figure 4A:
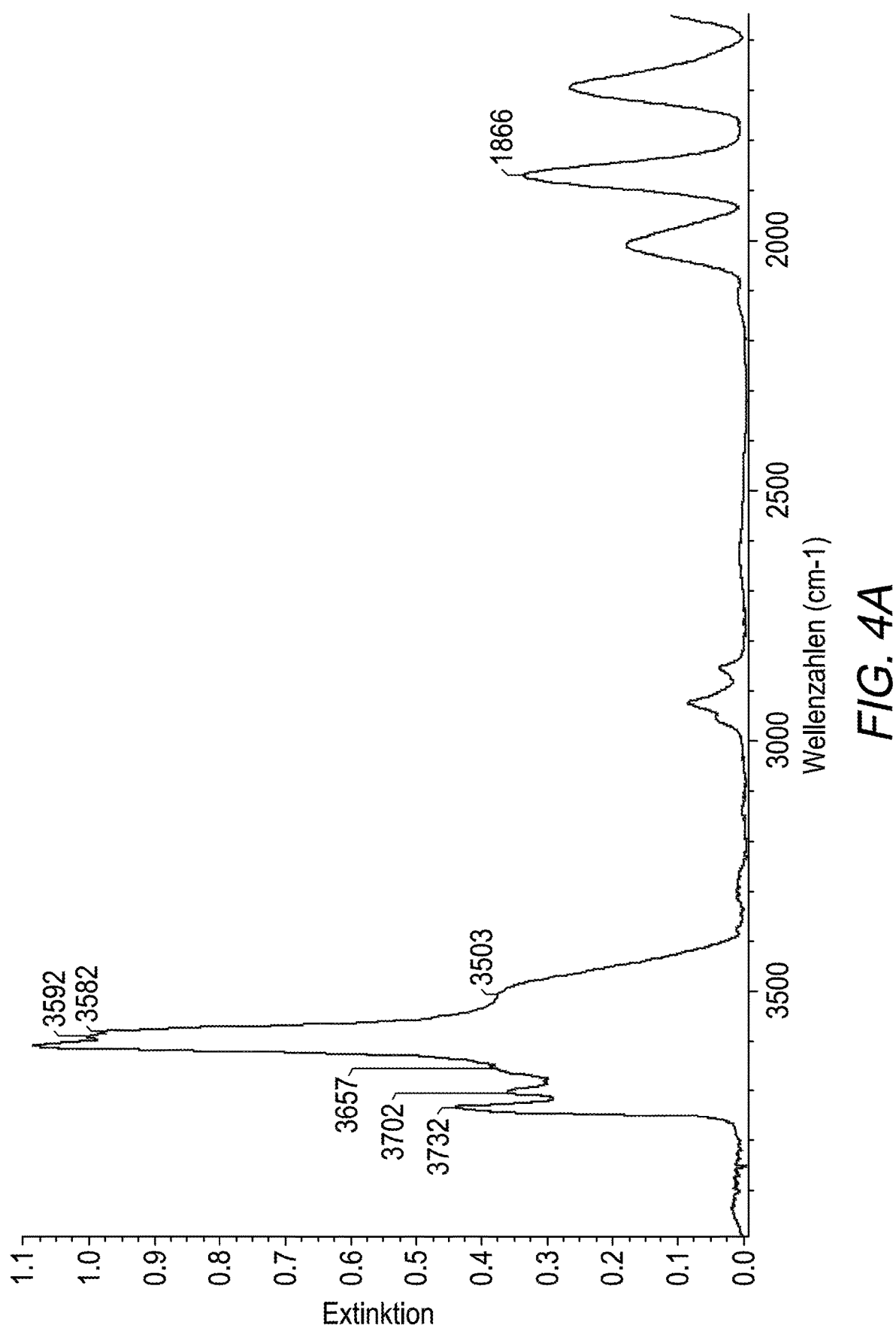

The IR-spectrum of the calcined sample is shown in FIG. 4a, wherein amongst others absorption bands having maxima at 3,732 $cm^{-1}$ and 1,866 $cm^{-1}$ may be seen, which display a ratio of maximum absorption of the former to the latter of 1.33.

The particle size distribution of the calcined sample afforded a D10 value of 0.61 µm, a D50 value of 0.92 µm, and a D90 value of 1.58 µm.

Figure 4B:
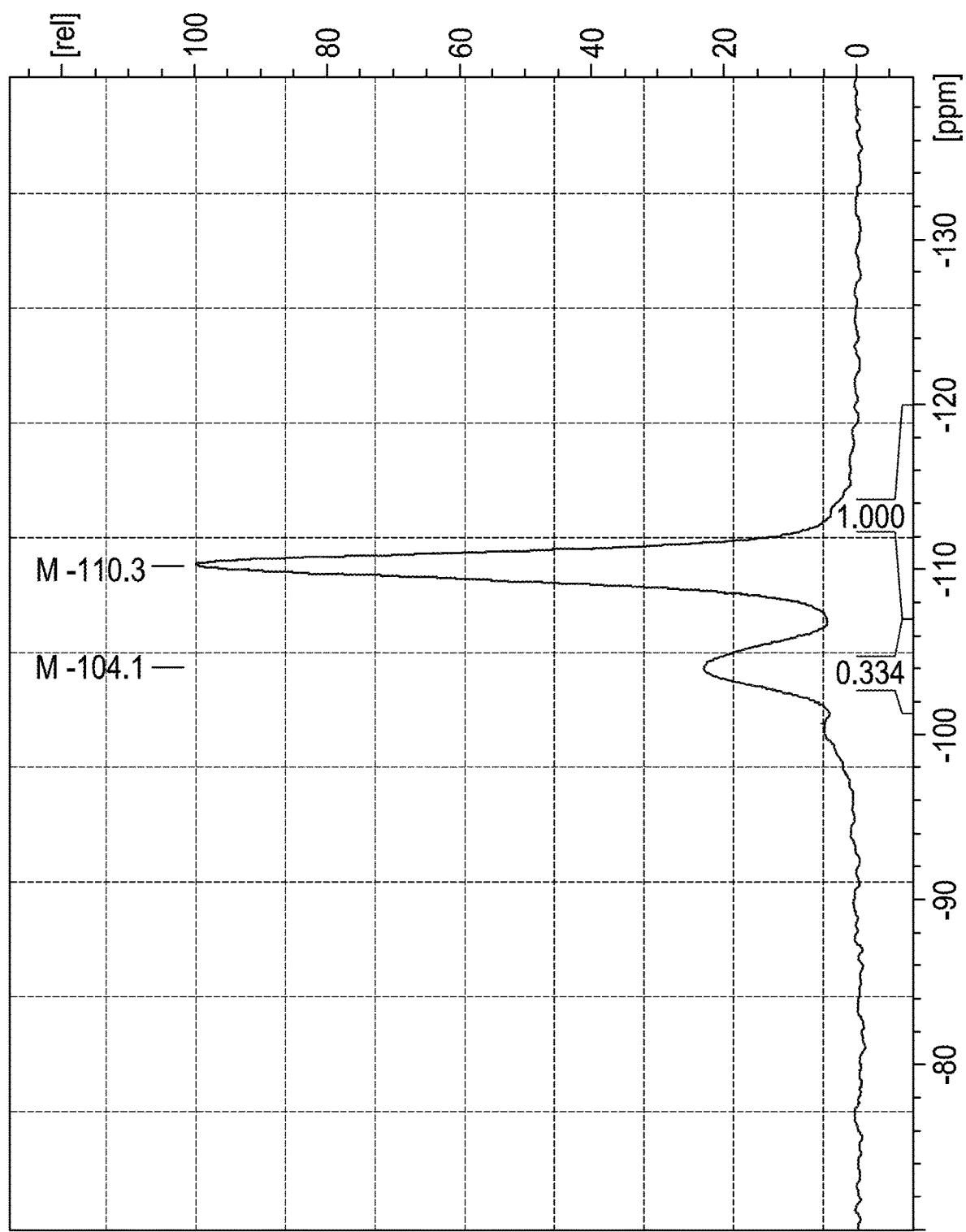

The $^{29}$Si MAS NMR of the calcined zeolitic material is displayed in FIG. 4b and displays peaks at −104.1 and −110.3 ppm, wherein the integration of the peaks offers relative intensities of 0.334 and 1 for the signals, respectively.

Figure 4C:
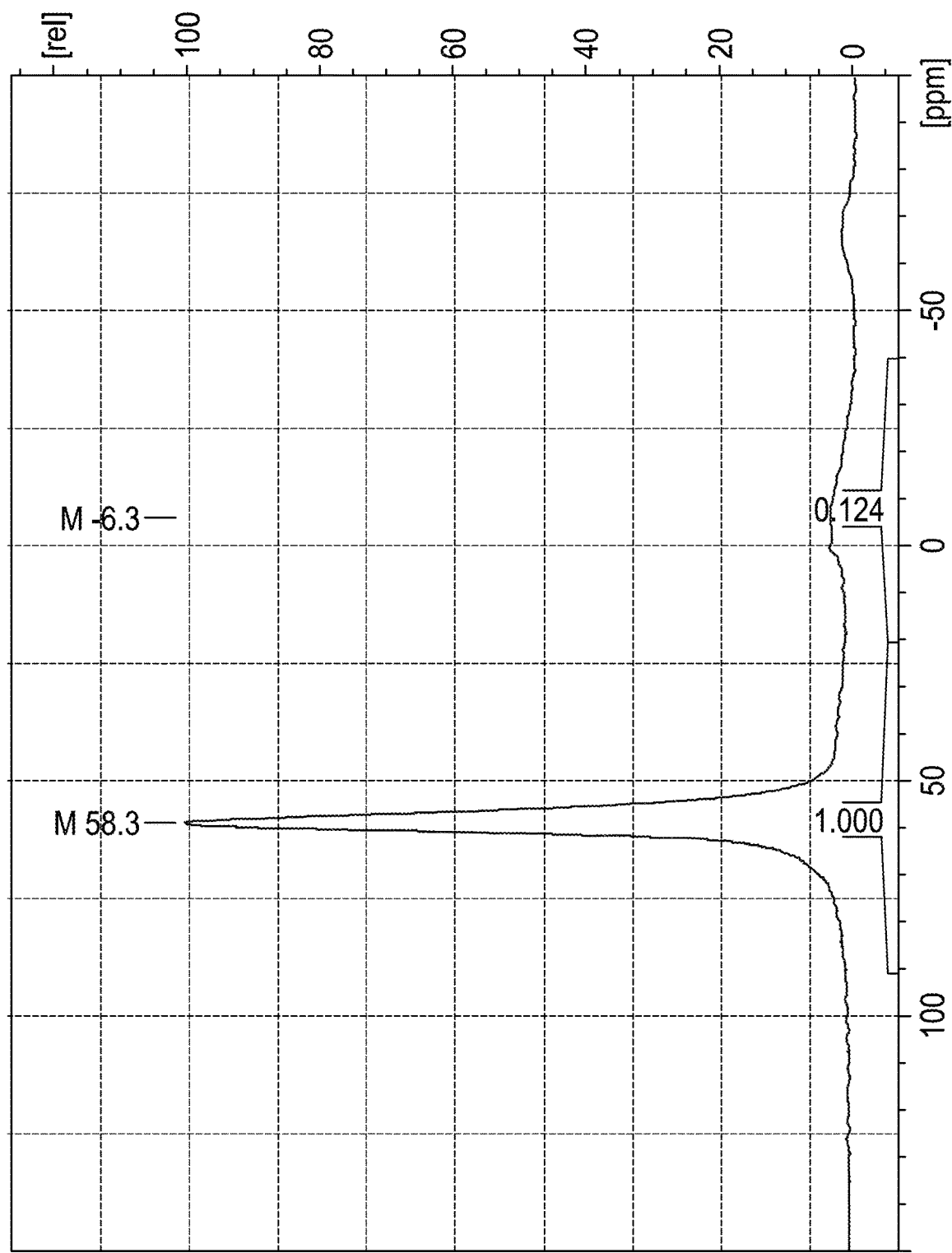

The $^{27}$Al MAS NMR of the calcined zeolitic material is displayed in FIG. 4c and displays peaks at 58.3 and −6.3 ppm, wherein the integration of the peaks offers relative intensities of 1 and 0.124 for the signals, respectively.

Comparative Example 2: Preparation of a Zeolitic Material Having the CHA Framework Structure Using Trimethylcyclohexylammonium and Tetramethylammonium 276.8 kg N,N,N-trimethylcyclohexylammoniumhydroxide (20 wt-% solution in $H_2O$) were mixed with 34.80 kg of aluminiumtriisopropylate and 77.99 kg tetramethylammoniumhydroxide (25 wt-% solution in $H_2O$). Afterwards, 358.32 kg LUDOX AS 40 (40 wt-% colloidal solution in $H_2O$) and 5.73 kg CHA seeds were added to the stirred mixture. The resulting gel was placed in a stirred autoclave with a total volume of 1600 L. The autoclave was heated within 7 h to 170° C. The temperature was kept constant for 18 h. Afterwards the autoclave was cooled down to room temperature. Then, the solids were separated by filtration and intensive washing until the washwater had a pH of 7. Finally the solid was dried for 10 hours at 120° C. The material was calcined at 550° C. for 5 hours.

Figure 5A:
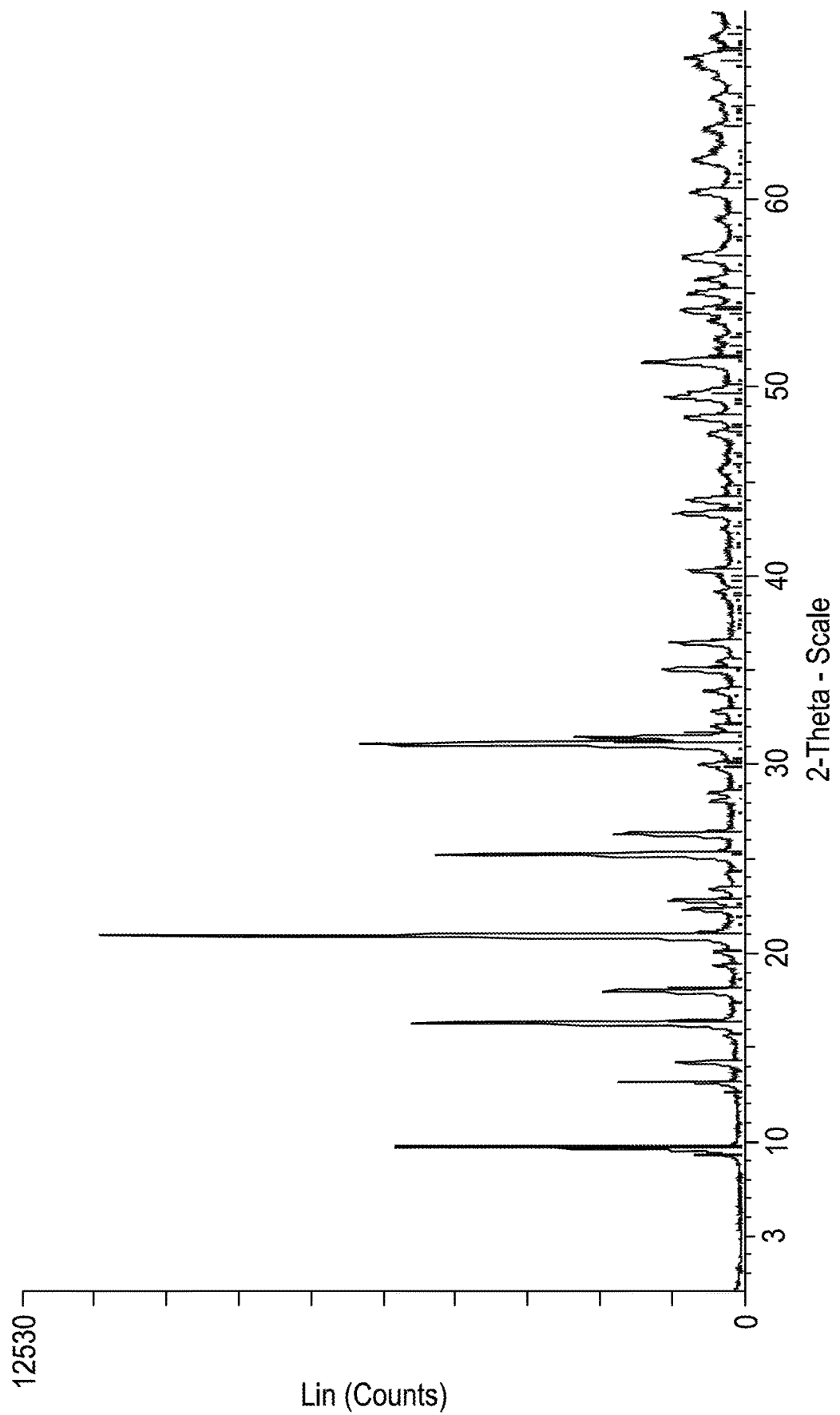

The characterization of the calcined material via XRD is displayed in FIG. 5a and displays the CHA-type framework structure of the product and afforded an average crystal size of 118 nm and a crystallinity of 92%. The calcined material displayed a BET surface area of 654 m$^2$/g, a pore volume of 1.09 cm$^3$/g and a median pore width of 0.68 nm. The elemental analysis of the calcined material showed 93.2 wt-% $SiO_2$, 6.6 wt-% $Al_2O_3$, and 0.2 wt-% $Na_2O$ in the sample, thus affording an $SiO_2$:$Al_2O_3$ atomic ratio (SAR) of 24.

Figure 5B:
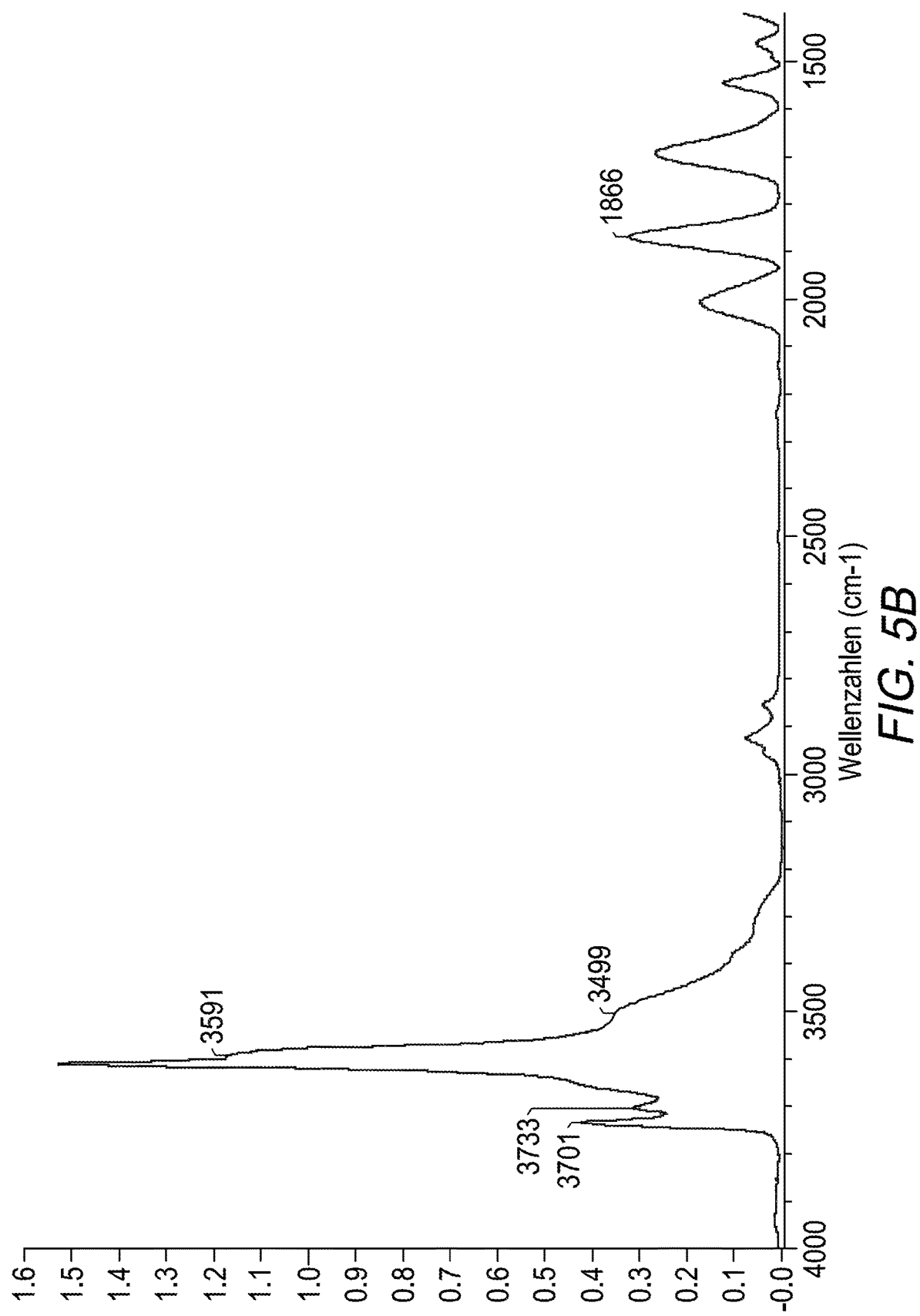

The IR-spectrum of the calcined sample is shown in FIG. 5b, wherein amongst others absorption bands having maxima at 3,733 cm$^{-1}$ and 1,866 cm$^{-1}$ may be seen, which display a ratio of maximum absorption of the former to the latter of 1.35.

The particle size distribution of the calcined sample afforded a D10 value of 0.39 µm, a D50 value of 0.58 µm, and a D90 value of 1.22 µm.

Figure 5C:
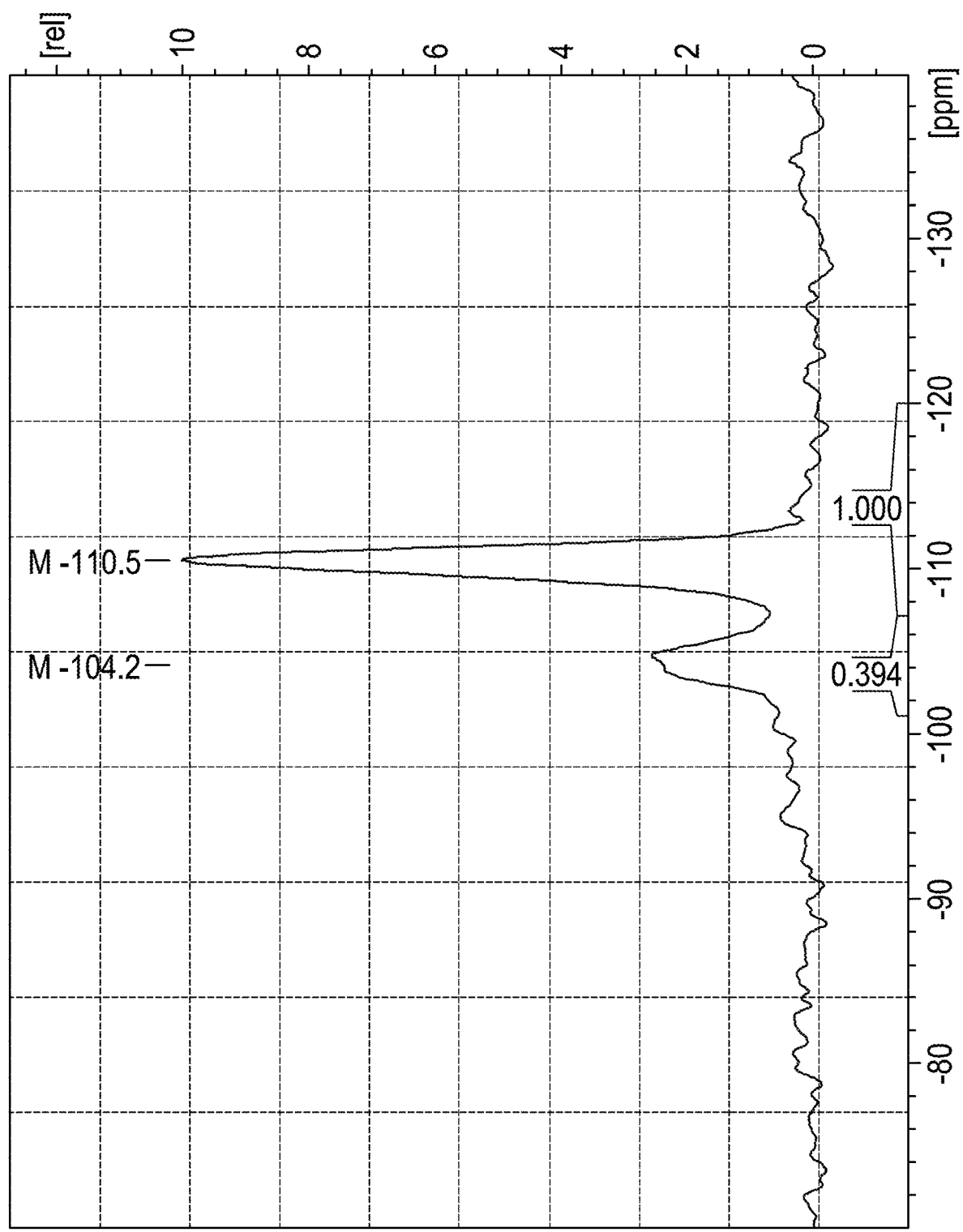

The $^{29}$Si MAS NMR of the calcined zeolitic material is displayed in FIG. 5c and displays peaks at −104.2 and −110.5 ppm, wherein the integration of the peaks offers relative intensities of 0.394 and 1 for the signals, respectively.

Figure 5D:
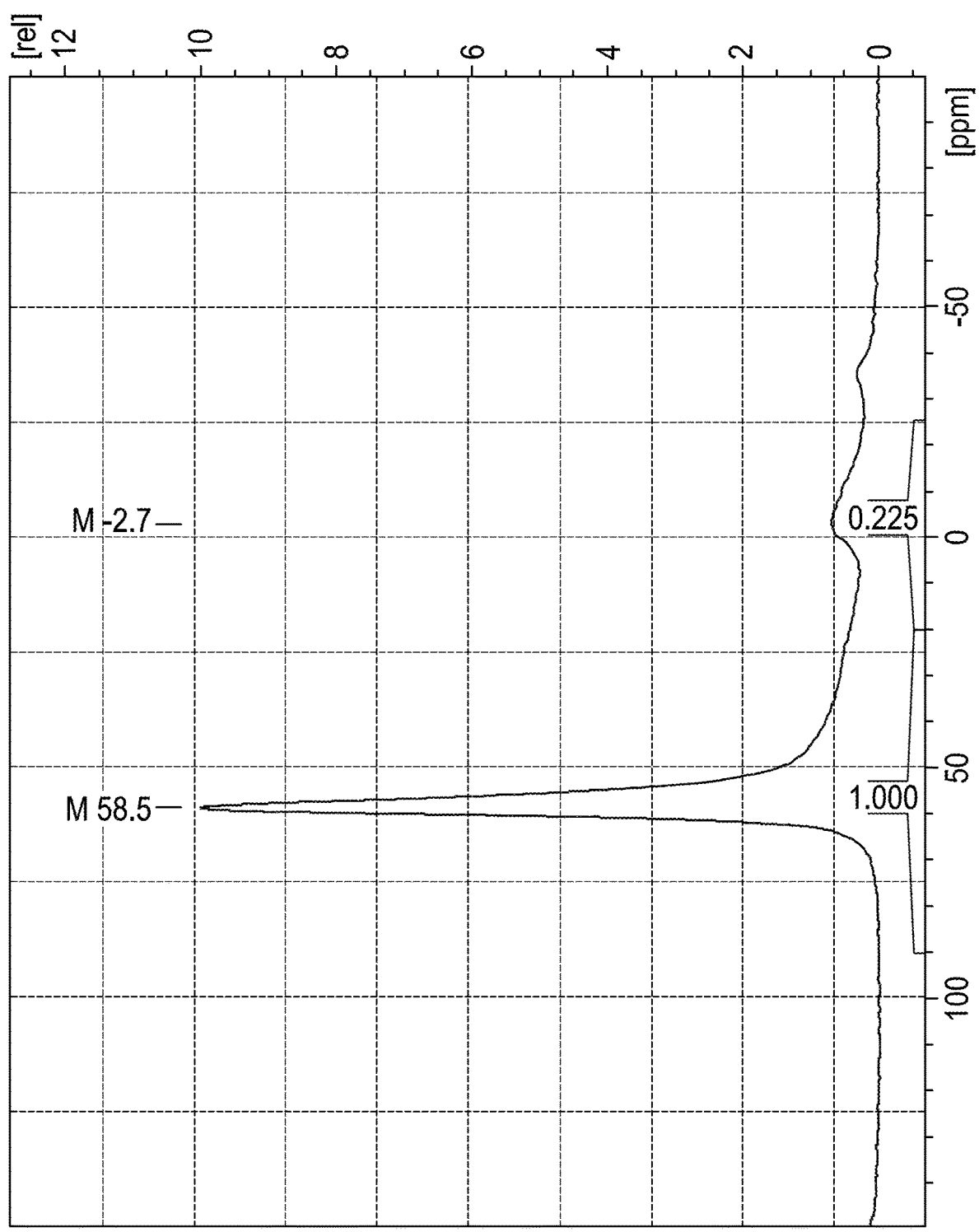

The $^{27}$Al MAS NMR of the calcined zeolitic material is displayed in FIG. 5d and displays peaks at 58.5 and −2.7 ppm, wherein the integration of the peaks offers relative intensities of 1 and 0.225 for the signals, respectively.

Example 4: Selective Catalytic Reduction Testing

The samples obtained according to Example 1 and according to comparative examples 1 and 2 were tested under a selective catalytic reduction conditions relative to their NO$_x$ conversion capacity. To this effect, the respective calcined samples were ion-exchanged with copper. The copper loaded samples were then aged at 850° C. for 6 hours in an atmosphere containing 10 volume percent of water. The aged samples were then contacted at various temperatures with a gas stream containing 500 ppm nitrogen oxide, 500 ppm ammonia, 5 volume percent water, 10 volume percent oxygen and balance nitrogen. Specifically, the capacity of the samples to convert nitrogen oxide under selective catalytic reduction conditions was tested at 200° C., 300° C., and 450° C. The results of said testing are displayed in table 1 below.

TABLE 1

Results from selective catalytic reduction testing conducted on the powder samples.

| | Sample (wt.-% Cu) | | |
|---|---|---|---|
| Temperature | Example 1 (2.60 wt. %) | Comp. Ex. 1 (2.50 wt.-%) | Comp. Ex. 2 (2.20 wt. %) |
| 200° C. | 94 | 75 | 90 |
| 300° C. | 100 | 84 | 93 |
| 450° C. | 89 | 80 | 84 |

For testing the samples under conditions which closely reflect the conditions experienced in the treatment of exhaust gas from automotive combustion engines, the aforementioned samples after having been ion-exchanged with copper were provided as a wash coat on a flow-through monolith substrate, wherein the coated substrate was then aged in an atmosphere containing volume percent water for 5 hours at 750° C. The coated monoliths were then contacted with the same gas stream employed for testing the powder samples at 200° C. and 600° C., respectively. The results from said "core" testing of the samples is displayed in table 2 below.

TABLE 2 results from selective catalytic reduction testing conducted on the coated monolith samples.

| | Sample | | |
|---|---|---|---|
| Temperature | Example 1 | Comp. Ex. 1 | Comp. Ex. 2 |
| 200° C. | 74 | 67 | 65 |
| 600° C. | 83 | 83 | 88 |

Thus, as may be taken from the results from selective catalytic reduction testing, it has surprisingly been found that both in the testing runs performed on the powder samples as well as on the testing performed on the coated monolith samples, the results obtained with the inventive sample clearly outperform those obtained with the comparative examples, in particular with respect to the conversion of nitrogen oxides at lower temperatures. Consequently, it has quite unexpectedly been found that inventive method not only provides for a highly efficient process for the preparation of a zeolitic material having a CHA framework structure, but furthermore quite surprisingly affords a material displaying an unexpectedly improved performance with respect to the conversion of nitrogen oxides under selective catalytic reduction conditions.

LIST OF THE CITED PRIOR ART REFERENCES

U.S. Pat. No. 4,544,538
WO-A-2008/083048
WO-A-2008/039742

WO-A-2008/033229
WO 2009/141324 A1
WO 2011/064186 A1
EP 2 325 143 A2
U.S. Pat. No. 4,610,854
US-A-2007/0043249
Zones et al. in Studies in Surface Science and Catalysis, Vol. 84, pp. 29-36
WO 2013/182974 A
US 2004/253163 A1

The invention claimed is:

1. A synthetic zeolitic material having a CHA-type framework structure, wherein the CHA-type framework structure comprises $YO_2$ and $X_2O_3$, wherein Y is a tetravalent element and X is a trivalent element, and wherein the IR-spectrum of the zeolitic material comprises:
   a first absorption band (B1) ranging from 3,720 to 3,750 $cm^{-1}$; and
   a second absorption band (B2) ranging from 1,850 to 1,890 $cm^{-1}$;
wherein the ratio of the maximum absorbance of the first absorption band to the second absorption band B1:B2 ranges from 1 to 2.5.

2. A process for the preparation of a zeolitic material having a CHA-type framework structure comprising $YO_2$ and $X_2O_3$, the process comprising:
   (1) obtaining a mixture comprising one or more sources for $YO_2$, one or more sources for $X_2O_3$, one or more optionally substituted ethyltrimethylammonium cation-containing compounds, and one or more tetraalkylammonium cation $R^1R^2R^3R^4N^+$-containing compounds as structure directing agent;
   (2) crystallizing the mixture obtained in (1) for obtaining a zeolitic material having a CHA-type framework structure;
   wherein Y is a tetravalent element and X is a trivalent element,
   wherein $R^1$, $R^2$, and $R^3$ are independently from one another alkyl, wherein $R^4$ is cycloalkyl, and
   wherein the $YO_2:X_2O_3$ molar ratio of the mixture in (1) ranges from 2 to 1,000.

3. The process of claim 2, wherein the mixture in (1) does not contain any substantial amount of a source for $Z_2O_5$, wherein Z is P.

4. The process of claim 2, wherein the one or more tetraalkylammonium cation $R^1R^2R^3R^4N^+$-containing compounds comprise one or more N,N,N-tri ($C_1$-$C_4$)alkyl-($C_5$-$C_7$)cycloalkylammonium compounds.

5. The process of claim 2, wherein Y is selected from the group consisting of Si, Sn, Ti, Zr, Ge, and mixtures of two or more thereof.

6. The process of claim 2, wherein X is selected from the group consisting of Al, B, In, Ga, and mixtures of two or more thereof.

7. The process of claim 2, wherein the molar ratio of the one or more optionally substituted ethyltrimethylammonium cations $C_2H_5N(CH_3)_3^+:YO_2$ in the mixture according to (1) ranges from 0.005 to 0.5.

8. The process of claim 2, wherein the molar ratio $C_2H_5N(CH_3)_3:R^1R^2R^3R^4N^+$ of the one or more optionally substituted ethyltrimethylammonium cations to the one or more tetraalkylammonium cations $R^1R^2R^3R^4N^+$ in the mixture according to (1) ranges from 0.01 to 5.

9. The process of claim 2 further comprising one or more of the following: (3) adjusting the pH of the crystallized mixture obtained in (2) to a pH ranging from 3 to 11, and/or
   (4) isolating the zeolitic material from the crystallized mixture in (2) or (3), and/or
   (5) washing the zeolitic material obtained in (2), (3), or (4), and/or
   (6) drying and/or calcining the zeolitic material obtained in (2), (3), (4), or (5), and/or
   (7) subjecting the zeolitic material to an ion-exchange procedure,
   wherein (3) and/or (4) and/or (5) and/or (6) and/or (7) can be conducted in any order.

10. The process of claim 9, wherein in (6) the zeolitic material is spray dried.

11. The process of claim 10, wherein the crystallized mixture obtained in (2) is directly subject to spray drying in (6).

12. A synthetic zeolitic material having a CHA-type framework structure obtained according to the process of claim 2.

13. The zeolitic material of claim 12, wherein the particle size D10 of the zeolitic material ranges from 150 to 300 nm,
   wherein the average particle size D50 of the zeolitic material ranges from 300 to 450 nm, and
   wherein the particle size D90 of the zeolitic material ranges from 500 to 900 nm.

14. The zeolitic material of claim 12, wherein the micropore volume of the zeolitic material determined according to DIN 66133 ranges from 0.5 to 3 $cm^3/g$.

15. A method of converting an organic compound by contacting said compound with a catalyst containing the synthetic zeolitic material of claim 12 under suitable conversion conditions.

16. A method for selectively reducing nitrogen oxides $NO_x$ by contacting a stream containing $NO_x$ with a catalyst containing the zeolitic material of claim 12 under suitable reducing condition.

17. A method of oxidizing $NH_3$ by contacting a stream containing $NH_3$ with a catalyst containing the zeolitic material of claim 12 under suitable oxidizing conditions.

18. A method of decomposing of $N_2O$ by contacting a stream containing $N_2O$ with a catalyst containing the zeolitic material of claim 12 under suitable decomposition conditions.

19. A method of controlling emissions in Advanced Emission Systems by contacting an emission stream with a catalyst containing the zeolitic material of claim 12 under suitable conditions.

20. A fluid catalytic cracking FCC process comprising adding the zeolitic material of claim 12 to the components of the FCC at a suitable time and under suitable conditions for the FCC process.

* * * * *